United States Patent
Lim et al.

(10) Patent No.: US 10,759,805 B2
(45) Date of Patent: Sep. 1, 2020

(54) COMPOUNDS THAT ARE ERK INHIBITORS

(71) Applicant: Merck Sharp & Dohme Corp., Rahway, NJ (US)

(72) Inventors: Jongwon Lim, Lexington, MA (US); Xianhai Huang, Warren, NJ (US); Ronald D. Ferguson, Scotch Plains, NJ (US); Wei Zhou, Scotch Plains, NJ (US); Christopher W. Boyce, Flemington, NJ (US); Phieng Siliphaivanh, Newton, MA (US); David J. Witter, Norfolk, MA (US); Milana M. Maletic, Summit, NJ (US); Joseph A. Kozlowski, Princeton, NJ (US); Kevin J. Wilson, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/032,715

(22) Filed: Jul. 11, 2018

(65) Prior Publication Data
US 2018/0319804 A1 Nov. 8, 2018

Related U.S. Application Data

(62) Division of application No. 15/656,176, filed on Jul. 21, 2017, now Pat. No. 10,065,967, which is a division of application No. 14/787,280, filed as application No. PCT/US2014/035384 on Apr. 25, 2014, now Pat. No. 9,745,307.

(60) Provisional application No. 61/817,571, filed on Apr. 30, 2013.

(51) Int. Cl.
*C07D 471/04* (2006.01)
*C07D 471/14* (2006.01)
*C07D 519/00* (2006.01)
*C07D 487/04* (2006.01)

(52) U.S. Cl.
CPC ......... *C07D 487/04* (2013.01); *C07D 471/04* (2013.01); *C07D 471/14* (2013.01); *C07D 519/00* (2013.01)

(58) Field of Classification Search
CPC .. C07D 487/14; C07D 487/04; A61K 31/519; A61K 31/4439
USPC ...................................................... 544/251
See application file for complete search history.

(56) References Cited

U.S. PATENT DOCUMENTS

| | | | | | |
|---|---|---|---|---|---|
| 4,325,931 | A | * | 4/1982 | Lewis ...................... | B01J 23/78 423/363 |
| 4,352,931 | A | * | 10/1982 | Cuny ................... | C07D 487/04 544/251 |
| 2005/0203063 | A1 | * | 9/2005 | Deshaies .............. | A61K 31/785 514/63 |

FOREIGN PATENT DOCUMENTS

WO    WO2008156739    12/2008

OTHER PUBLICATIONS

Foster et al., J. Org. Chem. vol. 45 pp. 3072-3077. Published 1980. (Year: 1980).*
Patani et al., (Chemical Reviews vol. 96 p. 3147-3176. Published 1996). (Year: 1996).*
Meanwell et al., (J.Med. Chem. vol. 54 pp. 2529-2591. Published 2011). (Year: 2011).*
Foster et al (JOC vol. 45 pp. 3072-3077 published 1980). (Year: 1980).*
U.S. Appl. No. 14/787,280, filed Oct. 27, 2015.
U.S. Appl. No. 15/656,176, filed Jul. 21, 2017.
European Communication—Application No. 14791539.1-1462/ 2991654 PCT/US2014035384, dated Nov. 14, 2016—8 pages.
Julen Oyarzabal, Discovery of Mitogen-Activated Protein Kinase-Interacting Kinase 1 Inhibitors by a Comprehensive, Journal of Medicinal Chemistry, Sep. 23, 2010, 6618-6628, 53-18.
PubChem NSC350006, Compound Summary for CID 336305, Create date: Mar. 26, 2005. [retrieved on Aug. 6, 2014]. Retrieved from the internet URL: https://pubchem.ncbi.nlm.nih.gov/compound/ 336305?from=summary.
Robert H. Foster, Synthesis of prox-Benzoisoallopurinol, J. Org. Chem., Feb. 5, 1980, 3072-3077, 45-15.
Sequeria, S. et al., Synthesis of Fused Indazole Derivatives, Indian Journal of Chemistry, May 1987, 436-439, 26B.

* cited by examiner

*Primary Examiner* — Timothy P Thomas
*Assistant Examiner* — George W Kosturko
(74) *Attorney, Agent, or Firm* — Jeffrey P. Bergman; Catherine D. Fitch

(57) ABSTRACT

Disclosed are the ERK inhibitors of formula (1):

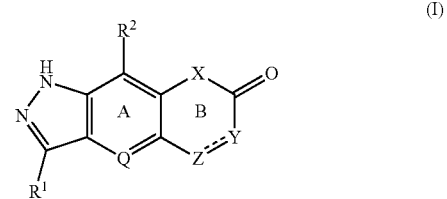

and the pharmaceutically acceptable salts thereof. Also disclosed are methods of treating cancer using the compounds of formula (I).

14 Claims, No Drawings

COMPOUNDS THAT ARE ERK INHIBITORS

This application is a divisional application based on U.S. patent application Ser. No. 15/656,176, and which is a divisional application based on U.S. patent application Ser. No. 14/787,280, now U.S. Pat. No. 9,745,307, which is a U.S. national phase under 35 U.S.C. § 371 of International Application No. PCT/US14/035384, filed Apr. 25, 2014, which claims the benefit under 35 U.S.C. § 119(e) to U.S. Provisional Application No. 61/817,571 filed Apr. 30, 2013. The contents of each of these applications are incorporated herein by reference in their entireties.

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (ERK2 activity), which small-molecules would be useful for treating a broad spectrum of cancers, such as, for example, melanoma, pancreatic cancer, thryroid cancer, colorectal cancer, lung cancer, breast cancer, and ovarian cancer. Such a contribution is provided by this invention.

SUMMARY OF THE INVENTION

This invention provides compounds that inhibit the activity of ERK2.

Thus, this invention provides compounds that are ERK inhibitors (i.e., ERK2 inhibitors), said compounds being of the formula (I):

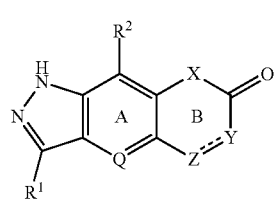

(I)

or a pharmaceutically acceptable salt, ester, solvate or prodrug thereof, wherein: Ring B is a 6 or 7 membered ring fused to Ring A (i.e., Ring A and Ring B have two atoms in common), and Q, $R^1$, $R^2$, $R^3$, X, Y and Z are defined below.

This invention provides: (1) compounds of formula (I); (2) compounds of formula (I) in pure or isolated form; (3) pharmaceutically acceptable salts of the compounds of formula (I); (4) solvates of the compounds of formula (I); (5) compounds of formula (I) wherein from one to all of the hydrogens are deuterium; (6) compounds of formula (I) wherein at least one H is deuterium; (7) compounds of formula (I) wherein 1 to 5H are deuterium; (8) compounds of formula (I) wherein 1 to 2H are deuterium; and (9) compounds of formula (I) wherein one H is deuterium.

This invention provides compounds of formula (I) in the free base form.

This invention provides compounds of formula (I) in a pharmaceutically acceptable salt form.

This invention also provides compounds (1) to (47).

This invention also provides a pharmaceutical composition comprising an effective amount of at least one (e.g., 1) compound of formula (I) and a pharmaceutically acceptable carrier. This invention also provides a pharmaceutical composition comprising an effective amount of at least one (e.g., 1) pharmaceutically acceptable salt of a compound of formula (I) and a pharmaceutically acceptable carrier. This invention also provides a pharmaceutical composition comprising an effective amount of at least one (e.g., 1) compound of formula (I) and an effective amount of at least one (e.g., 1) other pharmaceutically active ingredient (such as, for example, a chemotherapeutic agent), and a pharmaceutically acceptable carrier.

This invention also provides a method of inhibiting ERK (i.e., inhibiting the activity of ERK2) in a patient in need of such treatment comprising administering to said patient an effective amount of at least one (e.g., 1) compound of formula (I). This invention also provides a method of inhibiting ERK (i.e., inhibiting the activity of ERK2) in a patient in need of such treatment comprising administering to said patient an effective amount of at least one (e.g., 1) pharmaceutically acceptable salt of a compound of formula (I).

This invention also provides a method for treating cancer in a patient in need of such treatment, said method comprising administering to said patient an effective amount of at least one (e.g., 1) compound of formula (I). This invention also provides a method for treating cancer in a patient in need of such treatment, said method comprising administering to said patient an effective amount of at least one (e.g., 1) pharmaceutically acceptable salt of a compound of formula (I). This invention also provides a method for treating cancer in a patient in need of such treatment, said method comprising administering to said patient an effective amount of at least one (e.g., 1) compound of formula (1), in combination with an effective amount of at least one chemotherapeutic agent. This invention also provides a method for treating cancer in a patient in need of such treatment, said method comprising administering to said patient an effective amount of at least one (e.g., 1) pharmaceutically acceptable salt of a compound of formula (1), in combination with an effective amount of at least one chemotherapeutic agent. The methods of this invention include the administration of a pharmaceutical composition comprising at least one (e.g., 1) compound, or pharmaceutically acceptable salt thereof, of this invention and a pharmaceutically acceptable carrier. This invention also provides any of the above methods of treating cancer wherein the cancer is colorectal. This invention also provides any of the above methods of treating cancer wherein the cancer is melanoma.

The methods of treating cancers described herein can optionally include the administration of an effective amount of radiation (i.e., the methods of treating cancers described herein optionally include the administration of radiation therapy).

DETAILED DESCRIPTION OF THE INVENTION

All patents, publications and pending patent applications identified herein are hereby incorporated by reference.

As described herein, unless otherwise indicated, the use of a drug or compound in a specified period is per treatment cycle. For example, once a day means once per day of each day of the treatment cycle, and once a week means one time per week during the treatment cycle.

The following abbreviations have the following meanings unless defined otherwise: Ac is acetyl; ACN is acetonitrile; AcOEt is ethyl acetate; AcOH (or HOAc) is acetic acid; aq is aqueous; atm is atmosphere; Bn (or BN) is benzyl; Boc (or BOC) is tert-butoxycarbonyl; Brettphos is 2-(dicyclohexyl-phosphino)3,6-dimethoxy-2',4',6'-triisopropyl-1,1'-biphenyl; Brettphos palladacycle is (chloro[2-(dicyclohexylphos-phino)-3,6-dimethoxy-2',4',6'-triisopropyl-1,1'-biphenyl][2-(2-aminoethyl)phenyl]palladium(II); Bu is butyl; Bz is benzoyl; DCE is 1,2-dichloroethane; DCM is dichloromethane; DIPEA (or DIEA or Hunig's Base) is N,N,-diisopropylethylamine; DMF is N,N-dimethylformamide; DMSO is dimethylsulfoxide; Dppf is 1,1'-bis(diphenyl-phosphino)ferrocene; Et is ethyl; EtOAc is ethyl acetate; g is grams; h is hour; HPLC is high pressure liquid chromatography; LCMS is liquid chromatography mass spectrometry; LG is leaving group; LHMDS or LiHMDS is lithium hexamethyldisilazide; Me is methyl; MeOH is methanol; mg is milligrams; min is minute; mL is milliliters; mmole is millimoles; MS is mass spectrometry; NBS is N-bromosuccinimide; NMR is nuclear magnetic resonance spectroscopy; PG is protecting group; Ph (or PH) is phenyl; $Pd_2(dba)_3$ is tris(dibenzylide-neacetone)dipalladium (0); prep means preparative; PTLC is preparative thin layer chromatography; Pr is propyl; RP is reverse-phase; RT (or rt) is room temperature; sat is saturated; SM is starting material; t-butyl is tert-butyl; TEA is triethylamine ($Et_3N$); TFA is trifluoroacetic acid; THF is tetrahydrofuran; TLC is thin layer chromatography; Trt or trityl is triphenyl methane; Xantphos is 4,5-bis(diphenyl-phosphino)-9,9-dimethylxanthene; and µl is microliters.

As used herein, unless otherwise specified, the terms below have the meaning indicated.

Unless otherwise specified, the bond from a fused ring moiety to the rest of the molecule can be from any ring of the fused ring moiety.

The term "composition" is intended to encompass a product comprising the specified ingredients in the specified amounts, as well as any product which results, directly or indirectly, from combination of the specified ingredients in the specified amounts.

The term "anti-cancer agent" means a drug (medicament or pharmaceutically active ingredient) for treating cancer.

The term "antineoplastic agent" means a drug (medicament or pharmaceutically active ingredient) for treating cancer (e.g., a chemotherapeutic agent).

The term "at least one" means one or more than one. In one example "at least one" means 1-4, and in another example 1-3, and in another example 1-2, and in another example 1. The meaning of "at least one" with reference to the number of compounds of this invention is independent of the meaning with reference to the number of chemotherapeutic agents.

The term "chemotherapeutic agent" means a drug (medicament or pharmaceutically active ingredient) for treating cancer (e.g., an antineoplastic agent).

The term "compound" with reference to the antineoplastic agents, includes the agents that are antibodies.

The term "consecutively" means one following the other.

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of this invention) is that amount which results in the reduction in ERK (ERK2) activity and phosphorylation. The reduction in ERK activity may be determined by the analysis of pharmacodynamic markers such as phosphorylated RSK1,2 using techniques well known in the art.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The term "one or more" has the same meaning as "at least one".

The term "patient" means an animal, such as a mammal (e.g., a human being, and preferably a human being).

The term sequentially-represents (1) administration of one component of the method ((a) compound of the invention, or (b) chemotherapeutic agent, signal transduction inhibitor and/or radiation therapy) followed by administration of the other component or components. After administration of one component, the next component can be administered substantially immediately after the first component, or the next component can be administered after an effective time period following the administration of the first component. The effective time period is the amount of time given for realization of maximum benefit from the administration of the first component.

The term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like; "hydrate" is a solvate wherein the solvent molecule is $H_2O$.

The term "fused" with reference to, for example, two fused rings means that the two rings have two atoms in common.

The term "monocyclic", as used to describe a ring, means the ring is a single ring (i.e., the ring is not a fused ring). Thus, for example, a "monocyclic heteroaryl ring" means a single heteroaryl ring.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, unless otherwise specified, the terms below have the meanings indicated, and unless otherwise specified, the definitions of each term (i.e., moiety or substituent) apply when that term is used individually or as a component of another term (e.g., the definition of aryl is the same for aryl and for the aryl portion of arylheterocycloalkyl, and the like).

The term "alkenyl" means an aliphatic hydrocarbon group (chain) comprising at least one carbon to carbon double bond, wherein the chain can be straight or branched, and wherein said group comprises about 2 to about 15 carbon atoms. Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; non-limiting examples of suitable alkenyl groups include ethenyl, propenyl, n-butenyl, 3-methylbut-2-enyl, n-pentenyl, octenyl and decenyl.

The term "alkoxy" means an alkyl-O— group (i.e., the bond to the parent moiety is through the ether oxygen) in which the alkyl group is as defined below. Non-limiting examples of suitable alkoxy groups include methoxy, ethoxy, n-propoxy, isopropoxy, n-butoxy and heptoxy.

The term "alkyl" (including the alkyl portions of other moieties, such as alkoxy) means an aliphatic hydrocarbon group (chain) that can be straight or branched wherein said group comprises about 1 to about 20 carbon atoms in the chain. In one example said alkyl group comprises about 1 to about 12 carbon atoms in the chain, in another example about 1 to about 6 carbon atoms in the chain; in another example 1 to about 4 carbon atoms in the chain; and in another example 1 to about 2 carbon atoms in the chain. Branched alkyl means that one or more lower alkyl groups, such as methyl, ethyl or propyl, are attached to a linear alkyl chain. "Lower alkyl" means a group comprising about 1 to about 6 carbon atoms in the chain, and said chain can be straight or branched.

The term "alkylene" (including the alkylene portions of other moieties, such as -alkylene-aryl) means a chain comprising at least one —(CH$_2$)— group. Examples of alkylene chains include, but are not limited to: —(CH$_2$)$_{1-6}$—, —(CH$_2$)$_{1-4}$—, —(CH$_2$)$_{1-2}$— and —(CH$_2$)—.

The term "amino" means an —NH$_2$ group.

The term "aryl" (sometimes abbreviated "ar") (including the aryl portion of fused heteroarylaryl and fused arylheterocycloalkyl) means an aromatic monocyclic or multicyclic ring system comprising about 6 to about 14 carbon atoms, preferably about 6 to about 10 carbon atoms. Non-limiting examples of suitable aryl groups include phenyl and naphthyl.

The term "arylalkyl" (or aralkyl) means an aryl-alkyl- group (i.e., the bond to the parent moiety is through the alkyl group) wherein the aryl and alkyl moieties are as defined above; preferred arylalkyls comprise a lower alkyl group; non-limiting examples of suitable aralkyl groups include benzyl, 2-phenethyl and naphthalenylmethyl.

The term "cycloalkyl" means a non-aromatic mono- or multicyclic ring system comprising about 3 to about 7 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

The term "halo" means fluoro, chloro, bromo, or iodo groups. Preferred halos are fluoro, chloro or bromo, and more preferred are fluoro and chloro.

The term "halogen" means fluorine, chlorine, bromine, or iodine. Preferred halogens are fluorine, chlorine and bromine.

The term "heteroaryl" means an aromatic monocyclic or multicyclic ring system (e.g., a fused ring system) comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls comprise about 5 to about 6 ring atoms. The prefix aza, oxa or thia before the heteroaryl root name means that at least a nitrogen, oxygen or sulfur atom, respectively, is present as a ring atom. A nitrogen atom of a heteroaryl can be optionally oxidized to the corresponding N-oxide. The heteroaryl multicyclic ring system includes two rings fused together (i.e., there are two atoms common to both rings). Examples of the heteroaryl multicyclic ring system include fused heteroarylaryl rings (i.e., a heteroaryl ring fused to an aryl ring), and fused heteroarylheteroaryl rings (i.e., a heteroaryl ring fused to a heteroaryl ring). Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, benzopyrazolyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine

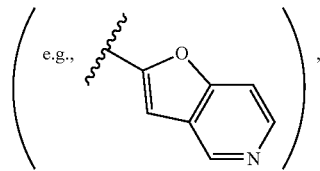

and the like.

The term "heteroarylalkyl" (or heteroaralkyl) means a heteroaryl-alkyl- group (i.e., the bond to the parent moiety is through the alkyl group) in which the heteroaryl and alkyl moieties are as defined above; preferred heteroarylalkyls comprise an alkyl group that is a lower alkyl group; non-limiting examples of suitable aralkyl groups include pyridyl-CH$_2$—, pyrimidinyl-CH$_2$—, imidazolyl-CH$_2$; pyrazinyl-CH$_2$—, and thiazolyl-CH$_2$—.

The term "fused heteroarylaryl" means a monocyclic heteroaryl ring fused to an aryl ring (i.e., the heteroaryl ring and the aryl ring have two atoms in common).

The term "fused (substituted heteroarylaryl)" means a monocyclic heteroaryl ring fused to an aryl ring (i.e., the heteroaryl ring and the aryl ring have two atoms in common) wherein one or both rings are substituted.

The term "fused heteroarylheteroaryl" means a monocyclic heteroaryl ring fused to a monocyclic heteroaryl ring (i.e., one heteroaryl ring has two atoms in common with the other heteroaryl ring), and each heteroaryl ring is independently selected.

The term "substituted fused heteroarylheteroaryl" (or "fused (substituted heteroarylheteroaryl") means a monocyclic heteroaryl ring fused to a monocyclic heteroaryl ring (i.e., one heteroaryl ring has two atoms in common with the other heteroaryl ring), wherein one or both rings are substituted. Each heteroaryl ring is independently selected.

The term "fused arylheteroaryl" means an aryl ring fused to a monocyclic heteroaryl ring (i.e., the aryl ring and the heteroaryl ring have two atoms in common).

The term "fused (substituted arylheteroaryl)" means an aryl ring fused to a monocyclic heteroaryl ring (i.e., the aryl ring and the heteroaryl ring have two atoms in common) wherein one or both rings are substituted.

The term "fused heterocycloalkylaryl" means a heterocycloalkyl ring fused to an aryl ring (i.e., the heterocycloalkyl ring and the aryl ring have two atoms in common).

The term "substituted fused heterocycloalkyaryl" means a heterocycloalkyl ring fused to an aryl ring (i.e., the heterocycloalkyl ring and the aryl ring have two atoms in common), wherein one or both rings are substituted.

The term "fused heterocycloalkylheteroaryl" means a heterocycloalkyl ring fused to a heteroaryl ring (i.e., the heterocycloalkyl ring and the heteroaryl ring have two atoms in common).

The term "substituted fused heterocycloalkylheteroaryl" means a heterocycloalkyl ring fused to a heteroaryl ring (i.e., the heterocycloalkyl ring and the heteroaryl ring have two atoms in common), wherein one or both rings are substituted.

The term "heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom, respectively, is present as a ring atom. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo[2.2.1]heptenyl; non-limiting examples of suitable monocyclic thiaheterocyclenyl rings include dihydrothiophenyl, dihydrothiopyranyl, and the like.

The term "heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include azetidinyl, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. The heterocycloalkyl rings of this invention can be "bridged heterocycloalkyl rings. The term "bridged heterocycloalkyl'" (or "bridged heterocyclyl") means a heterocycloalkyl group as defined above having an alkylene chain (generally a 1 or 2 carbon alkylene chain, not counting the atoms in the ring to which the alkylene chain is bound) bridging two carbon atoms in the ring.

Any carbon or heteroatom with unsatisfied valences in the text, schemes, examples, structural formulae, and any tables herein is assumed to have the hydrogen atom or atoms to satisfy the valences. And any one or more of these hydrogen atoms can be deuterium.

Those skilled in the art will appreciate that formulas showing a bond that does not have a substituent at the end of the bond represents a methyl group. Thus, for example,

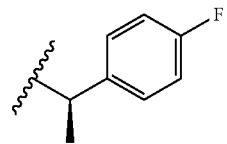 [SMILES: *[C@H](C)c1ccc(F)cc1]

is the same moiety as

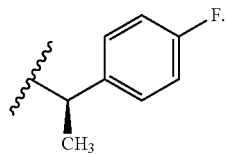

One or more compounds of the invention may also exist as, or be optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. Also, for example, all keto-enol and imine-enamine forms of the compounds are included in the invention.

Tautomeric forms such as, for example, the moieties:

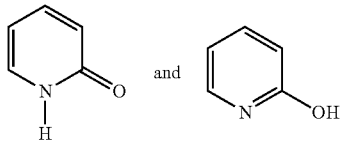 [SMILES: O=c1cccc[nH]1 ; Oc1ccccn1]

are considered equivalent in certain embodiments of this invention.

Thus, all stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (1) may be atropisomers and are considered as part of this invention. Enantiomers can also be separated by use of chiral HPLC column.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula (1) or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

This invention also includes the compounds of this invention in isolated and purified form.

Polymorphic forms of the compounds of formula (1), and of the salts, solvates and prodrugs of the compounds of formula (1), are intended to be included in the present invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

All such acid and base salts are intended to be pharmaceutically acceptable salts within the scope of the invention and all acid and base salts are considered equivalent to the free forms of the corresponding compounds for purposes of the invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

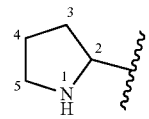

there is no —OH attached directly to carbons marked 2 and 5.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{123}$I, respectively.

Certain isotopically-labelled compounds of formula (1) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (1) can be useful for medical imaging purposes. E.g., those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

This invention provides compounds of formula (I):

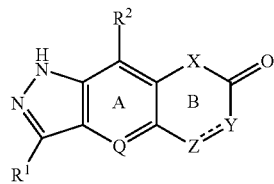

or a pharmaceutically acceptable salt thereof, wherein:

Q (in Ring A) is selected from the group consisting of: —(CR$^3$)— and N;

X (in Ring B) is selected from the group consisting of: NH and N—O;

the dashed line ( - - - ) between Y and Z in Ring B represents an optional bond;

when the optional bond is present between Y and Z (i.e., there is a double bond between Y and Z) then Y is =C(R$^4$)—, and Z is =C(R$^5$)—;

when the optional bond between Y and Z is absent (i.e., there is a single bond between Y and Z) then Y is selected from the group consisting of: —C(R$^4$R$^6$)— and —N(R$^9$)—, and Z is selected from the group consisting of: —C(=O)—, —C(R$^7$R$^8$)— and —C(R$^7$R$^8$)—C(R$^7$R$^8$)— wherein each R$^7$ and each R$^8$ is independently selected;

R$^1$ is selected from the group consisting of: H, halo, —CF$_3$, —CN, —NR$^{12}$R$^{13}$, —OR$^{10}$, —O—(R$^{10}$)—O—R$^{10}$, —O—R$^{10}$—OH, —O—R$^{11}$, (C$_1$-C$_6$)alkyl, substituted (C$_1$-C$_6$)alkyl, (C$_1$-C$_6$)alkenyl, (C$_3$-C$_7$)cycloalkyl, substituted (C$_3$-C$_7$)cycloalkyl, heteroaryl, substituted heteroaryl, heterocycloalkyl, substituted heterocycloalkyl, heterocycloalkenyl-, substituted heterocycloalkenyl, —(C$_1$-C$_6$)alkyl-O—(C$_1$-C$_6$)alkyl, (C$_6$-C$_{14}$)aryl, substituted (C$_6$-C$_{14}$)aryl, —C(O)NH(C$_1$-C$_6$)alkyl, —C(O)N((C$_1$-C$_6$)alkyl)$_2$ wherein each alkyl is independently selected, —C(O)—(C$_1$-C$_6$)alkyl-C(O)—(C$_1$-C$_6$)alkyl, —(C$_1$-C$_4$)alkyl-C(O)—O—(C$_1$-C$_4$)alkyl, —N((C$_1$-C$_6$)alkyl)-S(O)$_2$—(C$_1$-C$_6$)alkyl, —N((C$_1$-C$_6$)alkyl)-(C$_1$-C$_6$)alkyl-O—(C$_1$-C$_6$)alkyl, —C(O)NH—(C$_1$-C$_2$)alkyl-fused heteroarylheteroaryl, —C(O)NH—(C$_1$-C$_2$)alkyl-(substituted fused heteroarylheteroaryl), fused arylheterocycloalkyl, substituted fused arylheterocycloalkyl, —C(O)NH—(C$_1$-C$_2$)alkyl-(C$_3$-C$_6$)cycloalkyl-N(R$^6$)$_2$, —C(O)NH—(C$_1$-C$_2$)alkyl-(substituted (C$_3$-C$_6$)cycloalkyl)-N(R$^6$)$_2$, —C(O)NH—(C$_1$-C$_2$)alkylheterocycloalkyl, —C(O)NH—(C$_1$-C$_2$)alkyl(substituted heterocycloalkyl), —C(O)NH—(C$_1$-C$_2$)alkylheteroaryl, —C(O)NH—(C$_1$-C$_2$)alkyl(substituted heteroaryl), —C(O)NH—(C$_1$-C$_6$)alkyl-(C$_3$-C$_6$)cycloalkyl, —C(O)NH—(C$_1$-C$_6$)alkyl-(substituted (C$_3$-C$_6$)cycloalkyl), —C(O)NH—(C$_1$-C$_6$)alkyl-O—(C$_1$-C$_6$)alkyl, —C(O)NH—(C$_1$-C$_6$)alkylheterocycloalkyl, —C(O)NH—(C$_1$-C$_6$)alkyl (substituted heterocycloalkyl), —C(O)-heterocycloalkyl-S—(C$_1$-C$_6$)alkyl, —C(O)— (substituted heterocycloalkyl-S—(C$_1$-C$_6$)alkyl, —C(O)-heterocycloalkyl, —C(O)-(substituted heterocycloalkyl), fused arylheteroaryl, fused (substituted arylheteroaryl), fused heteroarylheteroaryl, fused (substituted heteroarylheteroaryl), fused heterocycloalkylheteroaryl, substituted fused heterocycloalkylheteroaryl, —(C$_1$-C$_4$)alkyl-S(O)$_2$—(C$_1$-C$_6$)alkyl, and —(C$_1$-C$_4$)alkyl-NH—(C$_1$-C$_6$)alkyl;

and wherein said substituted R$^1$ groups, other than said substituted (C$_1$-C$_6$)alkyl, are substituted with 1 to 3 substituents independently selected from the group consisting of: —(C$_1$-C$_6$)alkyl, halo, CN, —OH, —OR$^{10}$, —CF$_3$, =O, —NH$_2$, —NH(C$_1$-C$_6$)alkyl, —S(O)$_2$(C$_1$-C$_6$)alkyl, —(C$_3$-C$_6$)cycloalkyl, —((C$_1$-C$_6$)alkyl)OH, —(C$_3$-C$_6$)cycloalkyl-S—(C$_3$-C$_6$)cycloalkyl, —N((C$_1$-C$_6$)alkyl)$_2$ wherein each alkyl is independently selected, —C(O)O—(C$_1$-C$_6$)alkyl, —C(O)OH, —OCF$_3$, —C(O)NH(C$_1$-C$_6$)alkyl, heteroaryl, —(C$_1$-C$_6$)alkyl)-O—(C$_1$-C$_6$)alkyl, fused heteroarylaryl-, heterocycloalkyl, and heterocycloalkenyl;

and wherein said substituted (C$_1$-C$_6$)alkyl R$^1$ group is substituted with 1 to 3 substituents independently selected from the group consisting of: —(C$_1$-C$_6$)alkoxy, halo, CN, —OH, =O, —CF$_3$, —NH$_2$, —NH(C$_1$-C$_6$)alkyl, —S(O)$_2$(C$_1$-C$_6$)alkyl, fused heteroarylaryl-, heterocycloalkyl, and heterocycloalkenyl;

and wherein the alkyl moieties of the R$^1$ groups, other than (C$_1$-C$_6$)alkyl and substituted (C$_1$-C$_6$)alkyl, are optionally substituted with 1 to 3 substituents independently selected from the group consisting of: (C$_1$-C$_6$)alkoxy, halo, CN, —OH, =O, —CF$_3$, —NH$_2$, —NH(C$_1$-C$_6$)alkyl, —S(O)$_2$(C$_1$-C$_6$)alkyl, fused heteroarylaryl-, heterocycloalkyl, and heterocycloalkenyl;

and wherein said heteroaryl moiety of said R$^1$ groups is a 5-10 membered ring comprising 1-3 heteroatoms independently selected from the group consisting of: N, O and S, and wherein the remaining ring atoms are carbon (and wherein said heteroaryl definition applies to the heteroaryl moieties in the R$^1$ fused heteroarylheteroaryl, substituted fused heteroarylheteroaryl, fused arylheteroaryl, substituted arylheteroaryl, fused heterocycloalkylheteroaryl, substituted fused heterocycloalkylheteroaryl, and fused heteroarylaryl-groups);

and wherein said heterocycloalkyl moiety of said R$^1$ groups is a 3-10 membered ring comprising 1-3 heteroatoms independently selected from the group consisting of: N, O and S, and wherein the remaining ring atoms are carbon (and wherein said heterocycloalkyl definition applies to the heterocycloalkyl moieties in the R$^1$ fused heterocycloalkylheteroaryl and substituted fused heterocycloalkylheteroaryl groups);

and wherein said heterocycloalkenyl moiety of said R$^1$ groups is a 3-10 membered ring comprising 1-2 double bonds, and 1-3 heteroatoms independently selected from the group consisting of: N, O and S, and the remaining ring atoms are carbon;

and wherein said fused heteroarylheteroaryl moiety of said R$^1$ groups is a heteroaryl, as defined above, fused to a heteroaryl, as defined above, such that there are two ring atoms in common with each heteroaryl, and wherein the total ring atoms are 8-11, and wherein said fused ring comprises 1-4 heteroatoms independently selected from the group consisting of: O, N and S, and wherein the remaining ring atoms are carbon;

and wherein said fused heterocycloalkylheteroaryl moiety of said R$^1$ groups comprises a heteroaryl, as defined above, fused to a heterocycloalkyl, as defined above, such that there are two ring atoms in common with the heterocycloalkyl and heteroaryl, wherein said heterocycloalkyl is bound to the rest of the molecule, and wherein said heterocycloalkyl moiety comprises 1-3 heteroatoms independently selected from the group consisting of: N, O and S, and wherein said heteroaryl moiety comprises 1-3 heteroatoms independently selected from the group consisting of: N, S, and O;

and wherein said fused arylheteroaryl moiety of said R$^1$ groups comprises a C$_6$-C$_{10}$ aryl fused to a heteroaryl, as defined above, wherein the aryl and the heteroaryl have 2 ring atoms in common;

R$^2$ is selected from the group consisting of: H, halo, —NH$_2$, —OH and —(C$_1$-C$_3$)alkyl;

R³ is selected from the group consisting of: H, halo, ($C_1$-$C_6$alkyl), and ($C_1$-$C_6$alkyl) substituted with 1-2 —OH groups, —($C_3$-$C_6$ cycloalkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, and —($C_1$-$C_6$alkyl)-heterocycloalkyl (wherein said heterocycloalkyl is as defined above for $R^1$);

R⁴ is selected from the group consisting of: H, halo, ($C_6$-$C_{14}$)aryl($C_1$-$C_6$)-alkyl-, substituted ($C_6$-$C_{14}$)aryl($C_1$-$C_6$)alkyl-, heteroaryl, substituted heteroaryl, heteroaryl($C_1$-$C_6$)alkyl-, substituted heteroaryl($C_1$-$C_6$)alkyl-, fused ($C_3$-$C_7$)cycloalkyl($C_6$-$C_{14}$)aryl, substituted fused ($C_3$-$C_7$)cycloalkyl($C_6$-$C_{14}$)aryl, fused heterocycloalkyl($C_6$-$C_{14}$)aryl, substituted and fused heterocycloalkyl($C_6$-$C_{14}$)aryl; wherein said substituted R⁴ moieties are substituted with 1-3 substitutents independently selected from the group consisting of: halo, ($C_1$-$C_6$)alkyl, and ($C_1$-$C_6$)alkyl-O—($C_1$-$C_6$)alkyl; and wherein said heteroaryl moiety and said heterocycloalkyl moiety is as defined above in $R^1$;

each $R^6$, $R^7$, and $R^8$ is independently selected from the group consisting of: H, halo, ($C_6$-$C_{14}$)aryl($C_1$-$C_6$)-alkyl-, substituted ($C_6$-$C_{14}$)aryl($C_1$-$C_6$)alkyl-, heteroaryl, substituted heteroaryl, heteroaryl($C_1$-$C_6$)alkyl-, substituted heteroaryl($C_1$-$C_6$)alkyl-, fused ($C_3$-$C_7$)cycloalkyl($C_6$-$C_{14}$)aryl, substituted fused ($C_3$-$C_7$)cycloalkyl($C_6$-$C_{14}$)aryl, fused heterocycloalkyl($C_6$-$C_{14}$)aryl, and substituted fused heterocycloalkyl($C_6$-$C_{14}$)aryl; wherein said substituted $R^6$, $R^7$, $R^8$ moieties are substituted with 1-3 substitutents independently selected from the group consisting of: halo, ($C_1$-$C_6$)alkyl, and ($C_1$-$C_6$)alkyl-O—($C_1$-$C_6$)alkyl; and wherein said heteroaryl moiety and said heterocycloalkyl moiety is as defined above in $R^1$;

R⁹ is selected from the group consisting of: H, ($C_6$-$C_{10}$)aryl($C_1$-$C_6$)alkyl, substituted ($C_6$-$C_{14}$)aryl($C_1$-$C_6$)alkyl-, heteroaryl, substituted heteroaryl, heteroaryl($C_1$-$C_6$)alkyl-, substituted heteroaryl($C_1$-$C_6$)alkyl-, fused ($C_3$-$C_7$)cycloalkyl($C_6$-$C_{14}$)aryl, substituted fused ($C_3$-$C_7$)cycloalkyl($C_6$-$C_{14}$)aryl, fused heterocycloalkyl($C_6$-$C_{14}$)aryl, and substituted fused heterocycloalkyl($C_6$-$C_{14}$)aryl; wherein said substituted R⁹ moieties are substituted with 1-3 substitutents independently selected from the group consisting of: halo, OH, CN, CF$_3$, ($C_1$-$C_6$)alkyl, and ($C_1$-$C_6$)alkyl-O—($C_1$-$C_6$)alkyl; and wherein said heteroaryl moiety and said heterocycloalkyl moiety is as defined above for $R^1$;

each $R^{10}$ is independently selected from the group consisting of: $C_1$-$C_6$alkyl and heterocycloalkyl having 5-6 ring atoms comprising 1-2 oxygen atoms;

$R^{11}$ is a 4-7 membered heterocycloalkyl ring comprising 1-3 heteroatoms independently selected from the group consisting of: O, S and N; and $R^{12}$ and $R^{13}$ are independently selected from the group consisting of: H, ($C_1$-$C_6$)alkyl, —C(O)O$R^{10}$, and —C(O)$R^{10}$, said alkyl group optionally substituted with 1-4 halo substitutents independently selected from the group consisting of: halo.

Embodiments of this invention include compounds wherein the $R^1$ heteroaryl moiety is a 5-10 membered ring comprising 1-3 heteroatoms independently selected from the group consisting of: N, O and S, and wherein the remaining ring atoms are carbon. Embodiments of this invention also include compounds in these embodiments include compounds wherein the $R^1$ heteroaryl moiety is a 5-7 membered ring comprising 1-3 heteroatoms independently selected from the group consisting of: N, O and S, and wherein the remaining ring atoms are carbon. Embodiments of this invention also include compounds wherein the $R^1$ heteroaryl moiety is a 5-6 membered ring comprising 1-3 heteroatoms independently selected from the group consisting of: N, O and S, and wherein the remaining ring atoms are carbon. Embodiments of this invention include compounds wherein the definitions of the $R^1$ heteroaryl moiety in this paragraph applies to the heteroaryl moieties in the $R^1$ fused heteroarylheteroaryl, substituted fused heteroarylheteroaryl, fused arylheteroaryl, substituted arylheteroaryl, fused heterocycloalkylheteroaryl, substituted fused heterocycloalkylheteroaryl, and fused heteroarylaryl- groups.

Embodiments of this invention include compounds wherein the $R^1$ heterocycloalkyl moiety is a 3-10 membered ring comprising 1-3 heteroatoms independently selected from the group consisting of: N, O and S, and wherein the remaining ring atoms are carbon. Embodiments of this invention include compounds wherein the $R^1$ heterocycloalkyl moiety is a 4-8 membered ring comprising 1-3 heteroatoms independently selected from the group consisting of: N, O and S, and wherein the remaining ring atoms are carbon. Embodiments of this invention include compounds wherein the definitions of the $R^1$ heterocycloalkyl moiety in this paragraph applies to the heterocycloalkyl moieties in the $R^1$ fused heterocycloalkylheteroaryl and substituted fused heterocycloalkylheteroaryl groups.

Embodiments of this invention include compounds wherein the $R^1$ heterocycloalkenyl moiety is a 3-10 membered ring comprising 1-2 double bonds (e.g., one double bond), and 1-3 heteroatoms independently selected from the group consisting of: N, O and S, and the remaining ring atoms are carbon. Embodiments of this invention include compounds wherein the $R^1$ heterocycloalkenyl moiety is a 4-8 membered ring comprising 1-2 double bonds (e.g., one double bond), and 1-3 heteroatoms independently selected from the group consisting of: N, O and S, and the remaining ring atoms are carbon. Embodiments of this invention include compounds wherein the $R^1$ heterocycloalkenyl moiety is a 4-6 membered ring comprising 1-2 double bonds (e.g., one double bond), and 1-3 heteroatoms independently selected from the group consisting of: N, O and S, and the remaining ring atoms are carbon.

Embodiments of this invention include compounds wherein the $R^1$ fused heteroarylheteroaryl is a heteroaryl fused to a heteroaryl such that there are two ring atoms in common with each heteroaryl, and wherein the total ring atoms are 8-11, and wherein said fused ring comprises 1-4 heteroatoms independently selected from the group consisting of: O, N and S, and wherein the remaining ring atoms are carbon. In these embodiments each heteroaryl is independently selected from the group consisting of: 5-10 membered heteroaryl rings comprising 1-3 heteroatoms independently selected from the group consisting of: N, O and S, and wherein the remaining ring atoms are carbon. Or, in these embodiments each heteroaryl is independently selected from the group consisting of: 5-7 membered heteroaryl rings comprising 1-3 heteroatoms independently selected from the group consisting of: N, O and S, and wherein the remaining ring atoms are carbon. Or, in these embodiments each heteroaryl is independently selected from the group consisting of: 5-6 membered heteroaryl rings comprising 1-3 heteroatoms independently selected from the group consisting of: N, O and S, and wherein the remaining ring atoms are carbon.

Embodiments of this invention include compounds wherein the $R^1$ fused heterocycloalkylheteroaryl comprises a heteroaryl, as defined above, fused to a heterocycloalkyl, as defined above, such that there are two ring atoms in common with the heterocycloalkyl and heteroaryl. Embodiments of this invention also include compounds wherein the $R^1$ fused heterocycloalkylheteroaryl comprises a 5-6 membered heteroaryl, as defined above, fused to a 4-8 membered heterocycloalkyl, as defined above, such that there are two ring atoms in common with the heterocycloalkyl and heteroaryl. Embodiments of this invention also include compounds wherein the $R^1$ fused heterocycloalkylheteroaryl comprises a 5-6 membered heteroaryl ring, as defined above, wherein the heteroatoms in said heteroaryl are independently selected from the group consisting of N and S, and wherein said heteroaryl is fused to a 4-8 membered heterocycloalkyl, as defined above, wherein the heteroatom, or heteroatoms, in said heterocycloalkyl are nitrogen, such that there are two ring atoms in common with the heterocycloalkyl and heteroaryl.

Embodiments of this invention include compounds wherein the $R^1$ fused arylheteroaryl moiety comprises a $C_6$-$C_{10}$ aryl (e.g., phenyl) fused to a heteroaryl, as defined above, wherein the aryl and the heteroaryl have 2 ring atoms in common. Embodiments of this invention also include compounds wherein the $R^1$ fused arylheteroaryl moiety comprises a phenyl fused to a heteroaryl, as defined above, wherein the phenyl and the heteroaryl have 2 ring atoms in common.

Embodiments of this invention include compounds wherein the $R^1$ fused heterocycloalkylaryl moiety is a $C_6$-$C_{10}$ aryl fused to a heterocycloalkyl, as defined above. In one embodiment the $R^1$ moiety is a phenyl fused to heterocycloalkyl. Examples of the heterocycloalkyl moiety in these embodiments include 5-6 membered rings comprising 1-2 heteroatoms, such as for example 6 membered heterocycloalkyl rings comprising 1-2 heteroatoms, and in other examples a 6 membered ring comprising 2 heteroatoms, and in other examples a 6 membered ring comprising two oxygen atoms.

In one embodiment the $R^1$ halo moiety is I. In one embodiment, when the $R^1$ groups other than $(C_1$-$C_6)$alkyl are substituted with halo, said halo is F. In one embodiment, when the $R^1$ groups other than $(C_1$-$C_6)$alkyl are substituted with halo, said halo is Cl. In one embodiment, when the $R^1$ groups other than $(C_1$-$C_6)$alkyl are substituted with —$OR^{10}$ said —$OR^{10}$ is $(C_1$-$C_6)$alkoxy. In one embodiment the $R^1$ heteroaryl moiety is a 5-7 membered ring. In one embodiment the $R^1$ heteroaryl moiety is a 5-6 membered ring. In one embodiment the $R^1$ heterocycloalkyl moiety is a 4-8 membered ring. In one embodiment the $R^1$ heterocycloalkenyl moiety has one double bond. In one embodiment the $R^1$ heterocycloalkenyl moiety is a 4-8 membered ring. In one embodiment the $R^1$ heterocycloalkenyl moiety is a 4-6 membered ring. In one embodiment the $R^1$ fused heterocycloalkylheteroaryl moiety comprises a 5-6 membered heteroaryl fused to a 4-8 membered heterocycloalkyl. In one embodiment the $R^1$ fused heterocycloalkylheteroaryl moiety comprises a 5-6 membered heteroaryl, fused to a 4-8 membered heterocycloalkyl, wherein said heterocycloalkyl comprises 1-3 nitrogen atoms, and wherein said heteroaryl comprises 1-3 heteroatoms independently selected from the group consisting of N and S. In one embodiment the $R^1$ arylheteroaryl moiety is a phenyl fused to a heteroaryl.

In one embodiment the $R^3$ ($C_1$-$C_6$alkyl) substituted with 1-2 —OH groups moiety is —$(C_1$-$C_6$alkyl)-OH, and in another embodiment —$CH_2OH$.

In one embodiment the $R^4$ halo moiety is Br. In one embodiment, when the $R^4$ moiety is substituted with halo, said halo is F. In one embodiment, when the $R^4$ moiety is substituted with $(C_1$-$C_6)$alkyl-O—$(C_1$-$C_6)$alkyl, said $(C_1$-$C_6)$alkyl-O—$(C_1$-$C_6)$alkyl is $(C_1$-$C_2)$alkyl-O—$(C_1$-$C_2)$alkyl.

In one embodiment the $R^6$, $R^7$, and $R^8$ halo moiety is Br.

In one embodiment, when the $R^6$, $R^7$, and $R^8$ moieties are substituted with halo, said halo is F. In one embodiment, when the $R^6$, $R^7$, and $R^8$ moieties are substituted with $(C_1$-$C_6)$alkyl-O—$(C_1$-$C_6)$alkyl, said $(C_1$-$C_6)$alkyl-O—$(C_1$-$C_6)$alkyl is $(C_1$-$C_2)$alkyl-O—$(C_1$-$C_2)$alkyl.

In one embodiment, when the $R^9$ moiety is substituted with halo, said halo is F. In another embodiment, when the $R^9$ moiety is substituted with $(C_1$-$C_6)$alkyl-O—$(C_1$-$C_6)$alkyl, said $(C_1$-$C_6)$alkyl-O—$(C_1$-$C_6)$alkyl is $(C_1$-$C_2)$alkyl-O—$(C_1$-$C_2)$alkyl.

In one embodiment the heteroatoms in said $R^{11}$ heterocycloalkyl ring are oxygen.

In one embodiment, when said $(C_1$-$C_6)$alkyl moiety of said $R^{12}$ or $R^{13}$ moiety is substituted with halo, said halo is F.

In one embodiment Q is —$(CR^3)$—.

In another embodiment Q is N.

The following embodiments are numbered for ease of reference.

In Embodiment (1) the $(C_6$-$C_{14})$aryl moities in formula (I) are phenyl.

In Embodiment (2) X is N. In Embodiment (3) X is N—O.

In Embodiment (4) the optional bond is present (i.e., there is a double bond between Y and Z) and Y is =$C(R^4)$— and Z is =$C(R^5)$—.

In Embodiment (5) the optional bond is absent (i.e., there is a single bond between Y and Z) and Y is —$C(R^4R^6)$— and Z is —$C(R^7R^8)$—.

In Embodiment (6) the optional bond is absent (i.e., there is a single bond between Y and Z) Y is —$C(R^4R^6)$— wherein $R^6$ is H, and Z is —$C(R^7R^8)$— wherein $R^7$ and $R^8$ are each H.

In Embodiment (7) the optional bond is absent (i.e., there is a single bond between Y and Z) and Y is —$C(R^4R^6)$— and Z is —$C(R^7R^8)$—$C(R^7R^8)$—.

In Embodiment (8) the optional bond is absent (i.e., there is a single bond between Y and Z), Y is —$C(R^4R^6)$— wherein $R^6$ is H, and Z is —$C(R^7R^8)$—$C(R^7R^8)$— wherein each $R^7$ and each $R^8$ is H.

In Embodiment (9) the optional bond is absent (i.e., there is a single bond between Y and Z), and Z is —(C=O)—.

In Embodiment (10) the optional bond is absent (i.e., there is a single bond between Y and Z), Y is —$C(R^4R^6)$— wherein $R^6$ is H, and Z is —(C=O)—.

In Embodiment (11) the optional bond is absent (i.e., there is a single bond between Y and Z) and Y is —$N(R^9)$— and Z is —$C(R^7R^8)$—.

In Embodiment (12) the optional bond is absent (i.e., there is a single bond between Y and Z), Y is —$N(R^9)$— and Z is —$C(R^7R^8)$— wherein $R^7$ and $R^8$ are each H.

In Embodiment (13) the optional bond is absent (i.e., there is a single bond between Y and Z), Y is —$N(R^9)$— and Z is —$C(R^7R^8)$—$C(R^7R^8)$—.

In Embodiment (14) the optional bond is absent (i.e., there is a single bond between Y and Z), Y is —$N(R^9)$— and Z is —$C(R^7R^8)$—$C(R^7R^8)$— wherein each $R^7$ and $R^8$ is H.

In Embodiment (15) the optional bond is absent (i.e., there is a single bond between Y and Z), Y is —$N(R^9)$— and Z is —C(=O)—.

In Embodiment (16) Ring B is selected from the group consisting of:

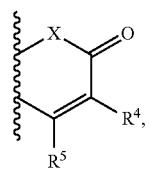 (a1)

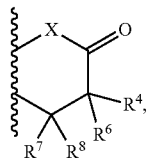 (b1)

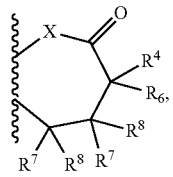 (c1)

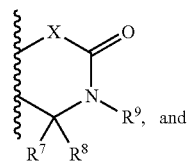 (d1)

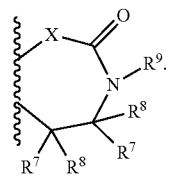 (e1)

In Embodiment (17) Ring B is selected from the group consisting of:

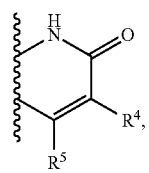 (a2)

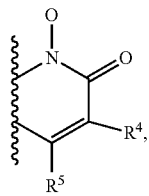 (a3)

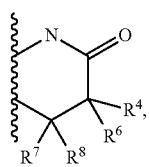 (b2)

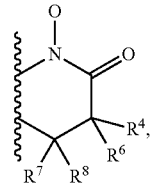 (b3)

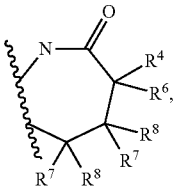 (c2)

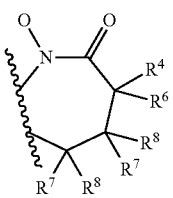 (c3)

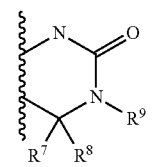 (d2)

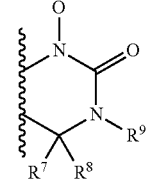 (d3)

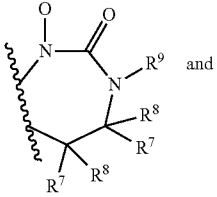 (e2)

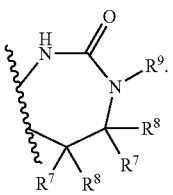 (e3)

In Embodiment (18) Ring B is selected from the group consisting of: (a2), (b3), (c2), (d2), (e2) and (e3).
In Embodiment (19) $R^2$ is H.
In Embodiment (20) $R^2$ is halo.
In Embodiment (21) Q is —(CR$^3$)— and $R^3$ is H.
In Embodiment (22) Q is —(CR$^3$)— and $R^3$ is —CH$_2$OH.
In Embodiment (23) $R^5$ is H.
In Embodiment (24) Ring B is (a2). In Embodiment (25) Ring B is (a2) and $R^5$ is H.

In Embodiment (26) Ring B is (a3). In Embodiment (27) Ring B is (a3) and $R^5$ is H.

In Embodiment (28) Ring B is (b2). In Embodiment (29) Ring B is (b2) and $R^6$ is H. In Embodiment (30) Ring B is (b2), $R^6$ is H, $R^7$ is H, and $R^8$ is H.

In Embodiment (31) Ring B is (b3). In Embodiment (32) Ring B is (b3) and $R^6$ is H. In Embodiment (33) Ring B is (b3), $R^6$ is H, $R^7$ is H, and $R^8$ is H.

In Embodiment (34) Ring B is (c2). In Embodiment (35) B is (c2) and $R^6$ is H. In Embodiment (36) Ring B is (c2), $R^6$ is H, each $R^7$ is H, and each $R^8$ is H.

In Embodiment (37) Ring B is (c3). In Embodiment (38) Ring B is (c3) and $R^6$ is H. In Embodiment (39) Ring B is (c3), $R^6$ is H, each $R^7$ is H, and each $R^8$ is H.

In Embodiment (40) Ring B is (d2). In Embodiment (41) Ring B is (d2) and $R^7$ is H, and $R^8$ is H.

In Embodiment (42) Ring B is (d3). In Embodiment (43) Ring B is (d3) and $R^7$ is H, and $R^8$ is H.

In Embodiment (44) Ring B is (e2). In Embodiment (45) Ring B is (e2), each $R^7$ is H, and each $R^8$ is H.

In Embodiment (46) Ring B is (e3). In Embodiment (47) Ring B is (e3), each $R^7$ is H, and each $R^8$ is H.

In Embodiment (48) $R^1$ is selected from the group consisting of: H, halo, —$NR^{12}R^{13}$, —$OR^{10}$, —O—($R^{10}$)—O—$R^{10}$, —O—$R^{10}$—OH, ($C_3$-$C_7$)cycloalkyl, substituted ($C_3$-$C_7$)cycloalkyl, heterocycloalkyl, substituted heterocycloalkyl, —$OR^{11}$, heteroaryl, substituted heteroaryl, fused arylheteroaryl, and fused (substituted arylheteroaryl). In one example the ($C_3$-$C_7$)cycloalkyl moiety in this embodiment is ($C_3$-$C_6$)cycloalkyl, and in another example ($C_3$-$0_5$)cycloalkyl. In one example the substituted ($C_3$-$C_7$)cycloalkyl moiety in this embodiment is substituted ($C_3$-$C_6$)cycloalkyl, and in another example substituted ($C_3$-$C_5$)cycloalkyl.

In Embodiment (49) $R^1$ is selected from the group consisting of: H, halo, —$NR^{12}R^{13}$, —$OR^{10}$, —O—($R^{10}$)—O—$R^{10}$, —O—$R^{10}$—OH, ($C_3$-$C_7$)cycloalkyl, heterocycloalkyl, substituted heterocycloalkyl, —$OR^{11}$, heteroaryl, substituted heteroaryl, fused arylheteroaryl, and fused (substituted arylheteroaryl). In one example the ($C_3$-$C_7$)cycloalkyl moiety in this embodiment is ($C_3$-$C_6$)cycloalkyl, and in another example ($C_3$-$C_5$)cycloalkyl.

In Embodiment (50) $R^1$ is selected from the group consisting of: H, I, Br, —$NH_2$, —$NHCH_2CH_3$, —$NHCH(CH_3)C(F)_3$, —$NHC(O)OCH_3$, —$NHC(O)CH_3$, —$OCH_3$, —$OCH_2CH_2OCH_3$, —$OCH_2CH_2OH$, —$(CH_2)_3$—O—$CH_3$, $CH_3CH_2CH_2$—, cyclopropyl, $CH_3CH=CH$—, (f1)

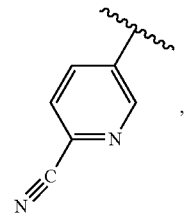

(f2)

(f3)

-continued (f4)

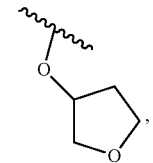

(f5)

(f6)

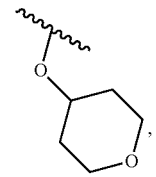

(f7)

(f8)

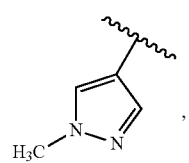

(f9)

(f10)

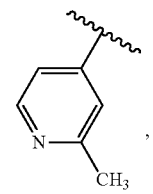

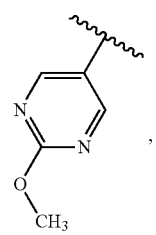

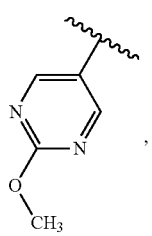

(f11)

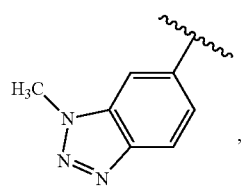

(f12) 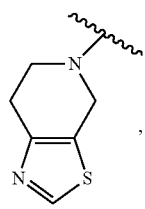
(f13) 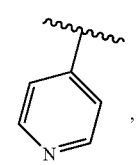
(f14) 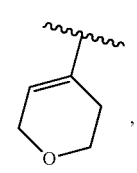
(f15) 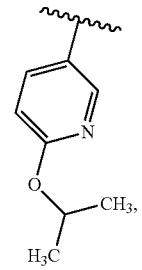
(f16) 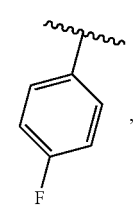
(f17) 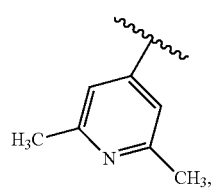
(f18) 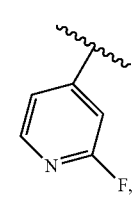
(f19) 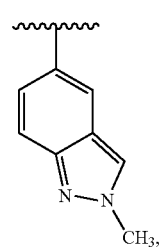
(f20) 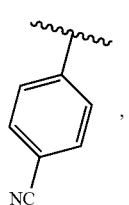
(f21) 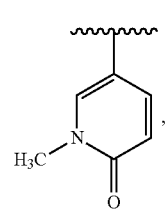
(f22) 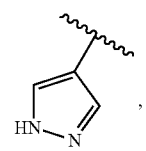
(f23) 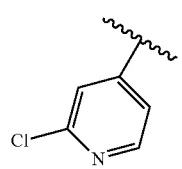
(f24) 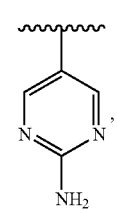
(f25) 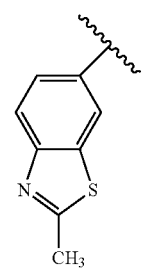
(f26) 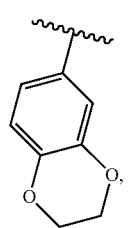

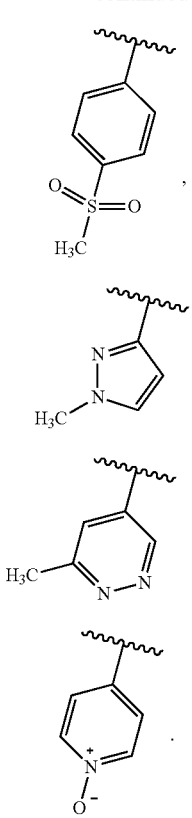

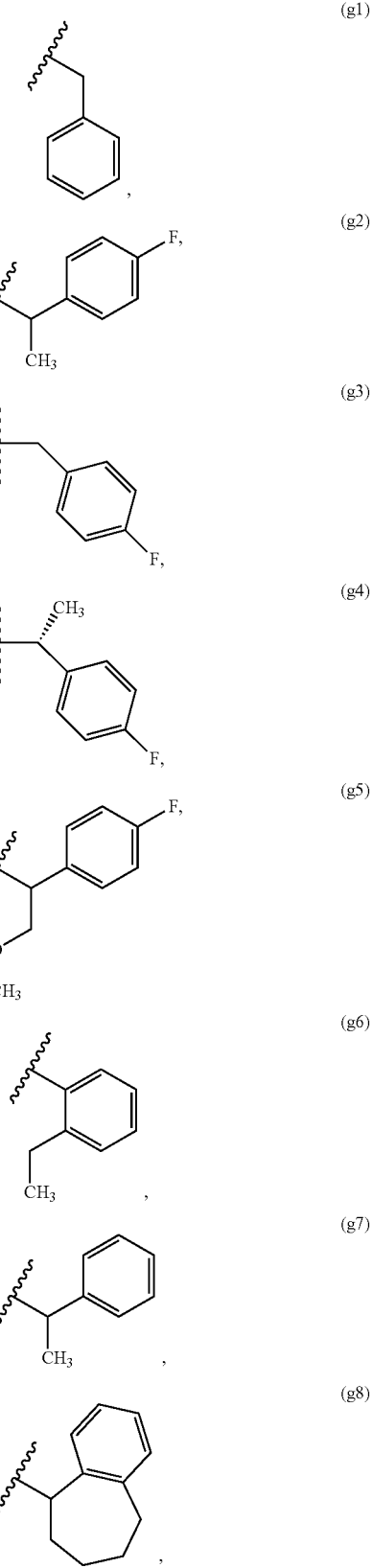

In Embodiment (93) R⁴ is selected from the group consisting of: H, Br,

In Embodiment (51) $R^1$ is H. In embodiment (52) $R^1$ is —NH₂. In embodiment (53) $R^1$ is CH₃CH₂CH₂—. In embodiment (54) $R^1$ is CH₃CH=CH—. In embodiment (55) $R^1$ is —N(H)CH₂CH₃. In Embodiment (56) $R^1$ is —N(H)CH(CH₃)C(F)₃. In Embodiment (57) $R^1$ is —N(H)C(O)OCH₃. In Embodiment (58) $R^1$ is —N(H)C(O)CH₃. In Embodiment (59) $R^1$ is —OCH₃. In Embodiment (60) $R^1$ is —OCH₂CH₂OCH₃. In Embodiment (61) $R^1$ is —OCH₂CH₂OH. In Embodiment (62) $R^1$ is (f1). In Embodiment (63) $R^1$ is (f2). In Embodiment (64) $R^1$ is (f3). In Embodiment (65) $R^1$ is (f4). In Embodiment (66) $R^1$ is (f5). In Embodiment (67) $R^1$ is (f6). In Embodiment (68) $R^1$ is (f7). In Embodiment (69) $R^1$ is (f8). In Embodiment (70) $R^1$ is (f9). In Embodiment (71) $R^1$ is (f10). In Embodiment (72) $R^1$ is (f11). In Embodiment (73) $R^1$ is (f12). In Embodiment (74) $R^1$ is (f13). In Embodiment (75) $R^1$ is (f14). In Embodiment (76) $R^1$ is (f15). In Embodiment (77) $R^1$ is (f16). In Embodiment (78) $R^1$ is (f17). In Embodiment (79) $R^1$ is (f18). In Embodiment (80) $R^1$ is (f19). In Embodiment (81) $R^1$ is (f20). In Embodiment (82) $R^1$ is (f21). In Embodiment (83) $R^1$ is (f22). In Embodiment (84) $R^1$ is (f23). In Embodiment (85) $R^1$ is (f24). In Embodiment (86) $R^1$ is (f25). In Embodiment (87) $R^1$ is (f26). In Embodiment (88) $R^1$ is (f27). In Embodiment (89) $R^1$ is (f28). In Embodiment (90) $R^1$ is (f29). In Embodiment (91) $R^1$ is (f30).

In Embodiment (92) $R^4$ is selected from the group consisting of: H, halo, heteroaryl, substituted heteroaryl, pyridyl (C₁-C₂)alkyl-), substituted pyridyl(C₁-C₂)alkyl-), phenyl-(C₁-C₃)alkyl-), substituted phenyl-(C₁-C₃)alkyl-), a fused (C₅-C₇)cycloalkylphenyl, a fused substituted (C₅-C₇)cycloalkylphenyl, a fused (5-7 membered)-heterocycloalkylphenyl, and a fused substituted (5-7 membered)heterocycloalkylphenyl.

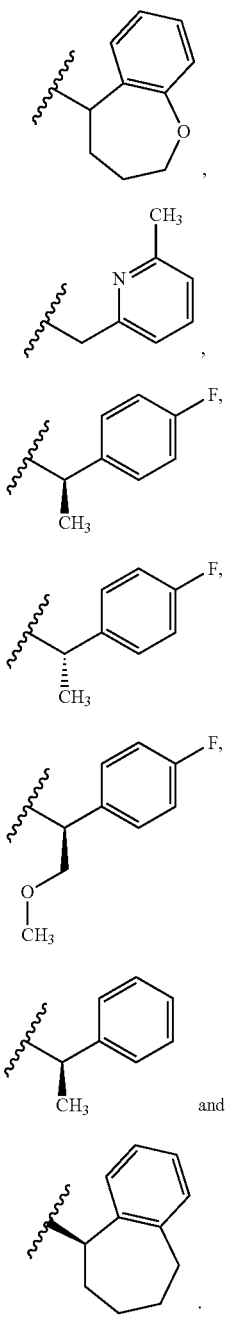

In Embodiment (94) R⁴ is H. In another embodiment R⁴ is Br. In Embodiment (95) R⁴ is (g1). In Embodiment (96) R⁴ is (g2). In Embodiment (97) R⁴ is (g3). In Embodiment (98) R⁴ is (g4). In Embodiment (99) R⁴ is (g5). In Embodiment (100) R⁴ is (g6). In Embodiment (101) R⁴ is (g7). In Embodiment (102) R⁴ is (g8). In Embodiment (103) R⁴ is (g9). In Embodiment (104) t R⁴ is (g10). In Embodiment (105) R⁴ is (g11). In Embodiment (106) R⁴ is (g12). In Embodiment (107) R⁴ is (g13). In Embodiment (108) R⁴ is (g14). In Embodiment (109) R⁴ is (g15).

In Embodiment (110) R⁹ is selected from the group consisting of: H, halo, heteroaryl, substituted heteroaryl, pyridyl($C_1$-$C_2$)alkyl-), substituted pyridyl($C_1$-$C_2$)alkyl-), phenyl-($C_1$-$C_3$)alkyl-), substituted phenyl-($C_1$-$C_3$)alkyl-), a fused ($C_5$-$C_7$)cycloalkylphenyl, a fused substituted ($C_5$-$C_7$) cycloalkylphenyl), a fused (5-7 membered)-heterocycloalkylphenyl), and a fused substituted (5-7 membered) heterocycloalkylphenyl.

In Embodiment (111) R⁹ is selected from the group consisting of: H, (g1), (g2), (g3), (g4), (g5), (g6), (g7), (g8), (g9), (g10), (g11), (g12), (g13), (g14), and (g15).

In Embodiment (112) R⁹ is H. In Embodiment (113) R⁹ is (g1). In Embodiment (114) R⁹ is (g2). In Embodiment (115) R⁹ is (g3). In Embodiment (116) R⁹ is (g4). In Embodiment (117) R⁹ is (g5). In Embodiment (118) R⁹ is (g6). In Embodiment (119) R⁹ is (g7). In Embodiment (120) R⁹ is (g8). In Embodiment (121) R⁹ is (g9). In Embodiment (122) R⁹ is (g10). In Embodiment (123) R⁹ is (g11). In Embodiment (124) R⁹ is (g12). In Embodiment (125) R⁹ is (g13). In Embodiment (126) R⁹ is (g14). In Embodiment (127) R⁹ is (g15).

In Embodiment (113):
(1) R¹ is selected from the group consisting of: H, I, —NH₂, —NHCH₂CH₃, —NHCH(CH₃)C(F)₃, —NHC(O)OCH₃, —NHC(O)CH₃, —OCH₃, —OCH₂CH₂OCH₃, —OCH₂CH₂OH, (f1), (f2), (f3), (f4), (f5), (f6), (f7), (f8), (f9), (f10), (f11), and (f12);
(2) R⁴ is selected from the group consisting of: H, Br, (g1), (g2), (g3), (g4), (g5), (g6), (g7), (g8), (g9), (g10), (g11), (g12), (g13), (g14), and (g15); and
(3) R⁹ is selected from the group consisting of: H, (g1), (g2), (g3), (g4), (g5), (g6), (g7), (g8), (g9), (g10), (g11), (g12), (g13), (g14), and (g15).

In Embodiment (114):
(1) R¹ is selected from the group consisting of: H, I, —NH₂, —NHCH₂CH₃, —NHCH(CH₃)C(F)₃, —NHC(O)OCH₃, —NHC(O)CH₃, —OCH₃, —OCH₂CH₂OCH₃, —OCH₂CH₂OH, (f1), (f2), (f3), (f4), (f5), (f6), (f7), (f8), (f9), (f10), (f11), and (f12);
(2) R² is selected from the group consisting of: H and halo;
(3) R⁴ is selected from the group consisting of: H, Br, (g1), (g2), (g3), (g4), (g5), (g6), (g7), (g8), (g9), (g10), (g11), (g12), (g13), (g14), and (g15); and
(4) R⁵ is H; and
(5) R⁹ is selected from the group consisting of: H, (g1), (g2), (g3), (g4), (g5), (g6), (g7), (g8), (g9), (g10), (g11), (g12), (g13), (g14), and (g15).

In Embodiment (115):
(1) R¹ is selected from the group consisting of: H, I, —NH₂, —NHCH₂CH₃, —NHCH(CH₃)C(F)₃, —NHC(O)OCH₃, —NHC(O)CH₃, —OCH₃, —OCH₂CH₂OCH₃, —OCH₂CH₂OH, (f1), (f2), (f3), (f4), (f5), (f6), (f7), (f8), (f9), (f10), (f11), and (f12);
(2) R² is selected from the group consisting of: H and halo;
(3) Q is —(CR³)— and R³ is H;
(4) R⁴ is selected from the group consisting of: H, Br, (g1), (g2), (g3), (g4), (g5), (g6), (g7), (g8), (g9), (g10), (g11), (g12), (g13), (g14), and (g15); and
(5) R⁵ is H; and
(6) R⁹ is selected from the group consisting of: H, (g1), (g2), (g3), (g4), (g5), (g6), (g7), (g8), (g9), (g10), (g11), (g12), (g13), (g14), and (g15).

In Embodiment (116):
(1) Ring B is selected from the group consisting of: (a2), (a3), (b2), (b3), (c2), (c3), (d2), (d3), (e2), and (e3);
(2) R¹ is selected from the group consisting of: H, I, —NH₂, —NHCH₂CH₃, —NHCH(CH₃)C(F)₃, —NHC(O)

OCH₃, —NHC(O)CH₃, —OCH₃, —OCH₂CH₂OCH₃, —OCH₂CH₂OH, (f1), (f2), (f3), (f4), (f5), (f6), (f7), (f8), (f9), (f10), (f11), and (f12);
(3) R² is selected from the group consisting of: H and halo;
(4) Q is —(CR³)— and R³ is H;
(5) R⁴ is selected from the group consisting of: H, Br, (g1), (g2), (g3), (g4), (g5), (g6), (g7), (g8), (g9), (g10), (g11), (g12), (g13), (g14), and (g15);
(6) R⁵ is H; and
(7) R⁹ is selected from the group consisting of: H, (g1), (g2), (g3), (g4), (g5), (g6), (g7), (g8), (g9), (g10), (g11), (g12), (g13), (g14), and (g15).

In Embodiment (117):
(1) Ring B is selected from the group consisting of: (a2), (a3), (b2), (b3), (c2), (c3), (d2), (d3), (e2), and (e3);
(2) R¹ is selected from the group consisting of: H, I, —NH₂, —NHCH₂CH₃, —NHCH(CH₃)C(F)₃, —NHC(O)OCH₃, —NHC(O)CH₃, —OCH₃, —OCH₂CH₂OCH₃, —OCH₂CH₂OH, (f1), (f2), (f3), (f4), (f5), (f6), (f7), (f8), (f9), (f10), (f11), and (f12);
(3) R² is selected from the group consisting of: H and halo;
(4) Q is —(CR³)— and R³ is H;
(5) R⁴ is selected from the group consisting of: H, Br, (g1), (g2), (g3), (g4), (g5), (g6), (g7), (g8), (g9), (g10), (g11), (g12), (g13), (g14), and (g15);
(6) R⁵, R⁶, R⁷, and R⁸ are H; and
(7) R⁹ is selected from the group consisting of: H, (g1), (g2), (g3), (g4), (g5), (g6), (g7), (g8), (g9), (g10), (g11), (g12), (g13), (g14), and (g15).

In Embodiment (118):
(1) Ring B is selected from the group consisting of: (a2), (b3), (c2), (d2), (e2), and (e3);
(2) R¹ is selected from the group consisting of: H, I, —NH₂, —NHCH₂CH₃, —NHCH(CH₃)C(F)₃, —NHC(O)OCH₃, —NHC(O)CH₃, —OCH₃, —OCH₂CH₂OCH₃, —OCH₂CH₂OH, (f1), (f2), (f3), (f4), (f5), (f6), (f7), (f8), (f9), (f10), (f11), and (f12);
(3) R² is selected from the group consisting of: H and halo;
(4) Q is —(CR³)— and R³ is H;
(5) R⁴ is selected from the group consisting of: H, Br, (g1), (g2), (g3), (g4), (g5), (g6), (g7), (g8), (g9), (g10), (g11), (g12), (g13), (g14), and (g15);
(6) R⁵ is H; and
(7) R⁹ is selected from the group consisting of: H, (g1), (g2), (g3), (g4), (g5), (g6), (g7), (g8), (g9), (g10), (g11), (g12), (g13), (g14), and (g15).

In Embodiment (119):
(1) Ring B is selected from the group consisting of: (a2), (b3), (c2), (d2), (e2), and (e3);
(2) R¹ is selected from the group consisting of: H, I, —NH₂, —NHCH₂CH₃, —NHCH(CH₃)C(F)₃, —NHC(O)OCH₃, —NHC(O)CH₃, —OCH₃, —OCH₂CH₂OCH₃, —OCH₂CH₂OH, (f1), (f2), (f3), (f4), (f5), (f6), (f7), (f8), (f9), (f10), (f11), and (f12);
(3) R² is selected from the group consisting of: H and halo;
(4) Q is —(CR³)— and R³ is H;
(5) R⁴ is selected from the group consisting of: H, Br, (g1), (g2), (g3), (g4), (g5), (g6), (g7), (g8), (g9), (g10), (g11), (g12), (g13), (g14), and (g15);
(6) R⁵, R⁶, R⁷, and R⁸ are H; and
(7) R⁹ is selected from the group consisting of: H, (g1), (g2), (g3), (g4), (g5), (g6), (g7), (g8), (g9), (g10), (g11), (g12), (g13), (g14), and (g15).

Other embodiments of this invention are directed to the compounds of this invention in the free base form. Thus, other embodiments are directed to any one of the embodiments above wherein the compound is in the free base form.

Other embodiments of this invention are directed to pharmaceutically acceptable salts of the compounds of this invention. Thus, other embodiments are directed to any one of the embodiments above wherein the compound is a pharmaceutically acceptable salt.

Representative compounds of the invention include, but are not limited to:

(18) 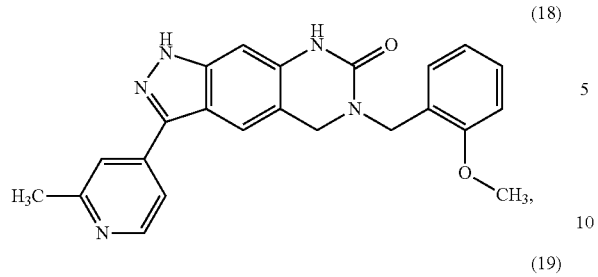
(19) 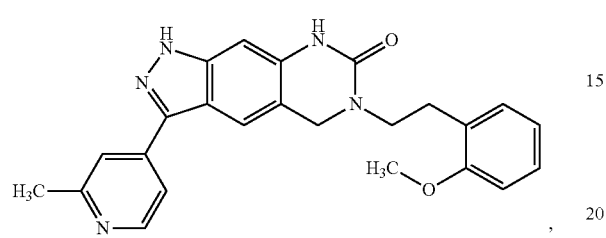
(20) 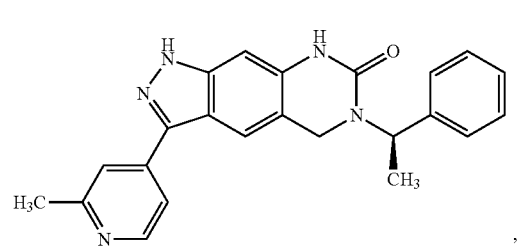
(21) 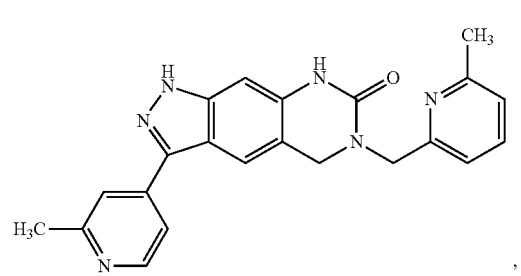
(22) 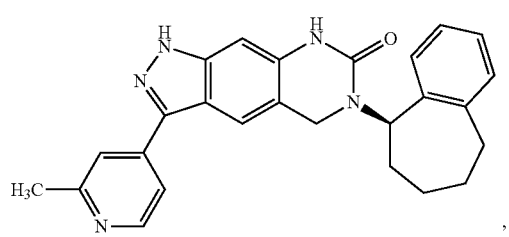
(23) 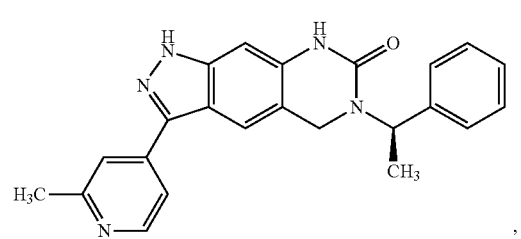
(24) 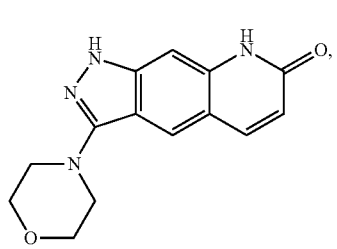
(25) 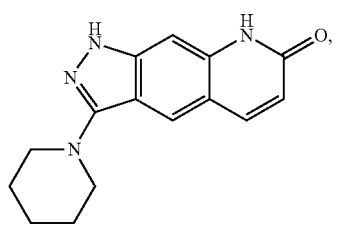
(26) 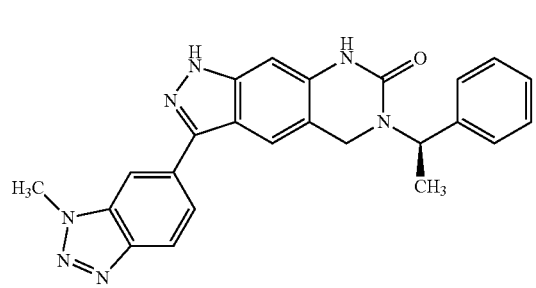
(27) 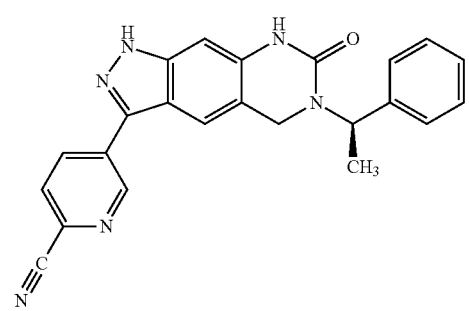
(28) 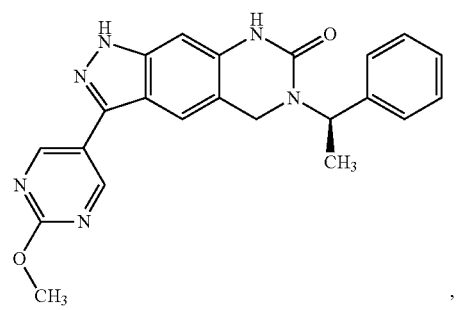
(29) 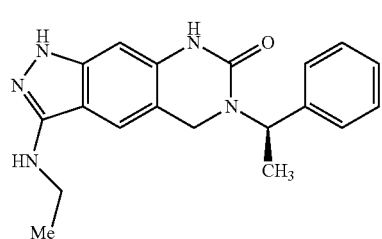

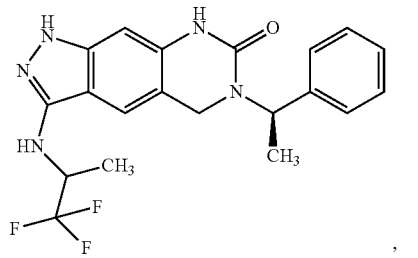
(30)
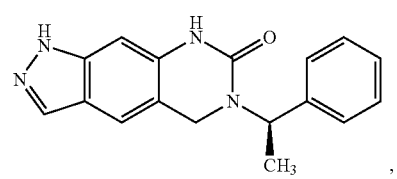
(31)
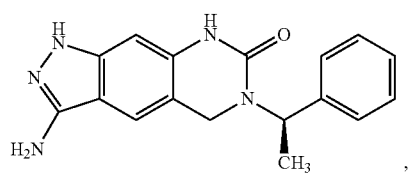
(32)
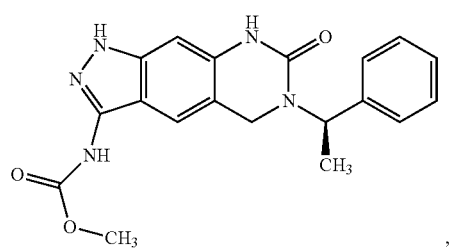
(33)
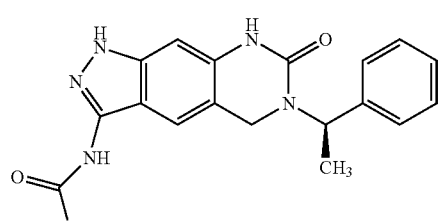
(34)
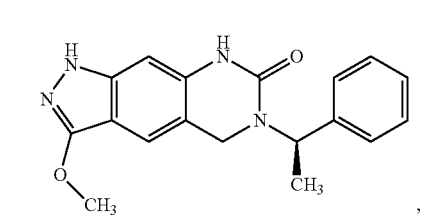
(35)
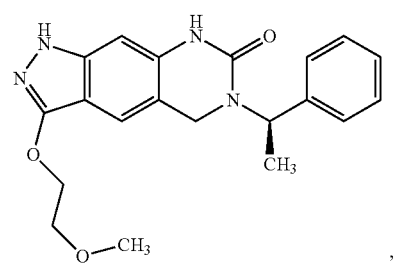
(36)
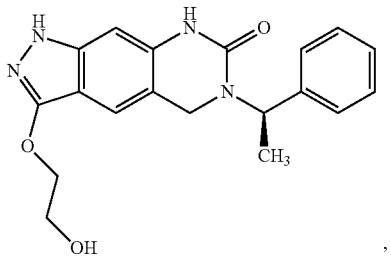
(37)
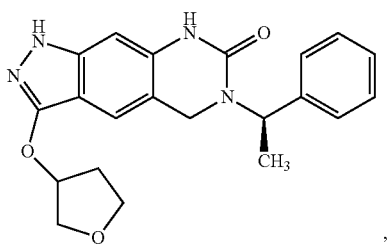
(38)
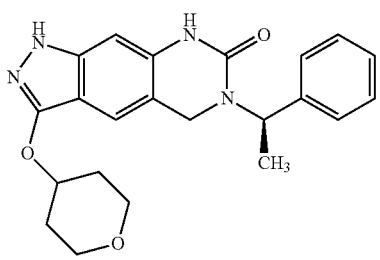
(39)
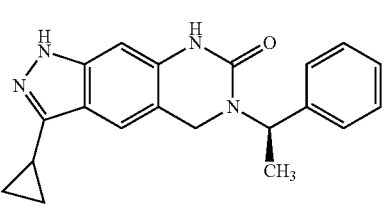
(40)
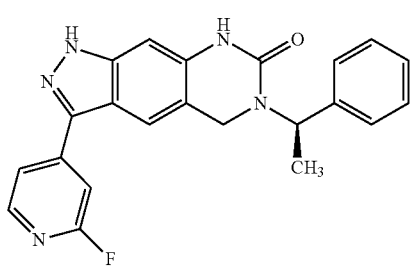
(41)
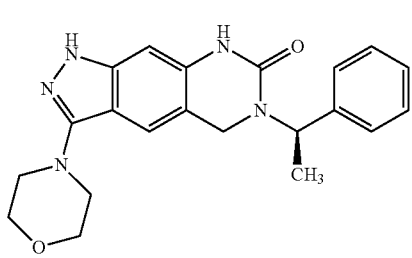
(42)

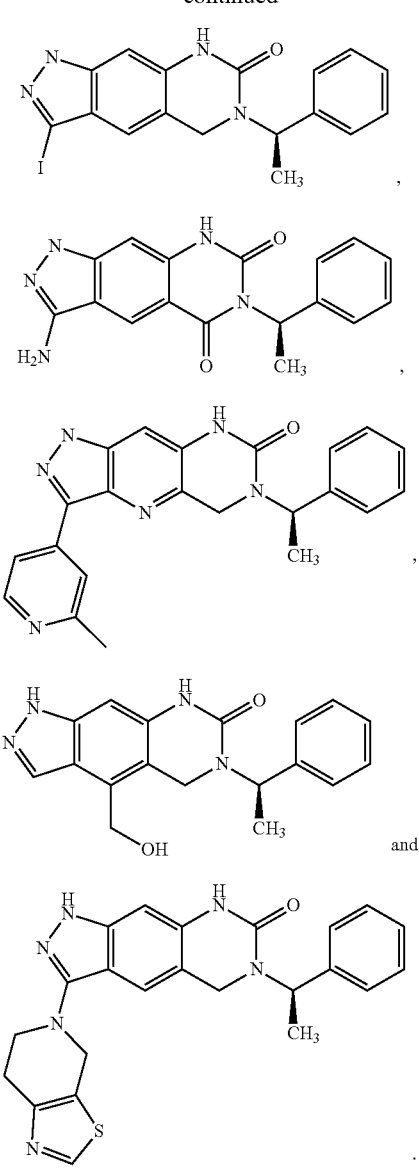

Representative compounds of the invention also include the pharmaceutically acceptable salts of compounds (1) to (47).

Compounds of the invention can have chiral centers, and compounds of the invention can be obtained as a salt (e.g., a formate or trifluoroacetate). Thus, compounds of the invention include, for example, the trifluoroacetate salt of compounds (4)-(9), (11)-(15), (17)-(26), (30)-(37), (39)-(41), (43), (44), and (47). The compounds of the invention also include, for example, the formate salt of compounds (27), (28) and (29).

In one embodiment the compound is compound (1). In another embodiment the compound is compound (2). In another embodiment the compound is compound (3). In another embodiment the compound is compound (4). In another embodiment the compound is compound (5). In another embodiment the compound is compound (6). In another embodiment the compound is compound (7). In another embodiment the compound is compound (8). In another embodiment the compound is compound (9). In another embodiment the compound is compound (10). In another embodiment the compound is compound (11). In another embodiment the compound is compound (12). In another embodiment the compound is compound (13). In another embodiment the compound is compound (14). In another embodiment the compound is compound (15). In another embodiment the compound is compound (16). In another embodiment the compound is compound (17). In another embodiment the compound is compound (18). In another embodiment the compound is compound (19). In another embodiment the compound is compound (20). In another embodiment the compound is compound (21). In another embodiment the compound is compound (22). In another embodiment the compound is compound (23). In another embodiment the compound is compound (24). In another embodiment the compound is compound (25). In another embodiment the compound is compound (26). In another embodiment the compound is compound (27). In another embodiment the compound is compound (28). In another embodiment the compound is compound (29). In another embodiment the compound is compound (30). In another embodiment the compound is compound (31). In another embodiment the compound is compound (32). In another embodiment the compound is compound (33). In another embodiment the compound is compound (34). In another embodiment the compound is compound (35). In another embodiment the compound is compound (36). In another embodiment the compound is compound (37). In another embodiment the compound is compound (38). In another embodiment the compound is compound (39). In another embodiment the compound is compound (40). In another embodiment the compound is compound (41). In another embodiment the compound is compound (42). In another embodiment the compound is compound (43). In another embodiment the compound is compound (44). In another embodiment the compound is compound (45). In another embodiment the compound is compound (46). In another embodiment the compound is compound (47).

Other embodiments are directed to a pharmaceutically acceptable salt of any one of compounds 1 to 47.

In one embodiment of this invention the compounds of formula (I) are selected from the group consisting of the compounds (4), (6), (7), (8), (10), (13)-(15), (17)-(21), (23), (26), (28), (33), (34), (41) and (45), or a pharmaceutically acceptable salt thereof. In one embodiment of this invention the compounds of formula (I) are selected from the group consisting of the compounds (4), (6), (7), (8), (10), (13)-(15), (17)-(21), (23), (26), (28), (33), (34), and (41), or a pharmaceutically acceptable salt thereof.

Another embodiment of this invention is directed to compounds of formula (I) selected from the group consisting of: (4), (6), (7), (10), and (41), or a pharmaceutically acceptable salt thereof.

Another embodiment of this invention is directed to the solvates of the compounds of formula (I).

Other embodiments of this invention are directed to any one of the embodiments of formula (I) wherein the compound is in pure and isolated form. Other embodiments of this invention are directed to any one of the embodiments of formula (I) wherein the compound is in pure form. Other embodiments of this invention are directed to any one of the embodiments of formula (I) wherein the compound is in isolated form.

Another embodiment of this invention is directed to a pharmaceutical composition comprising an effective amount of at least one compound (e.g., 1, 2 or 3, or 1 or 2, or 1, and usually 1) of formula (I), or a pharmaceutically acceptable salt thereof, and a pharmaceutically acceptable carrier. Another embodiment of this invention is directed to a pharmaceutical composition comprising an effective amount of a compound of formula (I), or a pharmaceutically acceptable salt thereof, and a pharmaceutically acceptable carrier.

Another embodiment of this invention is directed to a pharmaceutical composition comprising an effective amount of at least one compound selected from the group consisting of the compounds (1)-(47), or a pharmaceutically acceptable salt thereof, and a pharmaceutically acceptable carrier.

Another embodiment of this invention is directed to a pharmaceutical composition comprising an effective amount of at least one compound selected from the group consisting of the compounds (4), (6), (7), (8), (10), (13)-(15), (17)-(21), (23), (26), (28), (33), (34), (41), and (45) or a pharmaceutically acceptable salt thereof, and a pharmaceutically acceptable carrier.

Another embodiment of this invention is directed to a pharmaceutical composition comprising an effective amount of at least one compound selected from the group consisting of the compounds (4), (6), (7), (8), (10), (13)-(15), (17)-(21), (23), (26), (28), (33), (34) and (41), or a pharmaceutically acceptable salt thereof, and a pharmaceutically acceptable carrier.

Another embodiment of this invention is directed to a pharmaceutical composition comprising an effective amount of at least one compound selected from the group consisting of the compounds (4), (6), (7), (10), and (41), or a pharmaceutically acceptable salt thereof, a pharmaceutically acceptable carrier, and a pharmaceutically acceptable carrier.

Another embodiment of this invention is directed to a pharmaceutical composition comprising an effective amount of a compound of formula (I), a chemotherapeutic agent, and a pharmaceutically acceptable carrier.

The compounds of the invention are useful in preparing a medicament that is useful in treating cancer.

The compounds of this invention inhibit the activity of ERK2 Thus, this invention further provides a method of inhibiting ERK in mammals, especially humans, by the administration of an effective amount of one or more (e.g., one) compounds of this invention. The administration of the compounds of this invention to patients, to inhibit ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention. In the treatment of breast cancer, the compounds of formula (I) can be be administered in a treatment protocol which also includes the administration of an effective amount of at least one (e.g., 1-3, or 1-2, or 1) antihormonal agent (i.e., the methods of treating breast cancer can include hormonal therapies).

The methods of treating cancer described herein include methods wherein a combination of drugs (e.g., compounds, or pharmaceutically active ingredients, or pharmaceutical compositions) are used (e.g., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicyto-static agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another embodiment of this invention is directed to a method of treating cancer in a patient in need of such treatment, said method comprising administering an effective amount of a compound of formula (I). Another embodiment of this invention is directed to a method of treating cancer in a patient in need of such treatment, said method comprising administering to said patient an effective amount of a compound of formula (I), and an effective amount of at least one (e.g., 1-3, 1-2, or 1) chemotherapeutic agent.

The compounds, compositions and methods provided herein are useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (I) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one embodiment of this invention the cancer treated is colorectal cancer (such as, for example, colon adenocarcinoma and colon adenoma). Thus, another embodiment of this invention is directed to a method of treating colorectal cancer in a patient in need of such treatment, said method comprising administering an effective of a compound of formula (I) (in one example, a compound selected from the group consisting of compounds (1)-(47), or a pharmaceutically acceptable salt thereof, and in another example a compound selected from the group consisting of: compounds (4), (6), (7), (8), (10), (13)-(15), (17)-(21), (23), (26), (28), (33), (34), (41) and (45), or a pharmaceutically acceptable salt thereof, and in another example compounds (4), (6), (7), (8), (10), (13)-(15), (17)-(21), (23), (26), (28), (33), (34) and (41), or a pharmaceutically acceptable salt thereof, and in another example a compound selected from the group consisting of compounds (4), (6), (7), (10), and (41), or a pharmaceutically acceptable salt thereof), to said patient. Another embodiment of this invention is directed to a method of treating colorectal cancer in a patient in need of such treatment, said method comprising administering to said patient an effective amount of a compound of formula (I) (in one example, a compound selected from the group consisting of compounds (1)-(47), or a pharmaceutically acceptable salt thereof, and in another example a compound selected from the group consisting of: compounds (4), (6), (7), (8), (10), (13)-(15), (17)-(21), (23), (26), (28), (33), (34), (41) and (45), or a pharmaceutically acceptable salt thereof, and in another example compounds (4), (6), (7), (8), (10), (13)-(15), (17)-(21), (23), (26), (28), (33), (34) and (41), or a pharmaceutically acceptable salt thereof, and in another example a compound selected from the group consisting of compounds (4), (6), (7), (10), and (41), or a pharmaceutically acceptable salt thereof), and an effective amount of at least one (e.g., 1-3, or 1-2, or 1) chemotherapeutic agent.

In one embodiment of this invention the cancer treated is melanoma. Thus, another embodiment of this invention is directed to a method of treating melanoma in a patient in need of such treatment, said method comprising administering an effective amount of a compound of formula (I) (in one example, a compound selected from the group consisting of compounds (1)-(47), or a pharmaceutically acceptable salt thereof, and in another example a compound selected from the group consisting of: compounds (4), (6), (7), (8), (10), (13)-(15), (17)-(21), (23), (26), (28), (33), (34), (41) and (45), or a pharmaceutically acceptable salt thereof, and in another example compounds (4), (6), (7), (8), (10), (13)-(15), (17)-(21), (23), (26), (28), (33), (34) and (41), or a pharmaceutically acceptable salt thereof, and in another example a compound selected from the group consisting of compounds (4), (6), (7), (10), and (41), or a pharmaceutically acceptable salt thereof), to said patient. Another embodiment of this invention is directed to a method of treating melanoma in a patient in need of such treatment, said method comprising administering to said patient an effective amount of a compound of formula (I) (in one example, a compound selected from the group consisting of compounds (1)-(47), or a pharmaceutically acceptable salt thereof, and in another example a compound selected from the group consisting of: compounds (4), (6), (7), (8), (10), (13)-(15), (17)-(21), (23), (26), (28), (33), (34), (41) and (45), or a pharmaceutically acceptable salt thereof, and in another example compounds (4), (6), (7), (8), (10), (13)-(15), (17)-(21), (23), (26), (28), (33), (34) and (41), or a pharmaceutically acceptable salt thereof, and in another example a compound selected from the group consisting of compounds (4), (6), (7), (10), and (41), or a pharmaceutically acceptable salt thereof), or a pharmaceutically acceptable salt thereof, and an effective amount of at least one (e.g., 1-3, or 1-2, or 1) chemotherapeutic agent.

The compounds of the invention are also useful in preparing a medicament that is useful in treating cancer.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium croscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. Compounds of this invention can be administered in a total daily dose of 10 mg to 3000 mg. For example, compounds of the instant invention can be administered in a total daily dose of up to 3000 mg. Compounds of the instant invention can be administered once daily (QD), or divided into multiple daily doses such as twice daily (BID), and three times daily (TID). Compounds of the instant invention can be administered at a total daily dosage of up to 3000 mg, e.g., 200 mg, 300 mg, 400 mg, 600 mg, 800 mg, 1000 mg, 2000 mg or 3000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days. The compounds of this invention may be administered discontinuously rather than continuously during the treatment cycle. Thus, the compounds of this invention may be administered daily for one or more weeks during the cycle and discontinued for one or more weeks during the cycle, with this pattern of administration repeating during the treatment cycle (e.g., administration for a week and then discontinued for a week). This discontinuous treatment may also be based upon numbers of days rather than a full week. The number of days (or weeks) that the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal to or greater than the number of days or weeks that the compounds of this invention are not dosed.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/

019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. No. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al (Am. J. Hum. Genet. 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (J. Immunol. 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another embodiment of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCHinhibitors, agents that interfere with receptor tyrosine kinases (RTKs), an agent that interferes with a cell cycle checkpoint, and any of the therapeutic agents listed above.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians'Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), the Physicians' Desk Reference, 60$^{th}$ Edition, 2006 (published by Thompson PDR, Montvale, N.J. 07645-1742), and the Physicians' Desk Reference, 64$^{th}$ Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula (I) hereinabove.

SCHEMES

In Scheme 1 5-bromo-6-nitro-1H-indazole (S1) is subjected to a metal catalyzed or metal-facilitated process (such as Stille or Suzuki coupling) to provide olefin S2, which is then converted to S3 ($X^1$=Cl, Br, or I) by techniques well known in the art (such as treatment with NaOCl, N-chlorosuccinimide, N-bromosuccinimide, $Br_2$, N-iodosuccinimide or $I_2$, with or without a base such as KOH, NaOH, $K_2CO_3$, $Cs_2CO_3$, or LiHMDS; or $I_2/Ag_2SO_4$). Compound S3 can then be protected with a protecting group (PG) such as trityl, BOC, or SEM. The resulting compound S4 is converted to the aldehyde S5 by ozonolysis, treatment with $OsO_4/NaIO_4$, or another technique well known in the art and is then subjected to a reductive amination with an appropriate primary amine. The nitro group in S6 is then reduced (e.g. using Zn, Fe, $Pd(OH)_2$—$H_2$, Pt/V—$H_2$, $SnCl_2$ or other reagent well known in the art) and the resulting amine is cyclized with triphosgene, CDI, 4-nitrophenyl chloroformate, or other appropriate reagent to provide S7. Compound S8 is then obtained using a metal catalyzed or metal-facilitated C—C, C—N, or C—O process (such as Stille, Suzuki, Negishi, Buchwald or other coupling) or other appropriate chemical transformation. Compound S9 is obtained through a protecting group (PG) deprotection step (e.g. TFA for PG=Boc, trityl or SEM).

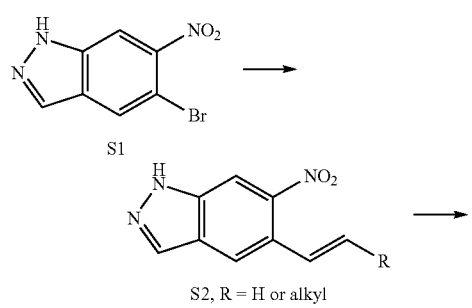

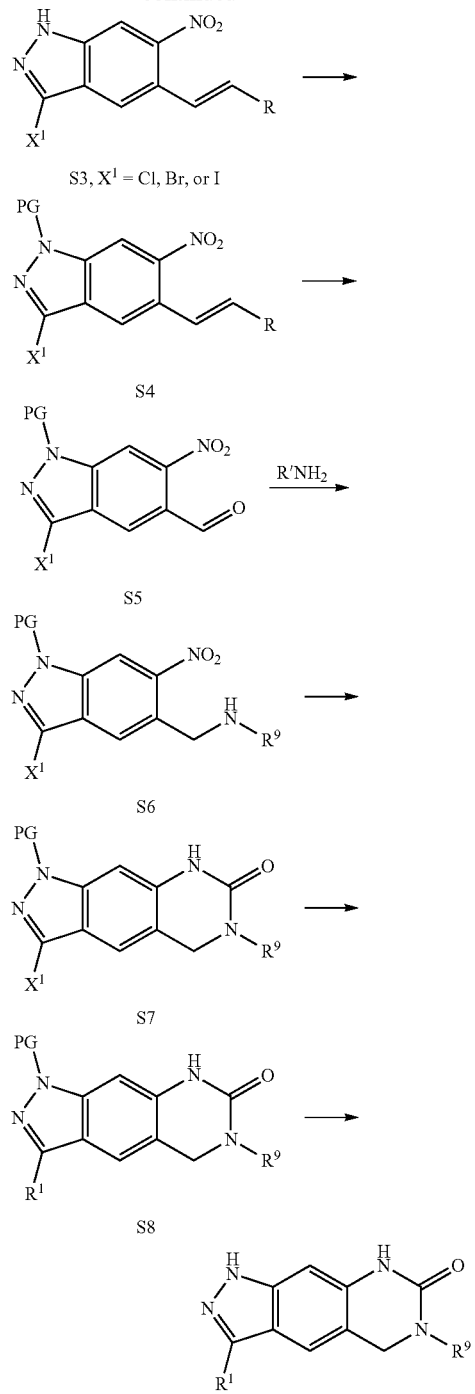

In Scheme 2 compound S1 is first halogenated (as described in Scheme 1), protected, and then is subjected to further derivatization at the C3-position (via a metal catalyzed or metal-facilitated process, such as Stille, Suzuki, Negishi, or Buchwald coupling. The resulting compound S11 is then converted to the aldehyde S12 (as described in Scheme 1 or by another method such as lithium halogen exchange followed electrophile quench, e.g. nBuLi/DMF) and is subjected to the reductive amination-nitro reduction-ring closure sequence described in Scheme 1.

Scheme 2

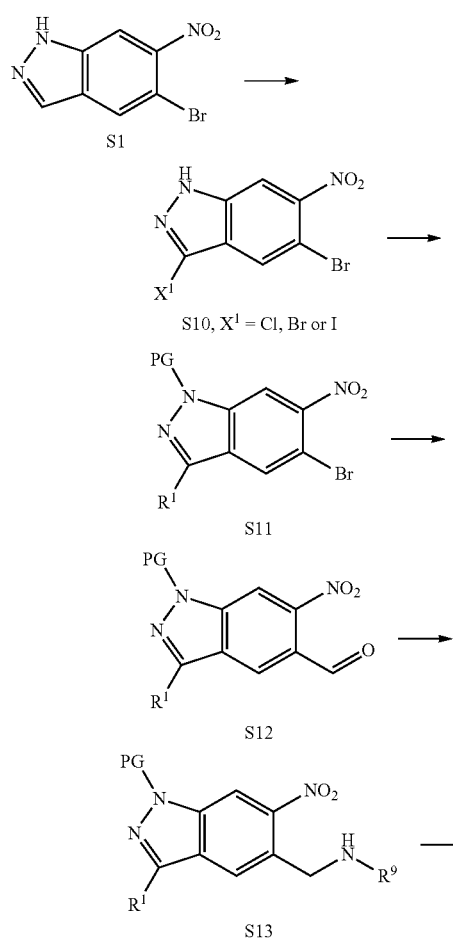

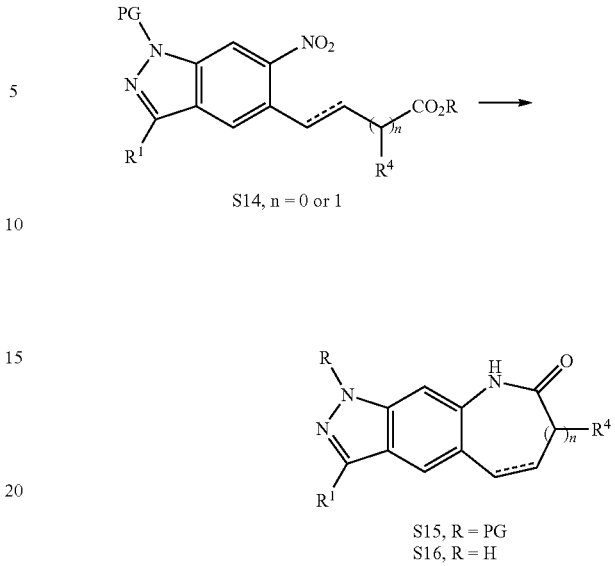

S14, n = 0 or 1

In Scheme 3 compound S11 is converted to S14 (via a metal catalyzed or metal-facilitated process, such as Stille coupling, Suzuki coupling, or Negishi coupling. The nitro group in S14 is then reduced and cyclized to provide S15, which is deprotected to provide S16.

In Scheme 4 compound S15a is optionally protected with an additional protecting group (such as BOC) and then is further substituted once or twice by treatment with an appropriate base and electrophile. The resulting compound S16a is then deprotected.

Scheme 4

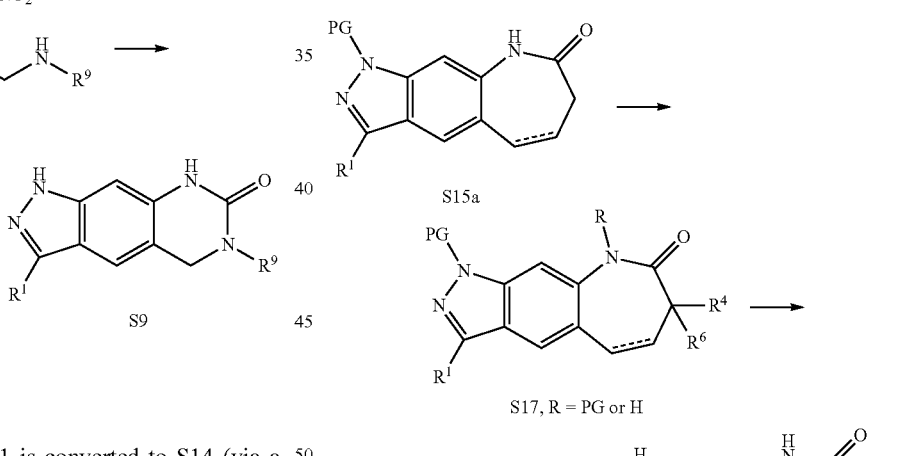

In Scheme 5 the methyl ester S18a or S18b is subjected to a sequence similar to that described in Scheme 2 (sequential C3-halogenation, C3-coupling and N1-protection) to provide S21a or S21b. Subsequent coupling of S21b ($Y^1$=Cl) with an appropriate urea (such as benzyl urea) and concomitant ring closing provides S22. Alternatively, S22 is accessed from S21a ($Y^1$=NO$_2$) via sequential nitro reduction, reaction with an appropriate isocyanate (such as benzyl isocyanate) and ring closure.

Scheme 3

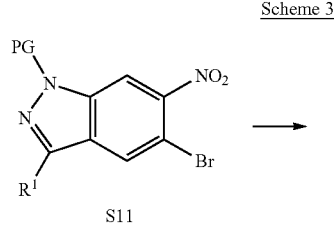

Scheme 5

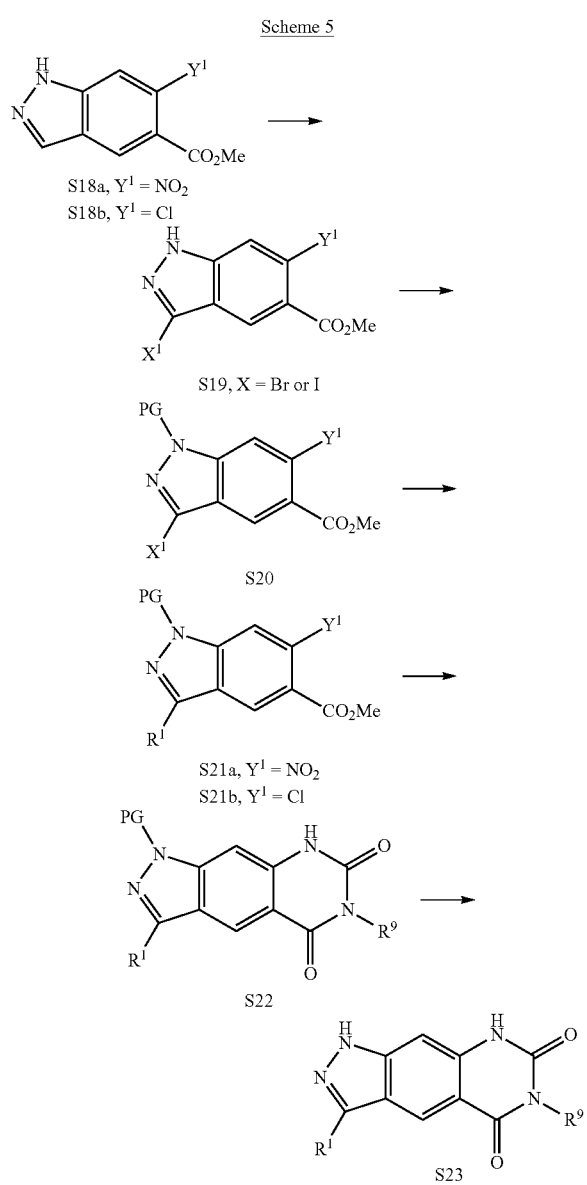

with an appropriate base (such as $Cs_2CO_3$ or $K_3PO_4$) and appropriate ligand such as tetramethylphenanthroline, 2-isobutyrylcyclohexanone, or trans-N,N'-dimethylcyclohexane-1,2-diamine. Compound 24a or 24b is then deprotected.

Scheme 6

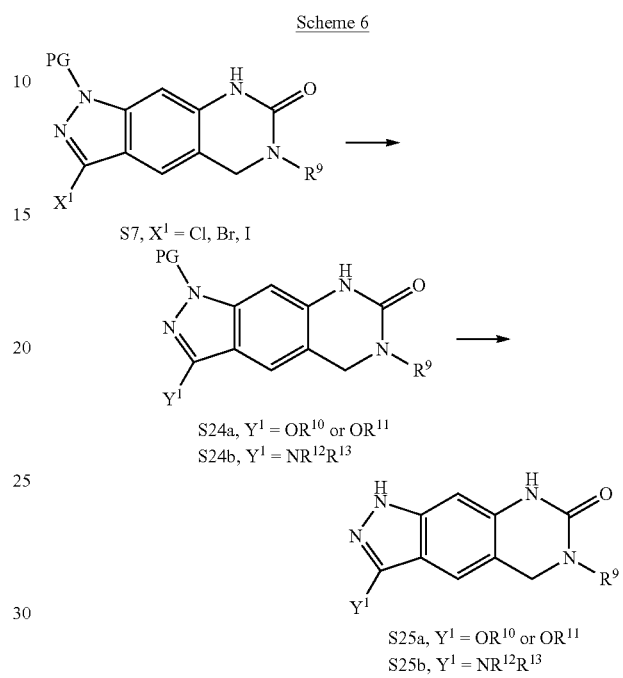

In Scheme 7 compound S7 is coupled with 2,4-dimethoxybenzylamine (DMB, using BrettPhos Pd-precatalyst or the like) to provide S26 which is further acylated to provide S27 (e.g. in which $R^{12}$ can be Ac using AcCl; $R^{12}$ may be $CO_2Me$ using $ClCO_2Me$; or a similar acylation). Alternatively, S26 can undergo a reductive amination with an appropriately substituted aldehyde or a $S_N2$ or $S_NAr$-type reaction with an appropriate electrophile. Final global deprotection with a reagent such as TFA can be used to remove the DMB and N1-protecting group (e.g. when it is Boc, Tr, or SEM). In another embodiment, S26 can be converted directly to S28 by global deprotection ($R^{12}$=H).

In Scheme 6 S7 ($X^1$=Cl, Br, or I) undergoes a C—O or C—N coupling at the C3 position. The C—O coupling of S7 ($X^1$=Br or I) with an appropriate alcohol to provide S24a can be achieved using CuI (with an appropriate base such as $Cs_2CO_3$ and an appropriate ligand such as tetramethylphenanthroline, e.g. see Buchwald et. al. J. Org. Chem., 2008, 73, 284) or via a palladium-catalyzed process (with an appropriate phosphine ligand such as RockPhos; e.g. see Buchwald et. al. Angew. Chem. Int. Ed. 2011, 50, 9943 or JosiPhos, e.g. see Maligres et. al. Angew. Chem. Int. Ed. 2012, 51, 9071 or tBuXPhos, see Buchwald et. al. Angew. Chem. Int. Ed., 2006, 45, 4321). The C—N coupling of S7 ($X^1$=Cl, Br, or I) with an appropriate amine to provide S24b may be achieved using a palladium precatalyst such as BrettPhos precatalyst, tBuXPhos precatalyst, Xphos precatalyst, RuPhos precatalyst or Sphos precatalyst and an appropriate base such as NaOtBu, $Cs_2CO_3$ or $K_3PO_4$ (see e.g. Buchwald et. al., Chem. Sci., 2011, 2, 27). Alternatively, the C—N coupling of S7 ($X^1$=I) with an appropriate amine to provide S24b may be achieved using CuI or $Bu_4NCuI_2$

Scheme 7

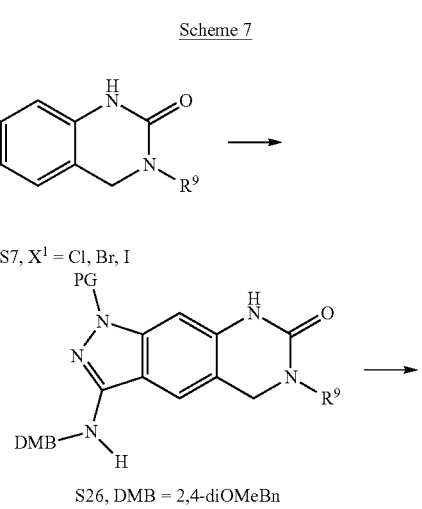

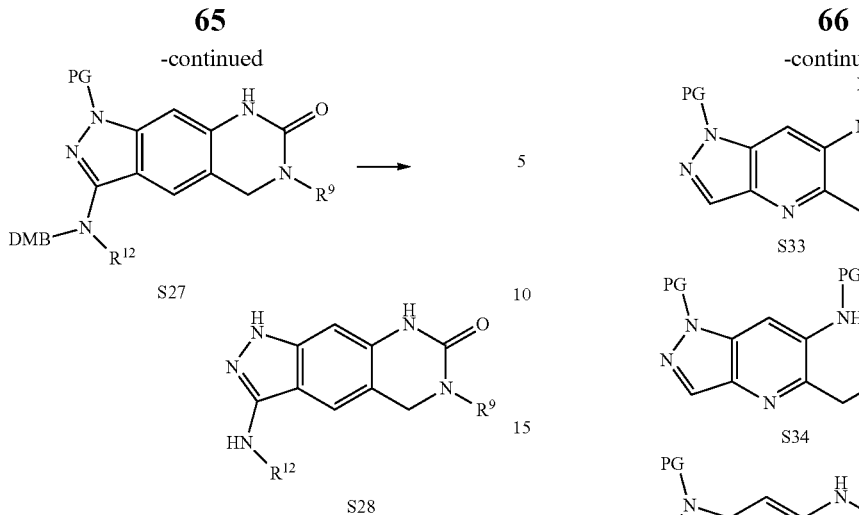

In Scheme 8 5,6-dibromo-1H-pyrazolo[4,3-b]pyridine (S29) (which is commerically available or alternatively may be synthesized from 5-bromo-2-methyl-3-nitropyridine (see PCT Int. Appl., 2010056999, 20 May 2010)) is subjected to a metal catalyzed or metal-facilitated process (such as Stille or Suzuki coupling) to provide olefin S30, which is then protected with an appropriate protecting group (e.g. SEM). The resulting compound S31 (Y=Br) is subjected to an amination with an appropriately protected amine (e.g. BOC—NH$_2$, CBz-NH$_2$, BnNH$_2$ etc) to provide S32 (Y$^1$=NH—PG). In a manner similar to that described in Scheme 1, S32 is converted to the aldehyde S33 (e.g. by ozonolysis or treatment with OsO$_4$/NaIO$_4$) and then to S34 by reductive amination with an appropriate primary amine. Selective deprotection of S34 is followed by cyclization with triphosgene, CDI, 4-nitrophenyl chloroformate, or other appropriate reagent. The resulting compound S35 is iodinated (e.g. with AgSO$_4$/I$_2$), coupled with an appropriate R$^1$ group and deprotected to provide S37. Alternatively, the deprotection step is performed first, followed by halogenation (e.g. X$^1$=Cl, Br, or I by a method such as treatment with NaOCl, N-chlorosuccinimide, N-bromosuccinimide, Br$_2$, N-iodosuccinimide or I$_2$, with or without a base such as KOH, NaOH, K$_2$CO$_3$, Cs$_2$CO$_3$, or LiHMDS) and final coupling.

Scheme 8

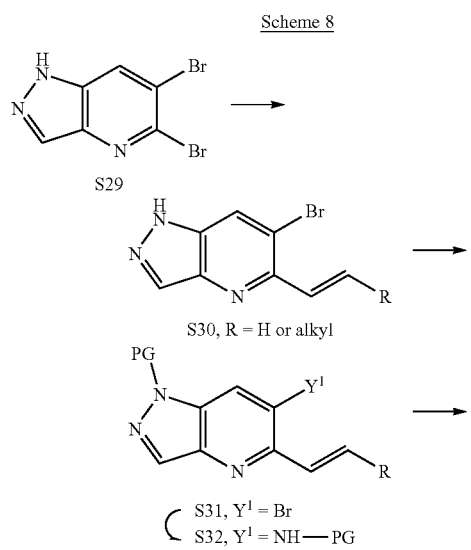

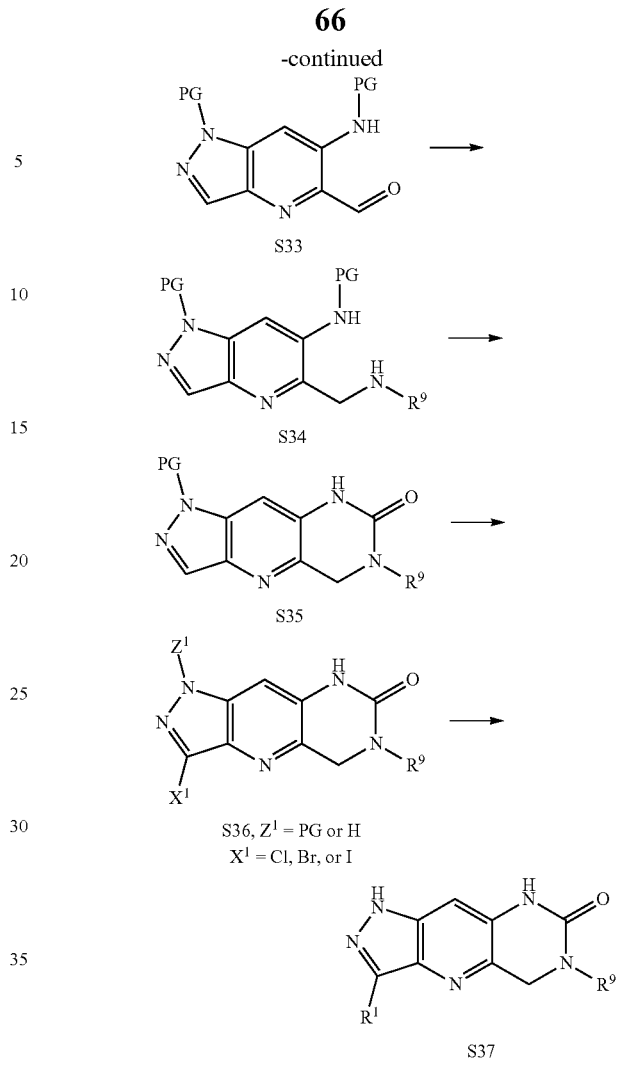

In Scheme 9 S1 is iodinated and protected in a manner similar to that previously described in Scheme 1 (PG=SEM, Boc, Tr or other appropriate group). The resulting compound S38 is subjected to a metal catalyzed or metal-facilitated C—C, C—N, or C—O process (such as Stille, Suzuki, Negishi, or Buchwald coupling) to provide S39. Compound S39 is then converted to S40 by one of a number of techniques known in the art (such as a metal catalyzed carbonylation reaction, lithium-halogen exchange or Grignard formation followed by quench with an appropriate electrophile, or metal catalyzed C—C coupling with an appropriate partner such as n-butyl vinyl ether or (1-ethoxyethenyl)tributyltin, followed by acid treatment). Compound S40 is then converted sequentially to S41 and then S42 in a manner similar to that previously described in Scheme 1.

Alternatively, in Scheme 10 compound S5 (X$^1$=Cl, Br, or I) is treated with an appropriate nucleophile (such as a Grignard or lithiated species) and the resulting alcohol is then oxidized to provide the ketone S43, which is further elaborated as previously described (i.e. Schemes 1 and 9).

Scheme 9

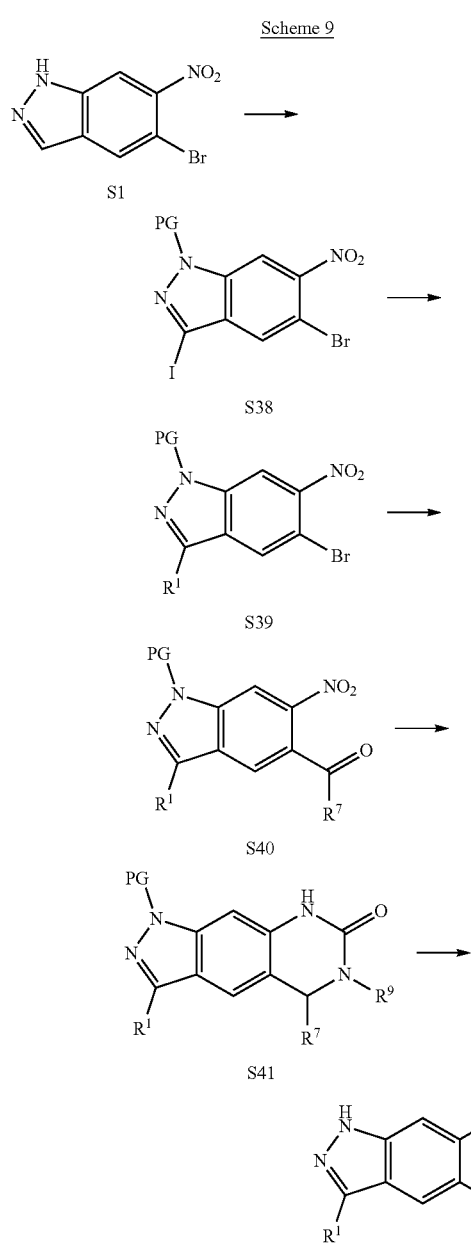

Scheme 10

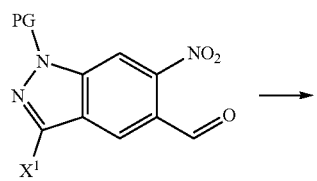

-continued

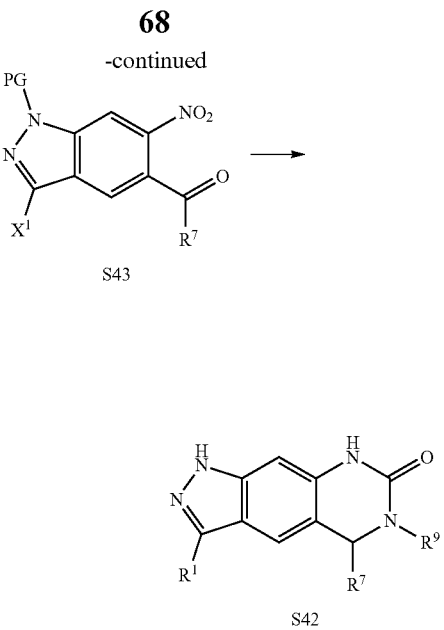

EXAMPLES

Example 1

3-(2-methylpyridin-4-yl)-1,8-dihydro-7H-pyrazolo[4,3-g]quinolin-7-one

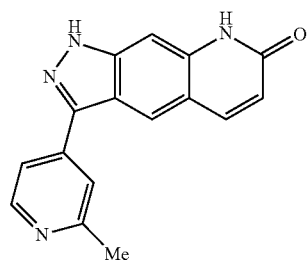 [SMILES: Cc1cc(-c2n[nH]c3cc4[nH]c(=O)ccc4cc23)ccn1]

Step 1

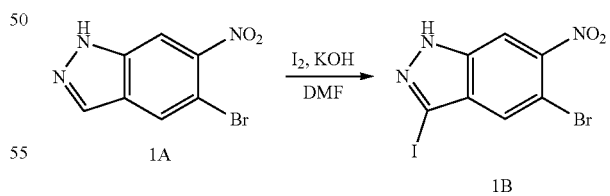

To a stirred solution of 5-bromo-6-nitro-1H-indazole (10.0 g, 41.3 mmol) in DMF (41 mL) were added iodine (21.0 g, 83 mmol) and potassium hydroxide (8.69 g, 155 mmol). The mixture was left to stir overnight, treated with aqueous sodium thiosulfate solution, and filtered through a fritted glass. The solid was washed with water and dried under vacuum to afford 5-bromo-3-iodo-6-nitro-1H-indazole as an orange solid. $^1$H NMR (600 MHz, DMSO-d6) δ 8.38 (s, 1H), 7.92 (s, 1H).

Step 2

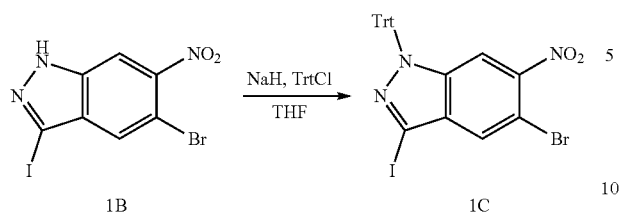

To a stirred solution of 5-bromo-3-iodo-6-nitro-1H-indazole (9.21 g, 25.0 mmol) in THF (78 mL) was added NaH (60%, 1.3 g, 32.5 mmol) at 0° C. The mixture was left to stir at 0° C. for 30 min and treated with trityl-Cl (7.68 g, 27.5 mmol). The bath was removed and the mixture was left to stir overnight. The mixture was cooled to 0° C. and treated with aqueous ammonium chloride solution. The mixture was concentrated to half a volume, and filtered through a fritted glass. The brown solid was washed with hexanes, and dried under high vacuum to afford 5-bromo-3-iodo-6-nitro-1-trityl-1H-indazole. $^1$H NMR (600 MHz, DMSO-d6) δ 7.98 (s, 1H), 7.16-7.38 (m, 15H), 6.74 (s, 1H).

Step 3

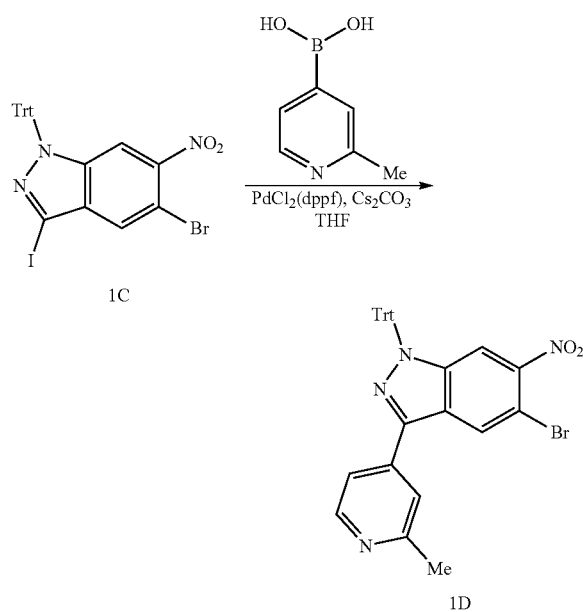

A mixture of 5-bromo-3-iodo-6-nitro-1-trityl-1H-indazole (13.0 g, 21.3 mmol), 2-methylpyridine-4-boronic acid (3.79 g, 27.7 mmol), PdCl$_2$(dppf)-CH$_2$Cl$_2$ (1.74 g, 2.13 mmol), and cesium carbonate (20.8 g, 63.9 mmol) in THF (107 mL) was purged with nitrogen for 10 min, and heated to 80° C. overnight. The mixture was cooled to room temperature, and treated with water. THF was evaporated, and the residue was extracted with EtOAc (×3). The combined organics were washed with brine, dried (sodium sulfate), concentrated, and purified by flash chromatography to afford 5-bromo-3-(2-methylpyridin-4-yl)-6-nitro-1-trityl-1H-indazole. MS: [M+H]$^+$ m/z 575. $^1$H NMR (600 MHz, DMSO-d6) δ 8.74 (s, 1H), 8.55 (d, J=5.3 Hz, 1H), 7.78 (s, 1H), 7.67 (d, J=5.0 Hz, 1H), 7.22-7.41 (m, 15H), 6.82 (s, 1H), 2.57 (s, 3H).

Step 4

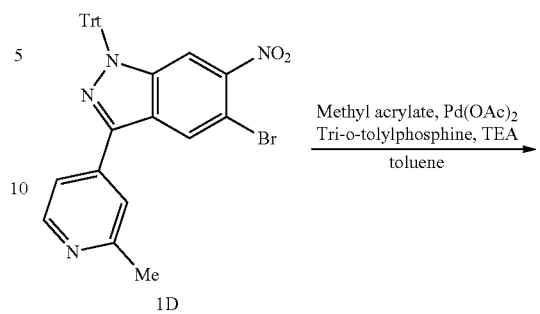

A mixture of 5-bromo-3-(2-methylpyridin-4-yl)-6-nitro-1-trityl-1H-indazole (3.5 g, 6.1 mmol), methyl acrylate (5.24 g, 60.8 mmol), Pd(OAc)$_2$ (0.14 g, 0.61 mmol), tri-o-tolylphosphine (0.37 g, 1.22 mmol), and triethylamine (1.85 g, 18.3 mmol) in toluene (30 mL) was purged with nitrogen for 5 min, and heated to 70° C. overnight. Additional methyl acrylate (4.8 g, 56 mmol) was added to the mixture and the resultant solution was heated to 70° C. overnight. The mixture was treated with water, and extracted with EtOAc (×3). The combined organics were washed with brine, dried (sodium sulfate), and concentrated. The residue was triturated with ether and hexanes to afford methyl (2E)-3-[3-(2-methylpyridin-4-yl)-6-nitro-1-trityl-1H-indazol-5-yl]prop-2-enoate. MS: [M+H]$^+$ m/z 581. $^1$H NMR (600 MHz, DMSO-d6) δ 8.58 (d, J=5.0 Hz, 1H), 8.56 (s, 1H), 7.89 (d, J=15.8 Hz, 1H), 7.80 (s, 1H), 7.77 (d, J=5.0 Hz, 1H), 7.22-7.42 (m, 15H), 6.97 (s, 1H), 6.81 (d, J=15.9 Hz, 1H), 3.75 (s, 3H), 2.57 (s, 3H).

Steps 5-6

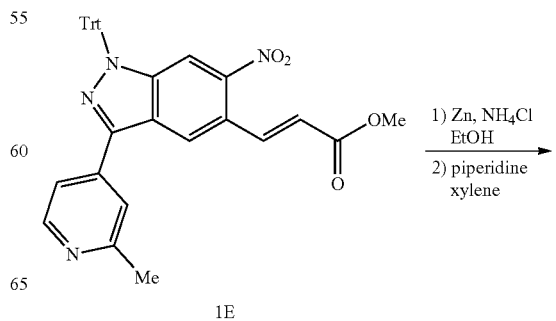

Example 2

6-bromo-3-(2-methylpyridin-4-yl)-1,8-dihydro-7H-pyrazolo[4,3-g]quinolin-7-one

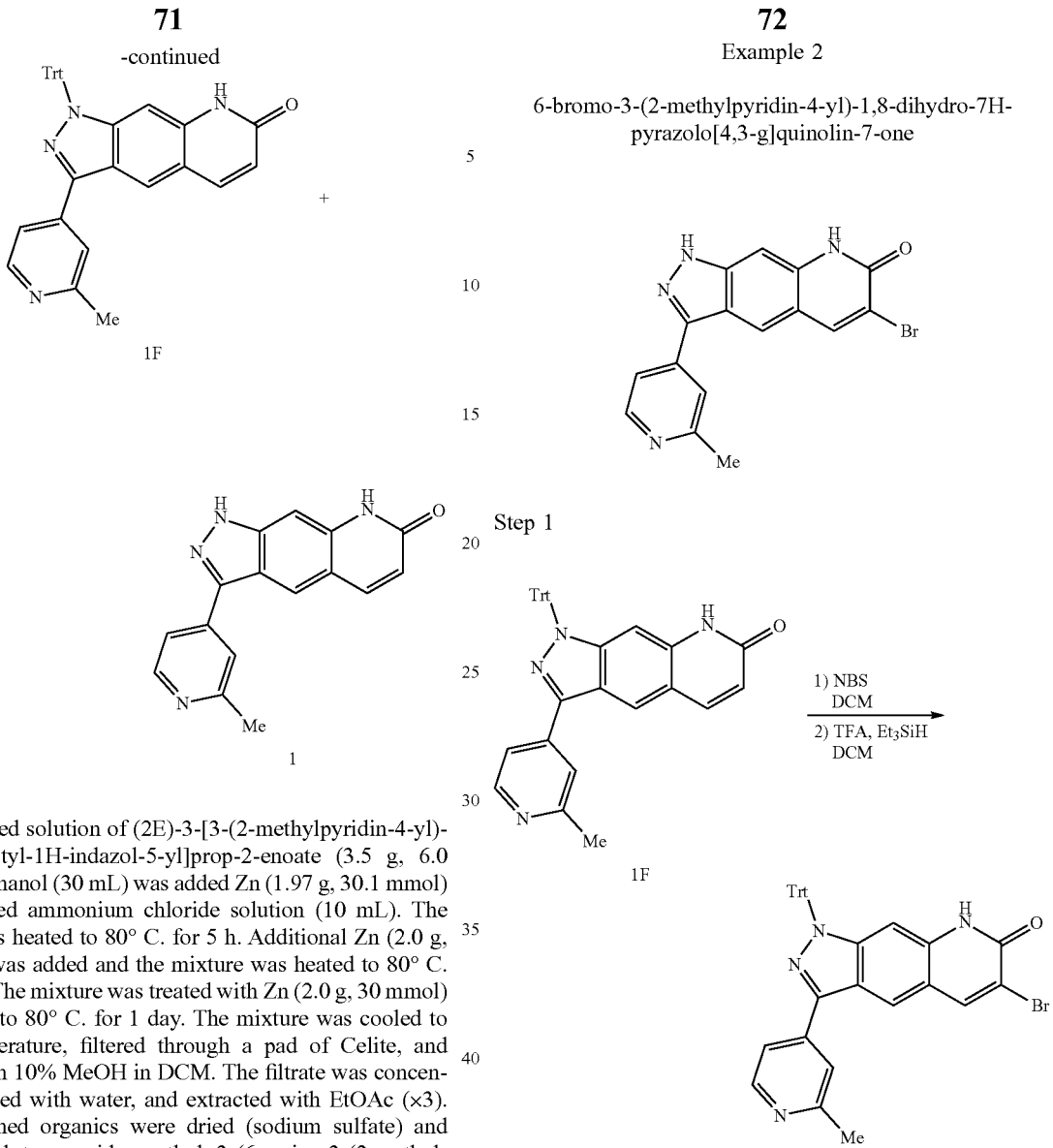

Step 1

To a stirred solution of (2E)-3-[3-(2-methylpyridin-4-yl)-6-nitro-1-trityl-1H-indazol-5-yl]prop-2-enoate (3.5 g, 6.0 mmol) in ethanol (30 mL) was added Zn (1.97 g, 30.1 mmol) and saturated ammonium chloride solution (10 mL). The mixture was heated to 80° C. for 5 h. Additional Zn (2.0 g, 30 mmol) was added and the mixture was heated to 80° C. overnight. The mixture was treated with Zn (2.0 g, 30 mmol) and heated to 80° C. for 1 day. The mixture was cooled to room temperature, filtered through a pad of Celite, and washed with 10% MeOH in DCM. The filtrate was concentrated, diluted with water, and extracted with EtOAc (×3). The combined organics were dried (sodium sulfate) and concentrated to provide methyl 3-(6-amino-3-(2-methylpyridin-4-yl)-1-trityl-1H-indazol-5-yl)acrylate, which was used in the next step without further purification. MS: [M+H]+ m/z 551.

To a stirred solution of the crude product in xylene (126 mL) was added piperidine (3.22 g, 37.8 mmol). The reaction mixture was heated to 130° C. for 3 days, cooled to room temperature, and concentrated. The residue was purified by flash chromatography to afford 3-(2-methylpyridin-4-yl)-1,8-dihydro-7H-pyrazolo[4,3-g]quinolin-7-one and 3-(2-methylpyridin-4-yl)-1-trityl-1,8-dihydro-7H-pyrazolo[4,3-g]quinolin-7-one. For 3-(2-methylpyridin-4-yl)-1,8-dihydro-7H-pyrazolo[4,3-g]quinolin-7-one; MS: [M+H]+ m/z 277. $^1$H NMR (600 MHz, DMSO-d6) δ 13.54 (s, 1H), 11.67 (s, 1H), 8.62 (s, 1H), 8.60 (d, J=4.7 Hz, 1H), 8.07 (d, J=9.7 Hz, 1H), 7.96 (s, 1H), 7.89 (d, J=4.4 Hz, 1H), 7.41 (s, 1H), 6.44 (d, J=9.4 Hz, 1H), 2.60 (s, 3H). For 3-(2-methylpyridin-4-yl)-1-trityl-1,8-dihydro-7H-pyrazolo[4,3-g]quinolin-7-one; MS: [M+H]+ m/z 519. $^1$H NMR (600 MHz, DMSO-d6) δ 11.36 (s, 1H), 8.57 (s, 1H), 8.55 (d, J=5.3 Hz, 1H), 8.00 (d, J=9.7 Hz, 1H), 7.77 (s, 1H), 7.67 (d, J=4.1 Hz, 1H), 7.24-7.36 (m, 15H), 6.62 (s, 1H), 6.39 (d, J=9.7 Hz, 1H), 2.56 (s, 3H).

To a stirred solution of 3-(2-methylpyridin-4-yl)-1-trityl-1,8-dihydro-7H-pyrazolo[4,3-g]quinolin-7-one (1.8 g, 3.5 mmol) in DCM (69 mL) was added NBS (0.62 g, 3.5 mmol). The mixture was left to stir for 4 h, treated with additional NBS (0.62 g, 3.5 mmol), and left to stir overnight. The mixture was treated with additional NBS (0.5 g, 2.8 mmol) and left to stir for 5 h. The mixture was treated with aqueous Na$_2$S$_2$O$_3$ solution, and extracted with EtOAc (×3). The combined organics were dried (sodium sulfate), concentrated, and purified by flash chromatography. The fractions were combined, concentrated, washed with water, and dried under high vacuum to afford 6-bromo-3-(2-methylpyridin-4-yl)-1-trityl-1,8-dihydro-7H-pyrazolo[4,3-g]quinolin-7-one. MS: [M+H]+ m/z 597.

To a stirred solution of 6-bromo-3-(2-methylpyridin-4-yl)-1-trityl-1,8-dihydro-7H-pyrazolo[4,3-g]quinolin-7-one (40 mg, 0.067 mmol) in DCM (2 mL) were added TFA (0.4 mL) and triethylsilane (30 μL, 0.19 mmol). The reaction mixture was left to stir for 3 h, concentrated, and purified by prep-HPLC. The desired fractions were treated with saturated NaHCO$_3$ solution, and extracted with DCM (×3). The combined organics were dried (sodium sulfate), concentrated, and dried under high vacuum to afford 6-bromo-3-(2-methylpyridin-4-yl)-1,8-dihydro-7H-pyrazolo[4,3-g]quinolin-7-one. MS: [M+H]+ m/z 355. ¹H NMR (600 MHz, DMSO-d6) δ 13.55 (s, 1H), 12.15 (s, 1H), 8.65 (s, 1H), 8.64 (s, 1H), 8.58 (d, J=5.0 Hz, 1H), 7.89 (s, 1H), 7.82 (d, J=5.0 Hz, 1H), 7.43 (s, 1H), 2.60 (s, 3H).

Example 3

6-benzyl-3-(2-methylpyridin-4-yl)-1,8-dihydro-7H-pyrazolo[4,3-g]quinolin-7-one

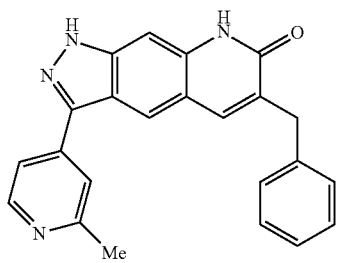 [SMILES: Cc1cc(-c2n[nH]c3cc4[nH]c(=O)c(Cc5ccccc5)cc4cc23)ccn1]

Steps 1-2

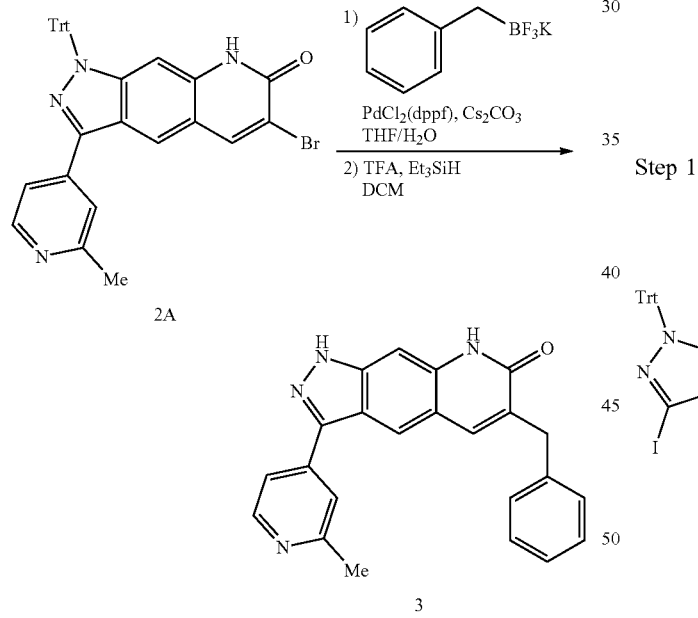

A mixture of 6-bromo-3-(2-methylpyridin-4-yl)-1-trityl-1,8-dihydro-7H-pyrazolo[4,3-g]quinolin-7-one (52 mg, 0.087 mmol), potassium benzyltrifluoroborate (43 mg, 0.22 mmol), PdCl₂(dppf)-CH₂Cl₂ (7.1 mg, 0.0087 mmol), and cesium carbonate (85 mg, 0.26 mmol) in THF (1.6 mL)/water (0.16 mL) was purged with nitrogen for 5 min, heated to 70° C. overnight, and cooled to room temperature. The mixture was treated with water, and extracted with EtOAc (×3). The combined organics were washed with brine, dried (sodium sulfate), concentrated, and purified by flash chromatography to afford 6-benzyl-3-(2-methylpyridin-4-yl)-1-trityl-1,8-dihydro-7H-pyrazolo[4,3-g]quinolin-7-one. MS: [M+H]+ m/z 609.

Step 2

TFA (0.2 mL, 2.60 mmol) and triethylsilane (0.012 mL, 0.072 mmol) were added to a stirred solution of 6-benzyl-3-(2-methylpyridin-4-yl)-1-trityl-1,8-dihydro-7H-pyrazolo[4,3-g]quinolin-7-one (44 mg, 0.072 mmol) in DCM (2 mL) and the mixture was stirred at room temperature for 3 h. The mixture was concentrated, diluted with DCM, and treated with saturated sodium bicarbonate solution. The organic layer was separated, concentrated, and purified by flash chromatography to afford 6-benzyl-3-(2-methylpyridin-4-yl)-1,8-dihydro-7H-pyrazolo[4,3-g]quinolin-7-one. MS: [M+H]+ m/z 367. ¹H NMR (600 MHz, DMSO-d6) δ 13.42 (s, 1H), 11.74 (s, 1H), 8.54 (d, J=5.3 Hz, 1H), 8.52 (s, 1H), 7.90 (s, 1H), 7.83 (d, J=4.7 Hz, 1H), 7.82 (s, 1H), 7.39 (s, 1H), 7.22-7.33 (m, 4H), 7.85 (s, 2H), 2.58 (s, 3H).

Example 4

3-(1-methyl-1H-pyrazol-4-yl)-1,8-dihydro-7H-pyrazolo[4,3-g]quinolin-7-one

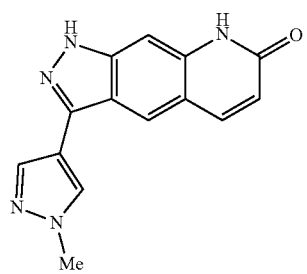 [SMILES: Cn1cc(-c2n[nH]c3cc4[nH]c(=O)ccc4cc23)cn1]

Step 1

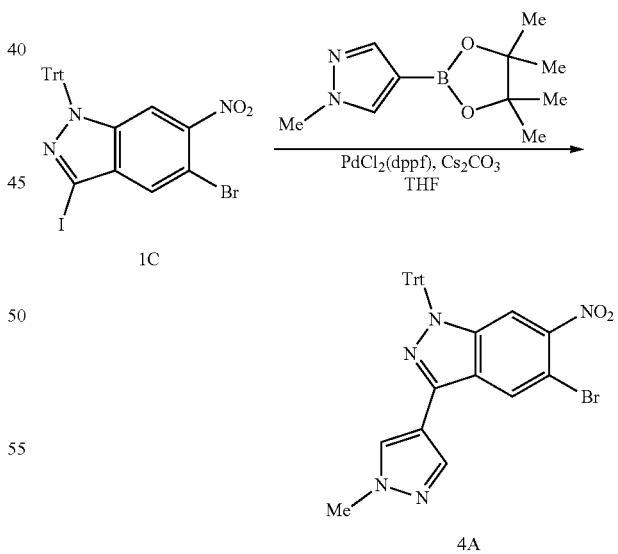

To a mixture of 5-bromo-3-iodo-6-nitro-1-trityl-1H-indazole (20.0 g, 29.5 mmol), 1-methyl-4-(4,4,5,5-tetramethyl-1,3,2-dioxaborolan-2-yl)-1h-pyrazole (6.46 g, 29.5 mmol), and PdCl₂(dppf)-CH₂Cl₂ (3.61 g, 4.42 mmol) were added degassed dioxane (123 mL) and cesium carbonate (38.3 mL, 2 M, 77 mmol). The mixture was purged with nitrogen for 5 min, and heated to 80° C. for 3 h. The mixture was cooled to room temperature, treated with water, and extracted with DCM (×3). The combined organics were washed with brine, dried (sodium sulfate), concentrated, and purified by flash chromatography to afford 5-bromo-3-(1-methyl-1H-pyrazol-4-yl)-6-nitro-1-trityl-1H-indazole. MS: [M+H]+ m/z 564. ¹H NMR (600 MHz, DMSO-d6) δ 8.54 (s, 1H), 8.46 (s, 1H), 7.93 (s, 1H), 7.20-7.38 (m, 15H), 6.65 (s, 1H), 3.91 (s, 3H).

Steps 2-3

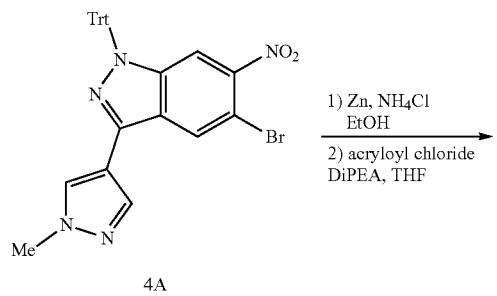

4A

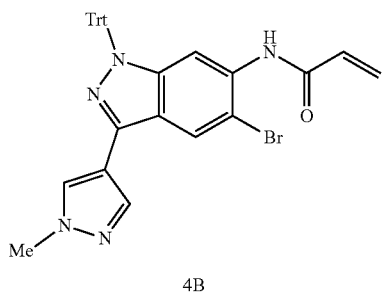

4B

To a stirred solution of 5-bromo-3-(1-methyl-1H-pyrazol-4-yl)-6-nitro-1-trityl-1H-indazole (7.5 g, 12.0 mmol) in ethanol (150 mL) was added Zn (1.96 g, 29.9 mmol) and saturated ammonium chloride solution (50 mL). The mixture was heated to 80° C. for 1 h. Additional Zn (2.0 g, 30 mmol) was added and the mixture was heated to 80° C. for 2 h. The mixture was cooled to room temperature, filtered through a pad of Celite, and concentrated. The residue was diluted with water and extracted with DCM (×3). The combined organics were dried (sodium sulfate), concentrated, and used in the next step without further purification. MS: [M+H]+ m/z 534.

To a stirred solution of the crude product in THF (31 mL) was added diisopropylethylamine (1.2 g, 9.3 mmol) followed by the slow addition of acryloyl chloride (0.42 g, 4.7 mmol). The mixture was left to stir for 3 h, treated with water, and extracted with DCM (×3). The combined organics were dried (sodium sulfate), concentrated, and purified by flash chromatography to afford N-[5-bromo-3-(1-methyl-1H-pyrazol-4-yl)-1-trityl-1H-indazol-6-yl]prop-2-enamide. MS: [M+H]+ m/z 588. ¹H NMR (600 MHz, DMSO-d6) δ 9.41 (s, 1H), 8.35 (s, 1H), 8.29 (s, 1H), 7.84 (s, 1H), 7.22-7.33 (m, 15H), 6.43 (m, 1H), 6.16 (d, J=7.0 Hz, 1H), 5.70 (d, J=10.5 Hz, 1H), 3.90 (s, 3H).

Steps 4-5

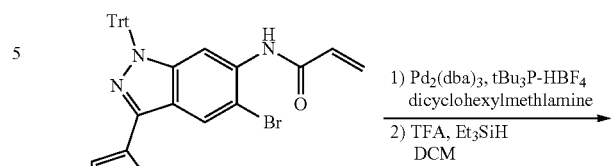

4B

4

A mixture of N-[5-bromo-3-(1-methyl-1H-pyrazol-4-yl)-1-trityl-1H-indazol-6-yl]prop-2-enamide (1.36 g, 2.31 mmol), Pd₂(dba)₃ (0.11 g, 0.12 mmol), tBu₃P-HBF₄ (0.14 g, 0.46 mmol), and dicyclohexylmethylamine (0.54 g, 2.8 mmol) in dioxane (33 mL) was purged with nitrogen for 10 min, heated to 100° C. overnight, and cooled to room temperature. The mixture was treated with water, and extracted with DCM (×3). The combined organics were dried (sodium sulfate), concentrated, and purified by flash chromatography to afford 3-(1-methyl-1H-pyrazol-4-yl)-1-trityl-1,8-dihydro-7H-pyrazolo[4,3-g]quinolin-7-one. MS: [M+H]+ m/z 508.

TFA (0.4 mL) and triethylsilane (0.004 mL, 0.0.02 mmol) were added to a stirred solution of 3-(1-methyl-1H-pyrazol-4-yl)-1-trityl-1,8-dihydro-7H-pyrazolo[4,3-g]quinolin-7-one (20 mg, 0.02 mmol) in DCM (2 mL) and the mixture was stirred at room temperature for 2 h. The mixture was concentrated, and purified by prep-HPLC to afford 3-(1-methyl-1H-pyrazol-4-yl)-1,8-dihydro-7H-pyrazolo[4,3-g]quinolin-7-one trifluoroacetate. MS: [M+H]+ m/z 266. ¹H NMR (600 MHz, DMSO-d6) δ 12.86 (s, 1H), 11.57 (s, 1H), 8.41 (s, 1H), 8.40 (s, 1H), 8.05 (s, 1H), 7.98 (d, J=9.6 Hz, 1H), 7.29 (s, 1H), 6.39 (dd, J=9.5, 1.9 Hz, 1H), 3.95 (s, 3H).

Example 8

8-hydroxy-3-(2-methylpyridin-4-yl)-5,6-dihydro-1H-pyrazolo[4,3-g]quinolin-7(8H)-one

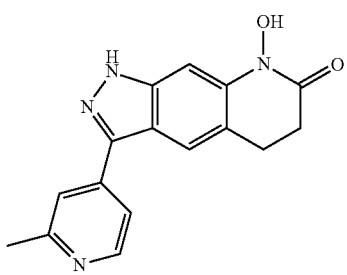 [SMILES: Cc1cc(-c2n[nH]c3cc4c(cc23)CCC(=O)N4O)ccn1]

Step 1

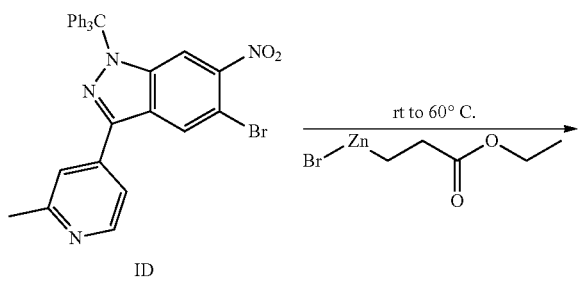

5-bromo-3-(2-methylpyridin-4-yl)-6-nitro-1-trityl-1H-indazole (72.5 mg, 0.19 mmol), 2-(dicyclohexylphosphino)-2',4',6'-triisopropylbiphenyl (6.0 mg, 0.013 mmol) and Pd(OAc)$_2$ (1.4 mg, 6.3 umol) in THF (1.5 mL) was degassed 3 times with N$_2$/vacuum exchange before (3-ethoxy-3-oxopropyl)zinc(II) bromide (0.38 mL, 0.5 M in THF) was added dropwise. The mixture was stirred for 5 minutes at room temperature, and then at 60° C. for 45 minutes. The reaction was quenched with MeOH, the mixture was directly purified by column chromatography on silica gel eluting with gradient up to EtOAc/isohexane=100% to give ethyl 3-(3-(2-methylpyridin-4-yl)-6-nitro-1-trityl-1H-indazol-5-yl)propanoate as light brown syrup.

Step 2

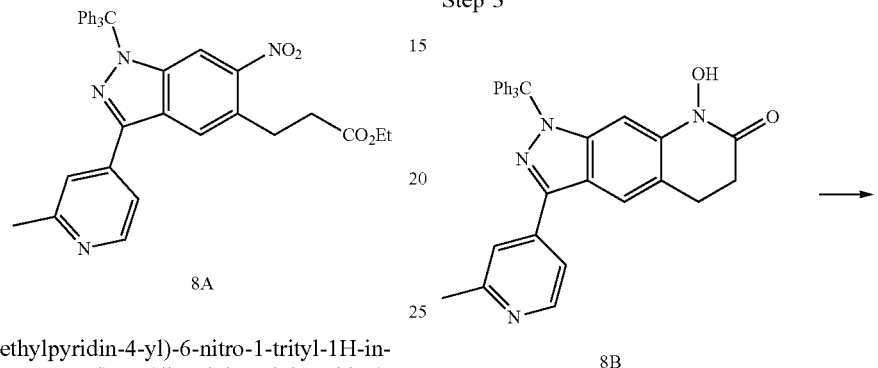

Zinc (107 mg, 1.634 mmol) was added to a stirred mixture ethyl 3-(3-(2-methylpyridin-4-yl)-6-nitro-1-trityl-1H-indazol-5-yl)propanoate (65 mg, 0.109 mmol) in acetic acid (1.5 ml) and the mixture was stirred at 60° C. for 2 h. The mixture was cooled and filtered through a celite pad and washed with ethyl acetate. Solvent was removed and the residue was taken up in ethyl acetate and washed with NaOH (0.1 N) until aqueous layer basic. The combined organic fractions were washed with water, brine, dried (MgSO$_4$), filtered and the solvent was evaporated under reduced pressure. The residue was purified by column chromatography on silica gel eluting with ethyl acetate/hexane gradient up to 80% first, then changed to MeOH/CH$_2$Cl$_2$ gradient up to 20% to give 8-hydroxy-3-(2-methylpyridin-4-yl)-1-trityl-5,6-dihydro-1H-pyrazolo[4,3-g]quinolin-7(8H)-one.

Step 3

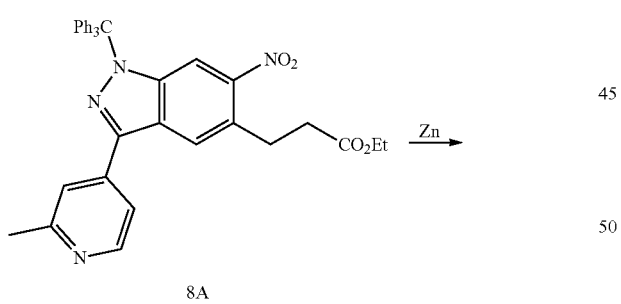

Methanol (9.99 μl, 0.247 mmol) was added to a stirred, mixture of 8-hydroxy-3-(2-methylpyridin-4-yl)-1-trityl-5,6-dihydro-1H-pyrazolo[4,3-g]quinolin-7(8H)-one (26.5 mg, 0.049 mmol) in TFA (1 ml) and the mixture was stirred at room temperature for 2 h. Solvent was removed and the crude was purified with Gilson 0-75% gradient) to give pure 8-hydroxy-3-(2-methylpyridin-4-yl)-5,6-dihydro-1H-pyrazolo[4,3-g]quinolin-7(8H)-one as TFA salt. LCMS: [M+H]+ m/z 295.

Example 9

3-(2-methylpyridin-4-yl)-5,6,7,9-tetrahydroazepino[3,2-f]indazol-8(1H)-one

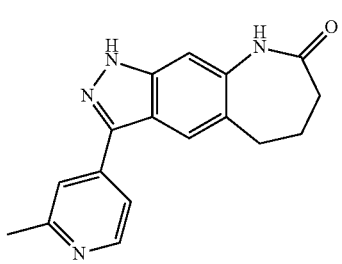 [SMILES: Cc1cc(-c2n[nH]c3cc4c(cc23)CCCC(=O)N4)ccn1]

Steps 1-2

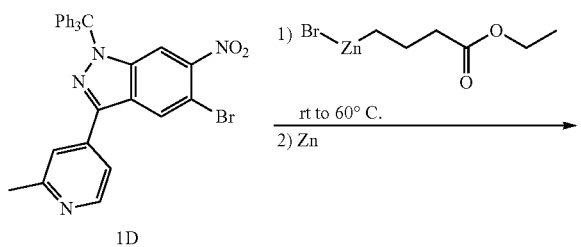

1D

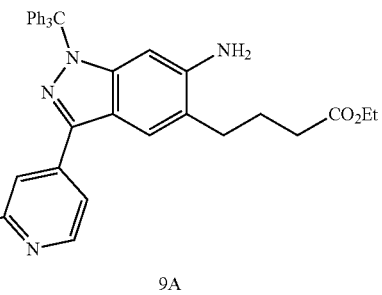

9A

In a manner similar to that described in Example 8 (Step 1), compound 1D was treated with (4-ethoxy-4-oxobutyl) zinc bromide to afford ethyl 4-(3-(2-methylpyridin-4-yl)-6-nitro-1-trityl-1H-indazol-5-yl)butanoate (9A).

Zinc (82 mg, 1.253 mmol) was added to a stirred mixture of ethyl 4-(3-(2-methylpyridin-4-yl)-6-nitro-1-trityl-1H-indazol-5-yl)butanoate (51 mg, 0.084 mmol) in acetic acid (1.5 ml) and the mixture was stirred at 60° C. for 2 h. The mixture was cooled and filtered through a celite pad and washed with ethyl acetate. Solvent was removed and the residue was taken up in ethyl acetate and washed with NaOH (0.1 N) until aqueous layer basic. The combined organic fractions were washed with water, brine, dried (MgSO$_4$), filtered and the solvent was evaporated under reduced pressure. Ethyl 4-(6-amino-3-(2-methylpyridin-4-yl)-1-trityl-1H-indazol-5-yl)butanoate was obtained and used directly for next step.

Step 3

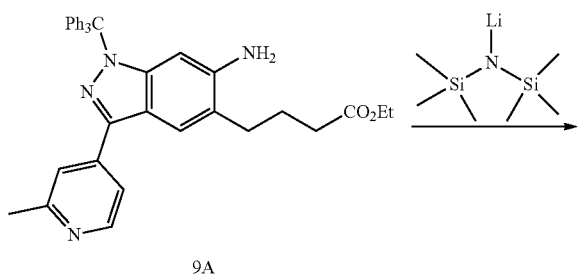

9A

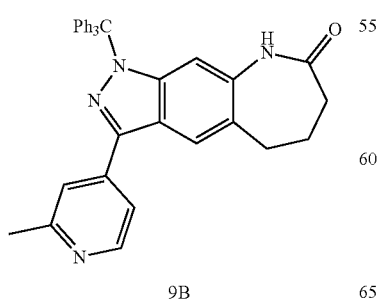

9B

LHMDS (0.181 ml, 0.181 mmol) was added to a stirred, cooled 0° C. mixture of ethyl 4-(6-amino-3-(2-methylpyridin-4-yl)-1-trityl-1H-indazol-5-yl)butanoate (50 mg, 0.086 mmol) in THF (3 ml) and the mixture was stirred at 0° C. for 30 min. TLC (ethyl acetate/hexanes=3/1) showed clean reaction and LCMS clearly showed the product. 0.1 mL of NH$_4$Cl aqueous solution was added to quench the reaction. The mixture was directly purified by column chromatography on silica gel eluting with ethyl acetate/hexane gradient up to 100% first, then changed to MeOH/CH$_2$Cl$_2$ gradient up to 20% to give 3-(2-methylpyridin-4-yl)-1-trityl-5,6,7,9-tetrahydroazepino[3,2-f]indazol-8(1H)-one.

Step 4

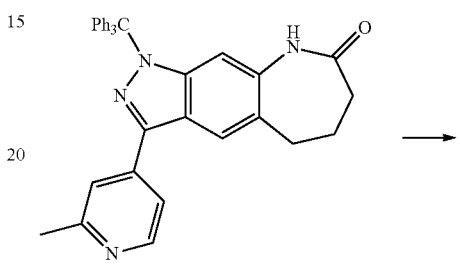

9B

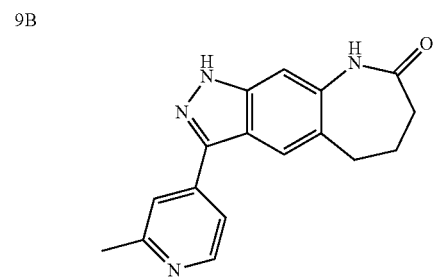

9

Methanol (0.011 ml, 0.281 mmol) was added to a stirred, mixture of 3-(2-methylpyridin-4-yl)-1-trityl-5,6,7,9-tetrahydroazepino[3,2-f]indazol-8(1H)-one (30 mg, 0.056 mmol) in TFA (1 ml) and the mixture was stirred at room temperature for 2 h. LCMS showed no starting material left. Solvent was removed and the crude was purified with Gilson 0-75% gradient) to give pure 3-(2-methylpyridin-4-yl)-5,6,7,9-tetrahydroazepino[3,2-f]indazol-8(1H)-one as TFA salt as light yellow solid. LCMS: [M+H]$^+$ m/z 293.

Example 10

(R)-6-(1-(4-fluorophenyl)ethyl)-3-(2-methylpyridin-4-yl)-5,6-dihydro-1H-pyrazolo[4,3-g]quinazolin-7(8H)-one

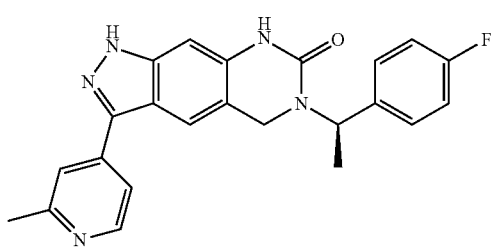 [SMILES: Cc1cc(-c2n[nH]c3cc4c(cc23)CN([C@H](C)c2ccc(F)cc2)C(=O)N4)ccn1]

Step 1

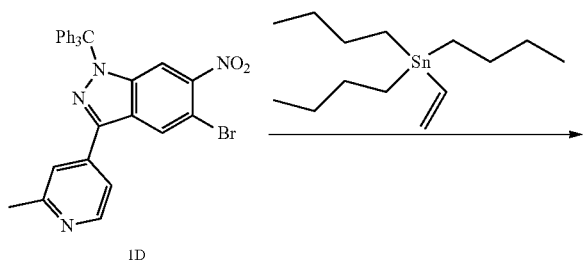

1D

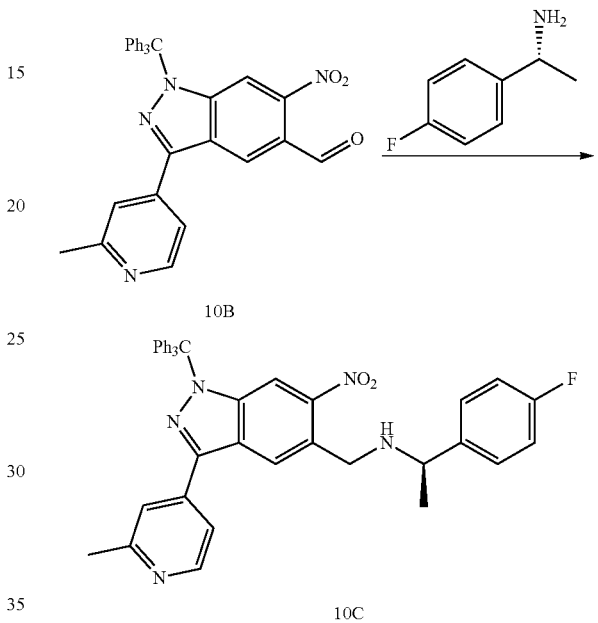

A mixture of 5-bromo-3-(2-methylpyridin-4-yl)-6-nitro-1-trityl-1H-indazole (400 mg, 0.695 mmol), tetrakis(triphenylphosphine)palladium(0) (80 mg, 0.070 mmol) and lithium chloride (88 mg, 2.085 mmol), 1,4-dioxane (3.5 mL), tributyl vinyltin (0.244 mL, 0.834 mmol) and 2,6-di-tert-butyl-4-methylphenol (1.532 mg, 6.95 μmol) were degassed with vacuum/N2 exchanged for 4 times. The resultant mixture was kept stirring at 88° C. for overnight. The crude was cooled and directly purified by column chromatography on silica gel, eluting with 0%-60% EtOAc/isohexane to provide 3-(2-methylpyridin-4-yl)-6-nitro-1-trityl-5-vinyl-1H-indazole.

Step 2

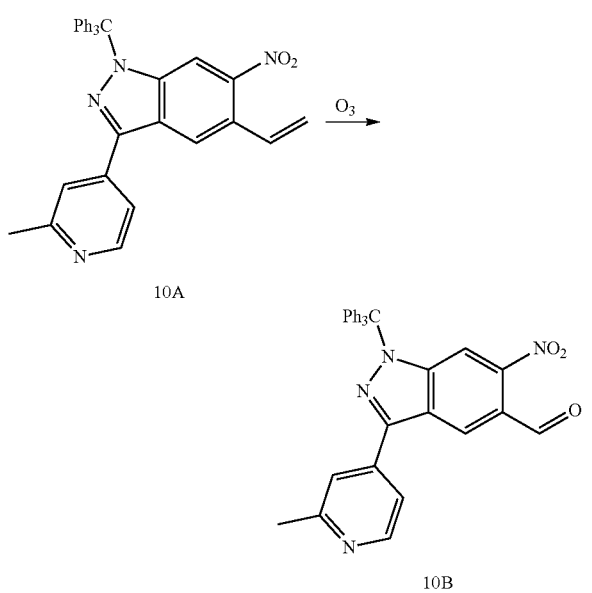

O₃ was bubbled through a solution of 3-(2-methylpyridin-4-yl)-6-nitro-1-trityl-5-vinyl-1H-indazole (0.21 g, 0.402 mmol) in DCM (5 ml) and MeOH (2.5 ml) at −78° C. for 10 minutes. LCMS and TLC (50% ethyl acetate/hexanes) showed no starting material left. N₂ was bubbled through the solution for 5 minutes before Me₂S was added (0.3 mL) and the mixture was stirred for 3 hours. The reaction was taken up in ethyl acetate/NH₄Cl aqueous solution. The organic phases was dried over Mg₂SO₄, filtered and solvent was removed to give 3-(2-methylpyridin-4-yl)-6-nitro-1-trityl-1H-indazole-5-carbaldehyde.

Step 3

(R)-1-(4-Fluorophenyl)ethylamine (33.2 mg, 0.238 mmol) was added to a stirred mixture of 3-(2-methylpyridin-4-yl)-6-nitro-1-trityl-1H-indazole-5-carbaldehyde (50 mg, 0.095 mmol) in DCE (2) and the mixture was stirred at room temperature for 10 min. before sodium triacetoxyborohydride (101 mg, 0.477 mmol) was added. The mixture was stirred at room temp. overnight. The mixture taken up in ethyl acetate (50 mL), washed with aqueous sodium hydrogen carbonate (saturated, 3×15 mL), dried (MgSO₄), filtered and the solvent was evaporated under reduced pressure to give a mixture of (R)-1-(4-fluorophenyl)-N-((3-(2-methylpyridin-4-yl)-6-nitro-1-trityl-1H-indazol-5-yl)methyl)ethanamine and an unknown by-product as light yellow foam, which was used as it for next step.

Step 4

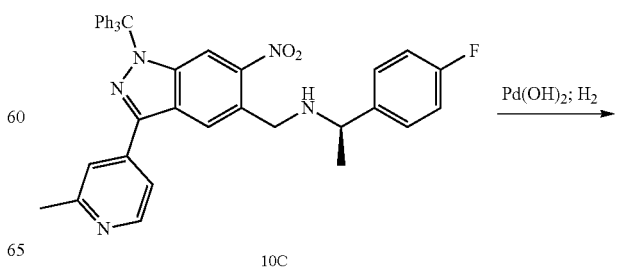

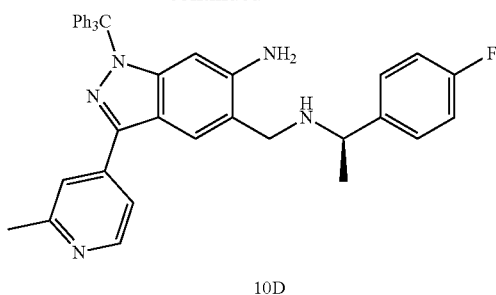

10D

Palladium hydroxide on carbon (20 mg, 0.028 mmol) was added to a stirred mixture of (R)-1-(4-fluorophenyl)-N-((3-(2-methylpyridin-4-yl)-6-nitro-1-trityl-1H-indazol-5-yl)methyl)-ethanamine (65 mg, 0.100 mmol) in EtOH (3 ml) and the mixture was H₂/vacuum exchanged for 3 times and stirred at room temperature overnight. The reaction was worked up by filtration through a short celite pad and washed with ethyl acetate. Solvent was removed to give the crude product which was used directly for next step.

Step 5

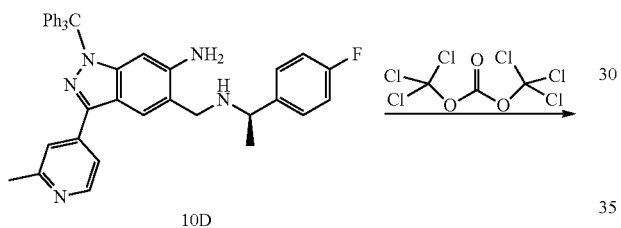

10D

10E (R)-5-(((1-(4-fluorophenyl)ethyl)amino)methyl)-3-(2-methylpyridin-4-yl)-1-trityl-1H-indazol-6-amine (37.2 mg, 0.060 mmol) was added to a stirred mixture of triphosgene (7.2 mg, 0.024 mmol) in dioxane (1.5 ml) and the mixture was stirred at room temperature for 45 min. The mixture was quenched with MeOH and NEt₃ (drops). The mixture was direct applied to silica gel column eluting with Hexane/ethyl acetate 100-0%, then ethyl acetate/MeOH 100-70%, to give (R)-6-(1-(4-fluorophenyl)ethyl)-3-(2-methylpyridin-4-yl)-1-trityl-5,6-dihydro-1H-pyrazolo[4,3-g]quinazolin-7(8H)-one.

Step 6

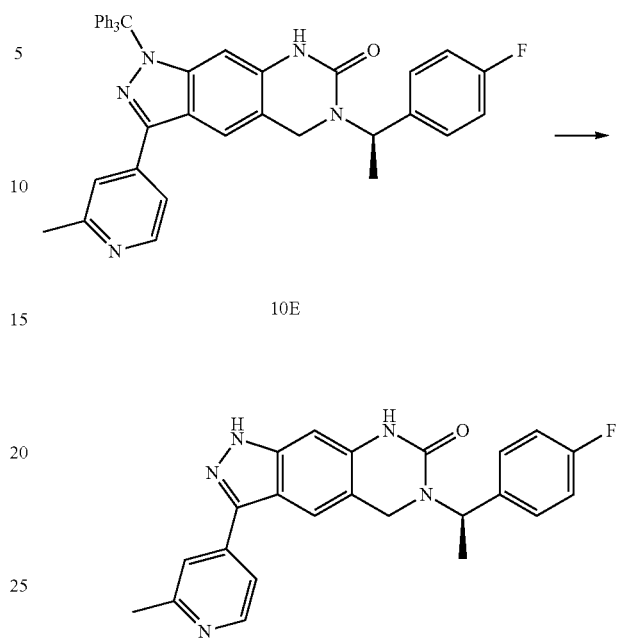

10E

10

MeOH (1.760 μl, 0.043 mmol) was added to a stirred mixture of (R)-6-(1-(4-fluorophenyl)ethyl)-3-(2-methylpyridin-4-yl)-1-trityl-5,6-dihydro-1H-pyrazolo[4,3-g]quinazolin-7(8H)-one (28 mg, 0.043 mmol) in TFA (1 ml) and the mixture was stirred at room temperature for 45 min. The solvent was removed and the crude was diluted with DCM and 2M NH3 in MeOH and purified with PTLC (ethyl acetate/MeOH=95/5) to give (R)-6-(1-(4-fluorophenyl)ethyl)-3-(2-methylpyridin-4-yl)-5,6-dihydro-1H-pyrazolo[4,3-g]quinazolin-7(8H)-one. LCMS: [M+H]⁺ m/z 402.

Example 11

7-(4-fluorobenzyl)-9-hydroxy-3-(2-methylpyridin-4-yl)-5,6,7,9-tetrahydro-[1,3]diazepino[5,4-f]indazol-8(1H)-one

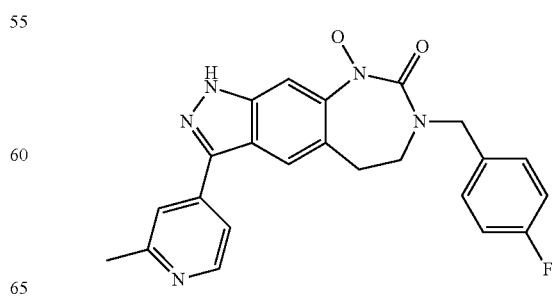

Step 1

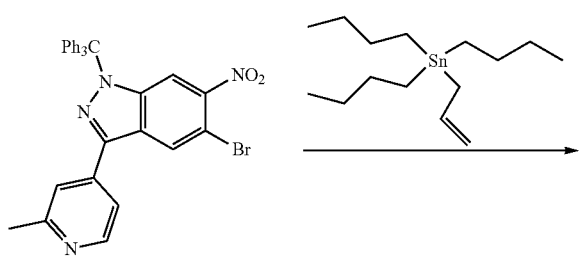

1D

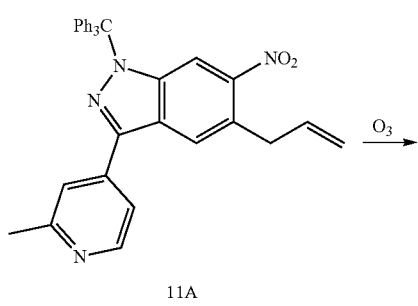

11A

The mixture of 5-bromo-3-(2-methylpyridin-4-yl)-6-nitro-1-trityl-1H-indazole (400 mg, 0.695 mmol), tetrakis(triphenylphosphine)palladium(0) (80 mg, 0.070 mmol), lithium chloride (88 mg, 2.085 mmol), allyltributyltin (0.258 ml, 0.834 mmol) and 2,6-di-tert-butyl-4-methylphenol (1.532 mg, 6.95 μmol) were degassed with vacuum/N₂ exchanged for 4 times. The resultant mixture was kept stirring at 88° C. for overnight. The crude was cooled and directly purified by column chromatography on silica gel, eluting with EtOAc/isohexane=0%-60% to give 5-allyl-3-(2-methylpyridin-4-yl)-6-nitro-1-trityl-1H-indazole.

Step 2

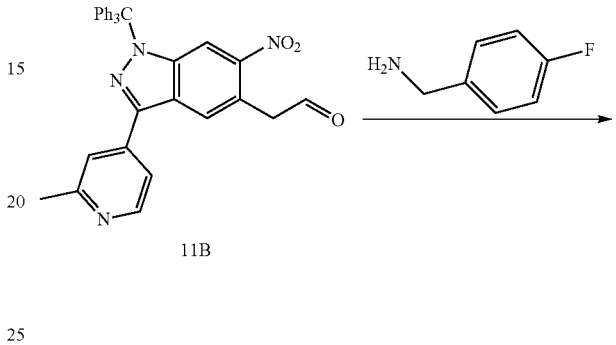

11A

11B

O₃ was bubbled through a solution of 5-allyl-3-(2-methylpyridin-4-yl)-6-nitro-1-trityl-1H-indazole (260 mg, 0.485 mmol) in DCM (5 ml) and MeOH (2.5 ml) at −78° C. for 10 minutes, LCMS and TLC (ethyl acetate/hexanes=1/1) showed no starting material left. N2 was bubbled through the solution for 5 minutes before Me₂S was added (0.3 mL) and the mixture was stirred for 3 hours. The reaction was worked with with ethyl acetate/NH₄Cl aqueous solution. The organic phases was dried over Mg₂SO₄, filtered and solvent was removed to give crude 2-(3-(2-methylpyridin-4-yl)-6-nitro-1-trityl-1H-indazol-5-yl)acetaldehyde.

Step 3

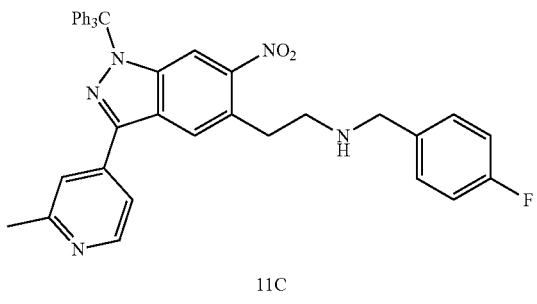

11B

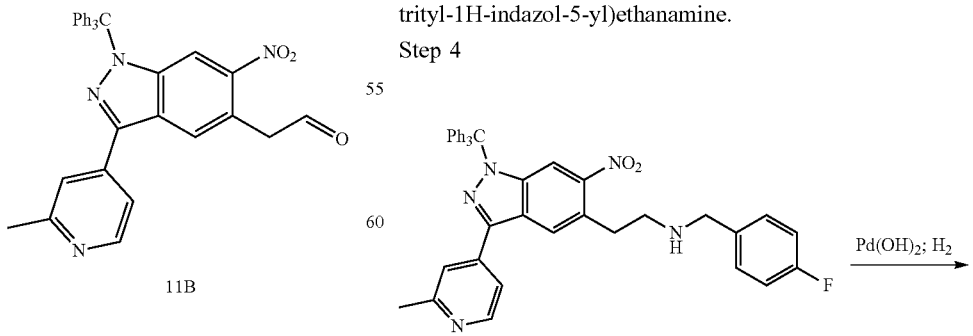

11C

4-Fluorobenzylamine (65.1 mg, 0.520 mmol) was added to a stirred mixture of 2-(3-(2-methylpyridin-4-yl)-6-nitro-1-trityl-1H-indazol-5-yl)acetaldehyde (140 mg, 0.260 mmol) in DCE (5 ml) and the mixture was stirred at room temperature for 10 min. before sodium triacetoxyborohydride (275 mg, 1.300 mmol) was added. The mixture was stirred at room temp. overnight. The reaction mixture was directly purified by column chromatography on silica gel eluting with EtOAc/MeOH gradient from 1% to 30% to give N-(4-fluorobenzyl)-2-(3-(2-methylpyridin-4-yl)-6-nitro-1-trityl-1H-indazol-5-yl)ethanamine.

Step 4

-continued

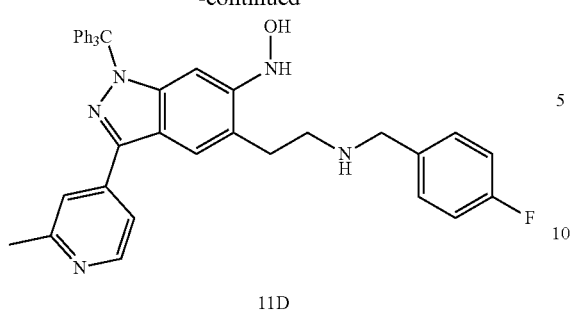

11D

Palladium hydroxide on carbon (30 mg, 0.043 mmol) was added to a stirred mixture of N-(4-fluorobenzyl)-2-(3-(2-methylpyridin-4-yl)-6-nitro-1-trityl-1H-indazol-5-yl)ethanamine (96 mg, 0.148 mmol) in ethanol (5 ml) and the mixture was stirred at room temperature overnight. The reaction was worked up by filtration through a short celite pad and washed with ethyl acetate. The solvent was removed to give the crude which was used directly for next step.

Step 5

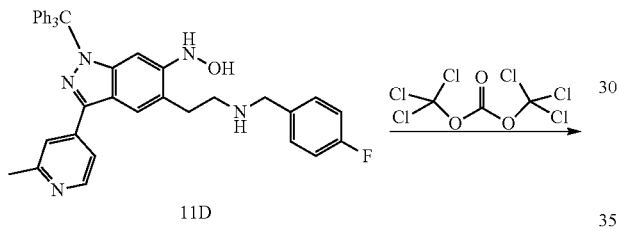

11D

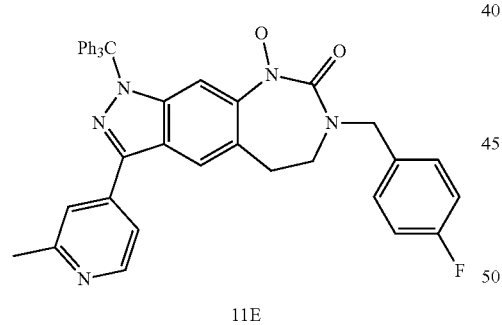

11E

Triphosgene (17.57 mg, 0.059 mmol) was added to a stirred mixture of N-(4-fluorobenzyl)-2-(6-(hydroxyamino)-3-(2-methylpyridin-4-yl)-1-trityl-1H-indazol-5-yl)ethanamine (91 mg, 0.148 mmol) in dioxane (3 ml) and the mixture was stirred at room temperature for 45 min. The reaction was quenched with MeOH and NEt$_3$ (drops). The mixture was taken up in DCM and washed with NaOH (1 N), then was washed with water, and brine, dried (MgSO$_4$), filtered and the solvent was evaporated under reduced pressure. The mixture was purified by PTLC (ethyl acetate/hexanes=4/1) to give to give 7-(4-fluorobenzyl)-9-hydroxy-3-(2-methylpyridin-4-yl)-1-trityl-5,6,7,9-tetrahydro-[1,3]diazepino[5,4-f]indazol-8(1H)-one.

Step 6

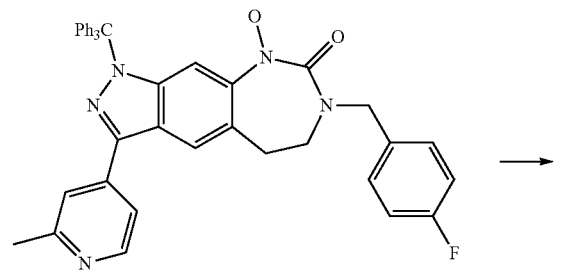

11E

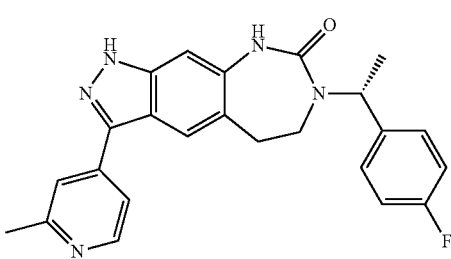 [SMILES: Cc1cc(-c2n[nH]c3cc4c(cc23)CCN([C@H](C)c2ccc(F)cc2)C(=O)N4)ccn1]

11

MeOH (1.717 µl, 0.042 mmol) was added to a stirred mixture of 7-(4-fluorobenzyl)-9-hydroxy-3-(2-methylpyridin-4-yl)-1-trityl-5,6,7,9-tetrahydro-[1,3]diazepino[5,4-f]indazol-8(1H)-one (28 mg, 0.042 mmol) in TFA (1 ml) and the mixture was stirred at room temperature for 45 min. LCMS and TLC (DCM/MeOH(2M NH$_3$)=95/5) showed no starting material left. Solvent was removed and the crude was purified with Gilson (CH$_3$CN/H$_2$O/TFA, 10-90% gradient) to give 7-(4-fluorobenzyl)-9-hydroxy-3-(2-methylpyridin-4-yl)-5,6,7,9-tetrahydro-[1,3]diazepino-[5,4-f]indazol-8(1H)-one as the TFA salt. LCMS: [M+H]$^+$ m/z 418.

Example 12

(R)-7-(1-(4-fluorophenyl)ethyl)-3-(2-methylpyridin-4-yl)-5,6,7,9-tetrahydro-[1,3]diazepino[5,4-f]indazol-8(1H)-one Steps 1-2

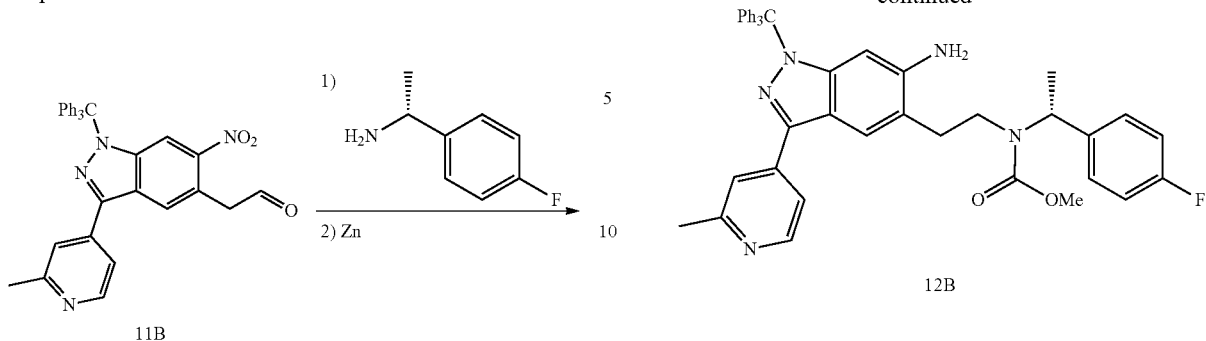

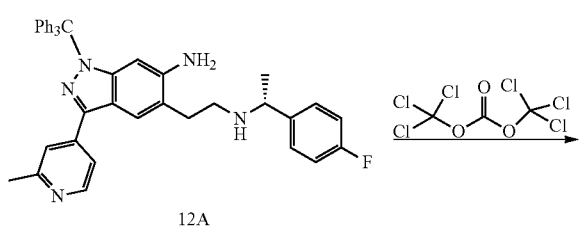

In a manner similar to that described in Example 11 (Step 3), 2-(3-(2-methylpyridin-4-yl)-6-nitro-1-trityl-1H-indazol-5-yl)acetaldehyde was reacted with (R)-1-(4-fluorophenyl)ethanamine and sodium triacetoxyborohydride to provide (R)-1-(4-fluorophenyl)-N-(2-(3-(2-methylpyridin-4-yl)-6-nitro-1-trityl-1H-indazol-5-yl)ethyl)ethanamine.

Zinc (59.3 mg, 0.907 mmol) was added to a stirred mixture of (R)-1-(4-fluorophenyl)-N-(2-(3-(2-methylpyridin-4-yl)-6-nitro-1-trityl-1H-indazol-5-yl)ethyl)ethanamine (40 mg, 0.060 mmol) in acetic acid (1.5 ml) and the mixture was stirred at 60° C. for 90 min. The mixture was filtered through a short pad of celite washing with ethyl acetate and the solvent was removed. The residue was taken up in ethyl acetate and washed with aqueous sodium hydrogen carbonate (saturated, 3×20 mL), water and brine, dried (MgSO₄), filtered and the solvent was evaporated under reduced pressure. The crude (R)-5-(2-((1-(4-fluorophenyl)ethyl)amino)ethyl)-3-(2-methylpyridin-4-yl)-1-trityl-1H-indazol-6-amine was used for next step directly.

Step 3

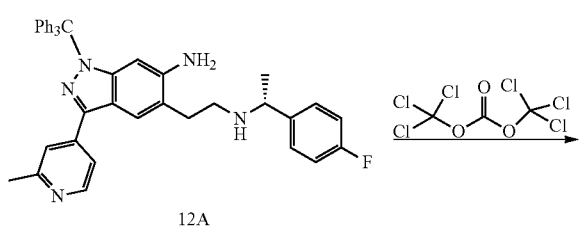

Triphosgene (6.25 mg, 0.021 mmol) was added to a stirred mixture of (R)-5-(2-((1-(4-fluorophenyl)ethyl)amino)ethyl)-3-(2-methylpyridin-4-yl)-1-trityl-1H-indazol-6-amine (38 mg, 0.060 mmol) in dioxane (2) and the mixture was stirred at room temperature for 30 min. The reaction was quenched with MeOH (1 mL)/NEt₃ (0.2 mL). The mixture was directly loaded to a silica gel column eluting with ethyl acetate/Hexane 0-100% gradient and the MeOH/ethyl acetate gradient 0-30% to give of (R)-methyl (2-(6-amino-3-(2-methylpyridin-4-yl)-1-trityl-1H-indazol-5-yl)ethyl)(1-(4-fluorophenyl)ethyl)carbamate (16 mg) which was used for next step directly.

Step 4

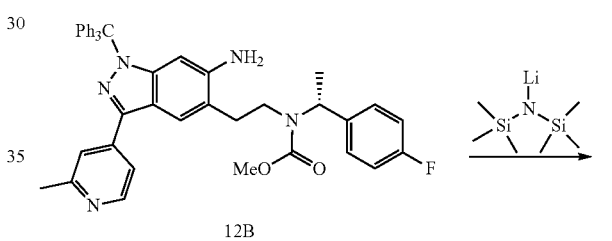

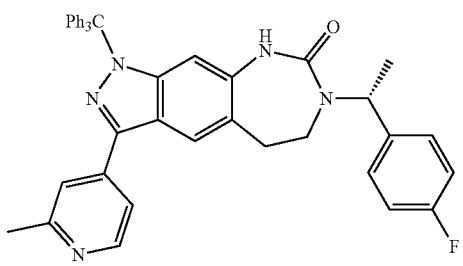

LHMDS (0.056 ml, 0.056 mmol) was added to a stirred, cooled 0° C. mixture of (R)-methyl (2-(6-amino-3-(2-methylpyridin-4-yl)-1-trityl-1H-indazol-5-yl)ethyl)(1-(4-fluorophenyl)ethyl)carbamate (16 mg, 0.023 mmol) in THF (1.5 ml) and the mixture was heated at 80° C. for 4 days. The mixture was cooled and purified with PTLC (ethyl acetate/Hexane=3/2) to give (R)-7-(1-(4-fluorophenyl)ethyl)-3-(2-methylpyridin-4-yl)-1-trityl-5,6,7,9-tetrahydro-[1,3]diazepino[5,4-f]indazol-8(1H)-one.

Step 5

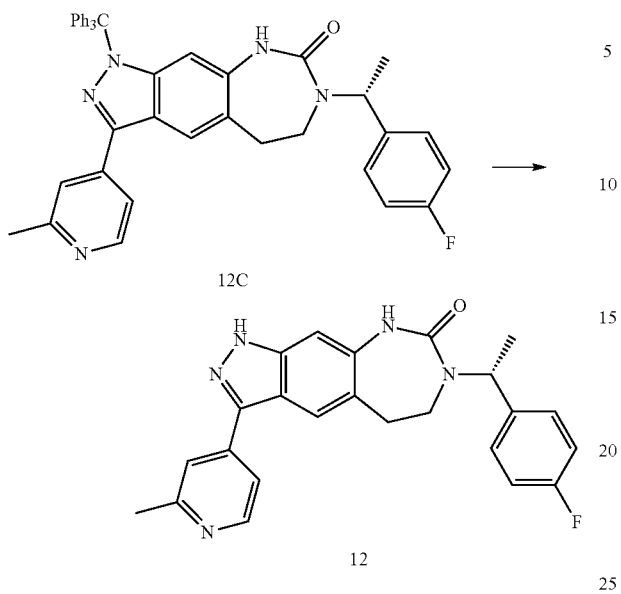

12C

12

Triethylsilane (0.05 ml) was added to a stirred mixture of (R)-7-(1-(4-fluorophenyl)ethyl)-3-(2-methylpyridin-4-yl)-1-trityl-5,6,7,9-tetrahydro-[1,3]diazepino[5,4-f]indazol-8(1H)-one (3.5 mg, 5.32 μmol) in TFA (0.5 ml) and the mixture was stirred at room temperature for 1 h. The solvent was removed and crude was purified by preparative HPLC Reverse phase (C-18), eluting with Acetonitrile/Water+0.1% TFA 10-90% to give (R)-7-(1-(4-fluorophenyl)ethyl)-3-(2-methylpyridin-4-yl)-5,6,7,9-tetrahydro-[1,3]diazepino[5,4-f]indazol-8(1H)-one 2,2,2-trifluoroacetate. LCMS: [M+H]+ m/z 416.

Example 13

3-(2-methylpyridin-4-yl)-5,6-dihydro-1H-pyrazolo[4,3-g]quinazolin-7(8H)-one

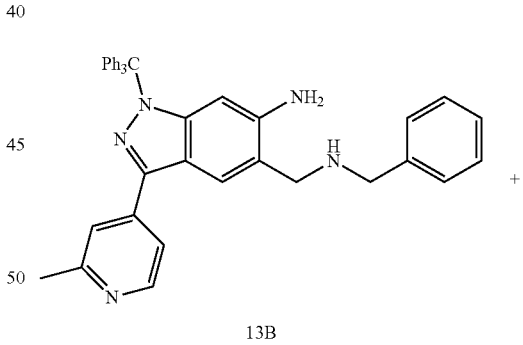

Step 1

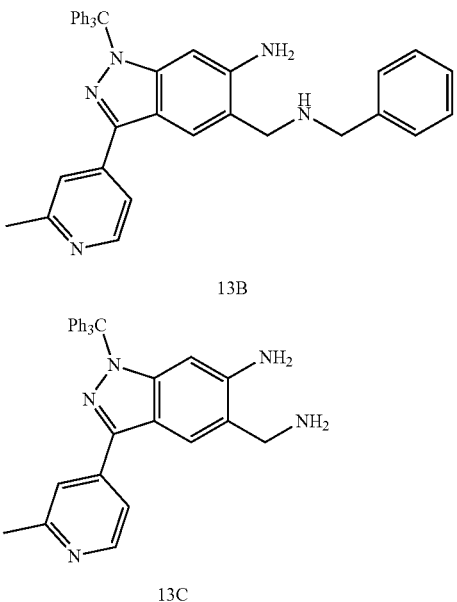

13B

13C

Palladium hydroxide on carbon (18 mg, 0.026 mmol) was added to a stirred mixture of N-benzyl-1-(3-(2-methylpyridin-4-yl)-6-nitro-1-trityl-1H-indazol-5-yl)methanamine (50 mg, 0.081 mmol, prepared from 10B and benzylamine as described in Example 10, Step 3) in methanol (2 ml) and DCM (2 ml) and the mixture was H₂/vacuum exchanged for 3 times and stirred at room temperature overnight. The reaction was filtered through a short celite pad and washed with ethyl acetate. Solvent was removed to give the crude (mixture of desired product and over-reduced byproduct) which was used directly for next step.

Step 2

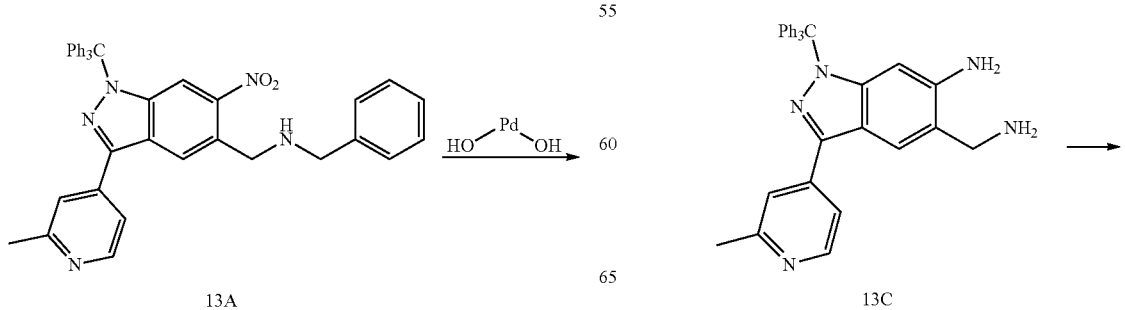

13A    13B    13C

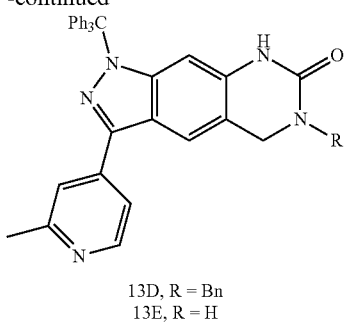

13D, R = Bn
13E, R = H

Triphosgene (15.58 mg, 0.052 mmol) was added to a stirred mixture of 5-((benzylamino)methyl)-3-(2-methylpyridin-4-yl)-1-trityl-1H-indazol-6-amine and 5-(aminomethyl)-3-(2-methylpyridin-4-yl)-1-trityl-1H-indazol-6-amine (41 mg) in dioxane (2.5 ml) and DCM (1.5 ml) and the mixture was stirred at room temperature for 30 min. The reaction was quenched with MeOH (1 mL)/NEt₃ (0.2 mL). The mixture was directly loaded to silica gel column eluting with ethyl acetate/Hexane 0-100% gradient and the MeOH/ethyl acetate gradient 0-30% to give 6-benzyl-3-(2-methylpyridin-4-yl)-1-trityl-5,6-dihydro-1H-pyrazolo[4,3-g]quinazolin-7(8H)-one and 3-(2-methylpyridin-4-yl)-1-trityl-5,6-dihydro-1H-pyrazolo[4,3-g]quinazolin-7(8H)-one.

Step 3

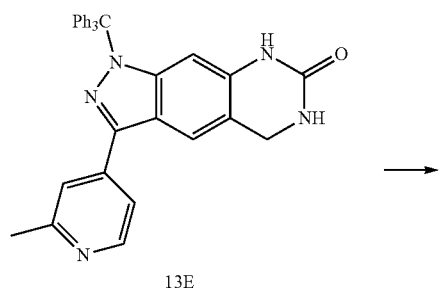

13E

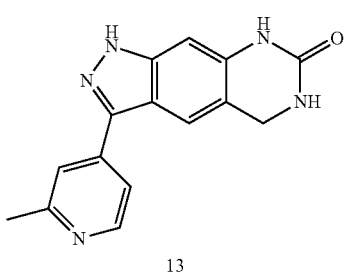

13

Et₃SiH (0.05 ml) was added to a stirred mixture of 3-(2-methylpyridin-4-yl)-1-trityl-5,6-dihydro-1H-pyrazolo[4,3-g]quinazolin-7(8H)-one (16 mg, 0.031 mmol) in TFA (1 ml) and the mixture was stirred at room temperature for 15 minutes. Solvent was removed and crude was purified with preparative HPLC Reverse phase (C-18), eluting with Acetonitrile/Water+0.1% TFA10-90% to give 3-(2-methylpyridin-4-yl)-5,6-dihydro-1H-pyrazolo[4,3-g]quinazolin-7(8H)-one 2,2,2-trifluoroacetate. LCMS: [M+H]⁺ m/z 280.

Example 15

(R)-3-(1-methyl-1H-benzo[d][1,2,3]triazol-6-yl)-6-(1-phenylethyl)-1H-pyrazolo[4,3-g]quinazoline-5,7(6H,8H)-dione

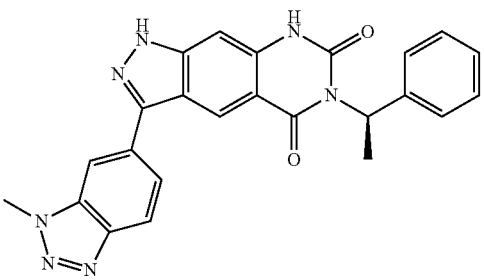 [SMILES: C[C@H](c1ccccc1)n1c(=O)[nH]c2cc3[nH]nc(-c4ccc5nnn(C)c5c4)c3cc2c1=O]

Step 1

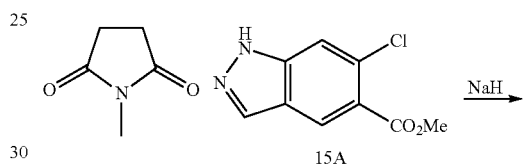

NaH (427 mg, 10.68 mmol) was added to a stirred, room temperature mixture of methyl 6-chloro-1H-indazole-5-carboxylate (1500 mg, 7.12 mmol) in DMF (20 mL) at 0° C. and the mixture was stirred at room temperature for 15 min. followed by the addition of N-iodosuccinimide (2403 mg, 10.68 mmol), the mixture was kept stirring at room temp for overnight. The reaction was quenched with slow addition of NH₄Cl solution and EtOAc. The organic phase was washed with saturated Na₂S₂O₃ and NaHCO₃ solution, then water and brine. The mixture was dried with MgSO₄ and filtered, washed with ethyl acacate. The mixture was purified by column chromatography on silica gel eluting with EtOAc/isohexane=0%-60% to give methyl 6-chloro-3-iodo-1H-indazole-5-carboxylate.

Step 2

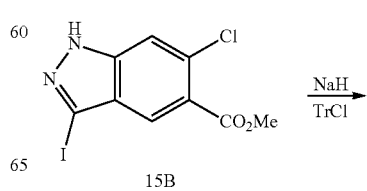

15B

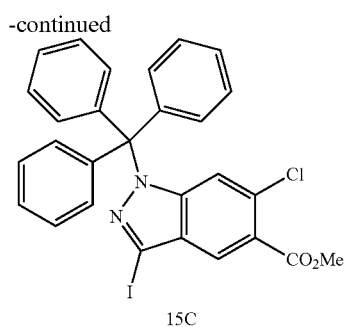

15C

Sodium hydride (0.357 g, 8.91 mmol) was added to a stirred, cooled 0° C. mixture of methyl 6-chloro-3-iodo-1H-indazole-5-carboxylate (2 g, 5.94 mmol) in DMF (30 ml) and the mixture was stirred at 0° C. for 30 min. before (chloromethanetriyl)tribenzene (1.823 g, 6.54 mmol) was added. The mixture was stirred at room temperature overnight. TLC (hexane/EtOAc=6/1) showed 3 spots. The reaction was quenched with NH₄Cl solution and 0.5 M HCl diluted with EtOAc. The mixture was washed with water (3×50 mL), brine, dried (MgSO₄), filtered and the solvent was evaporated under reduced pressure. The residue was purified by column chromatography on silica gel eluting with EtOAc/isohexane gradient from 0% to 100% to give methyl 6-chloro-3-iodo-1-trityl-1H-indazole-5-carboxylate.

Step 3

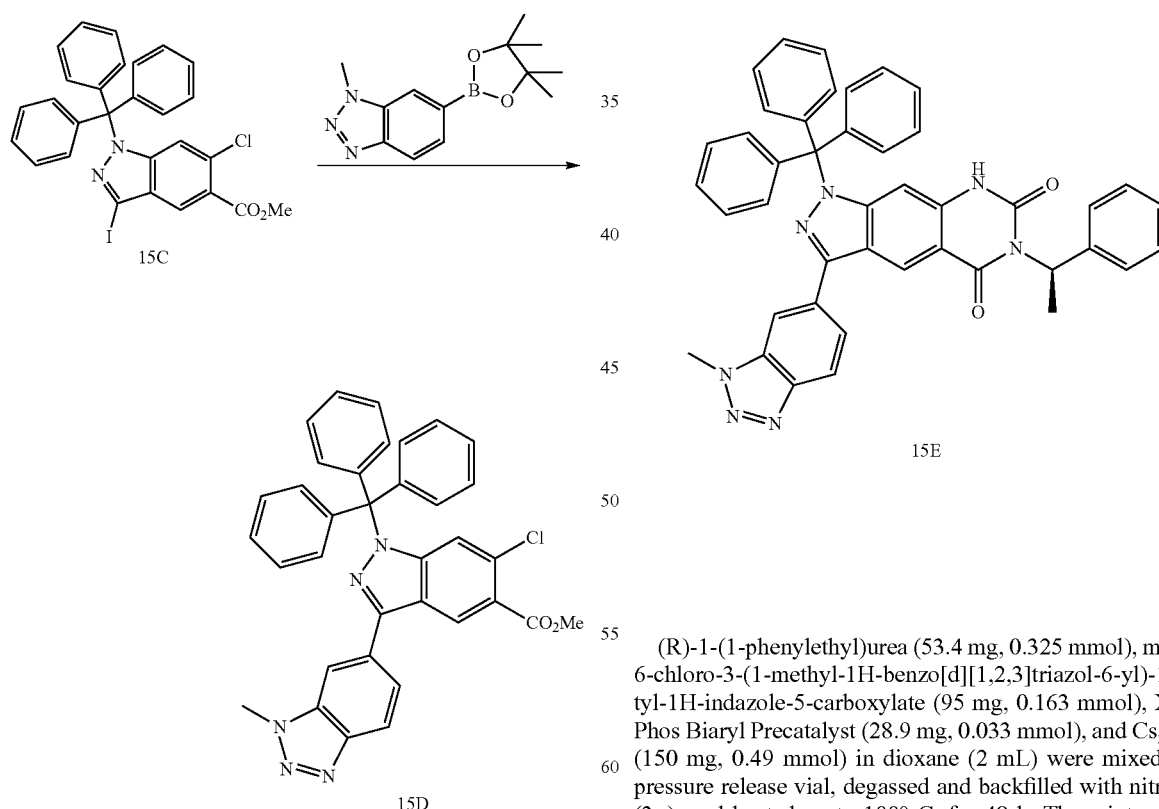

1-methyl-6-(4,4,5,5-tetramethyl-1,3,2-dioxaborolan-2-yl)-1H-benzo[d][1,2,3]triazole (161 mg, 0.622 mmol), methyl 6-chloro-3-iodo-1-trityl-1H-indazole-5-carboxylate (300 mg, 0.518 mmol), sodium bicarbonate (131 mg, 1.555 mmol) in water (2 ml) and 1,1'-bis(diphenylphosphino) ferrocene-palladium(II)dichloride dichloromethane complex (85 mg, 0.104 mmol) were mixed in a pressure release vial in dioxane (6 mL). The mixture was degassed and backfilled with nitrogen (3×), dioxane (6 mL) was added, and the resultant mixture was degassed and backfilled with nitrogen (3×), and heated up to 80° C. in a microwave reactor for 30 minutes. The mixture was cooled, and directly purified by column chromatography on silica gel eluting with gradient EtOAc/isohexane=0-80% to give methyl 6-chloro-3-(1-methyl-1H-benzo[d][1,2,3]triazol-6-yl)-1-trityl-1H-indazole-5-carboxylate.

Step 4

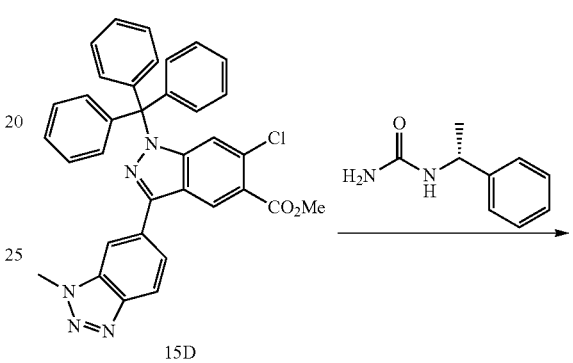

(R)-1-(1-phenylethyl)urea (53.4 mg, 0.325 mmol), methyl 6-chloro-3-(1-methyl-1H-benzo[d][1,2,3]triazol-6-yl)-1-trityl-1H-indazole-5-carboxylate (95 mg, 0.163 mmol), XantPhos Biaryl Precatalyst (28.9 mg, 0.033 mmol), and Cs₂CO₃ (150 mg, 0.49 mmol) in dioxane (2 mL) were mixed in a pressure release vial, degassed and backfilled with nitrogen (3×), and heated up to 100° C. for 48 h. The mixture was cooled and loaded to silica gel column and airpurged for 5 min, then eluted with EtOAc/isohexane=80→100% to give (R)-3-(1-methyl-1H-benzo[d][1,2,3]triazol-6-yl)-6-(1-phenylethyl)-1-trityl-1H-pyrazolo[4,3-g]quinazoline-5,7(6H,8H)-dione.

Step 5

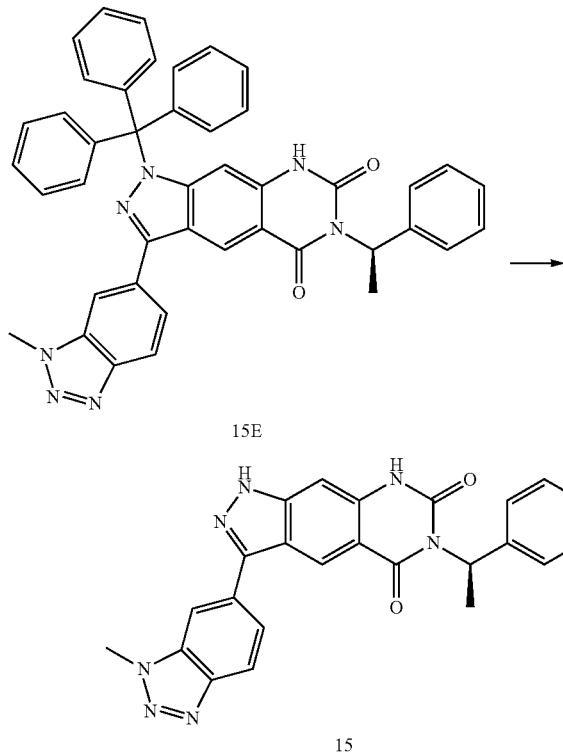

TFA (1.5 ml) and Et₃SiH (0.75 ml) were added to (R)-3-(1-methyl-1H-benzo[d][1,2,3]triazol-6-yl)-6-(1-phenylethyl)-1-trityl-1H-pyrazolo[4,3-g]quinazoline-5,7(6H,8H)-dione (52 mg, 0.076 mmol). The mixture was stirred at room temperature for 15 min. Solvent was removed and the crude was purified with gilson reverse phase HPLC (C-8), eluting with Acetonitrile/Water+0.1% TFA10-90% to give (R)-3-(1-methyl-1H-benzo[d][1,2,3]triazol-6-yl)-6-(1-phenylethyl)-1H-pyrazolo[4,3-g]quinazoline-5,7(6H,8H)-dione 2,2,2-trifluoroacetate as a light yellow solid. LCMS: [M+H]⁺ m/z 438.

Example 24

3-morpholino-1H-pyrazolo[4,3-g]quinolin-7(8H)-one

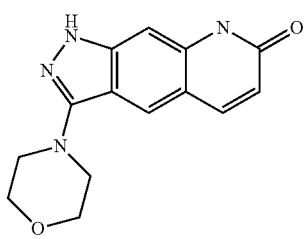 [SMILES: O=c1ccc2cc3c(N4CCOCC4)n[nH]c3cc2[nH]1]

Step 1

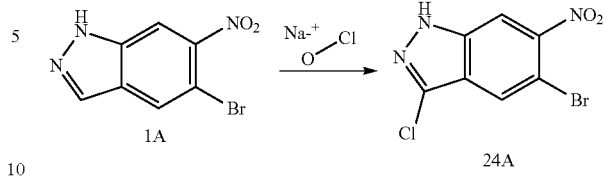

To a suspension of 5-bromo-6-nitro-1H-indazole (2.00 g, 8.26 mmol) in EtOH (20 ml) was added sodium hypochlorite (11.77 ml, 24.79 mmol) dropwise in one portion. LC showed complete conversion at rt after 15 min. The reaction was quenched with 10% Na₂SO₃ (20 mL) and stirred overnight. The mixture was then diluted with water (80 mL), extracted with EtOAc (50 mL×3), washed with brine, dried over Na₂SO₄, and concentrated to give 5-bromo-3-chloro-6-nitro-1H-indazole the crude product which was used without further purification.

Steps 2-3

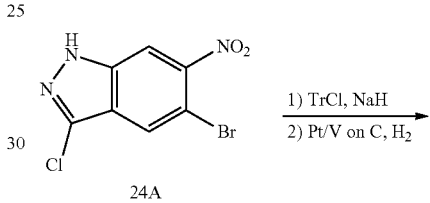

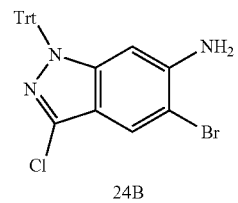

In a manner similar to that described in Example 1 (Step 2), 5-bromo-3-chloro-6-nitro-1H-indazole was treated with TrCl and NaH to provide 5-bromo-3-chloro-6-nitro-1-trityl-1H-indazole.

To a solution of provide 5-bromo-3-chloro-6-nitro-1-trityl-1H-indazole (5.0 g, 9.64 mmol) in MeOH (25 ml) and DCM (25 ml) was added 3% Pt on carbon doped with 0.6% V (1.880 g) and the resulting mixture was stirred under a hydrogen balloon for 6 h. The reaction mixture was diluted with 25 mL of DCM and filtered through a celite pad and washed with additional DCM. After concentrating the filtrate down to about 15 mL left (mainly MeOH), precipitation occurred. The precipitates were filtered and washed with MeOH to give 5-bromo-3-chloro-1-trityl-1H-indazol-6-amine.

Steps 4-5

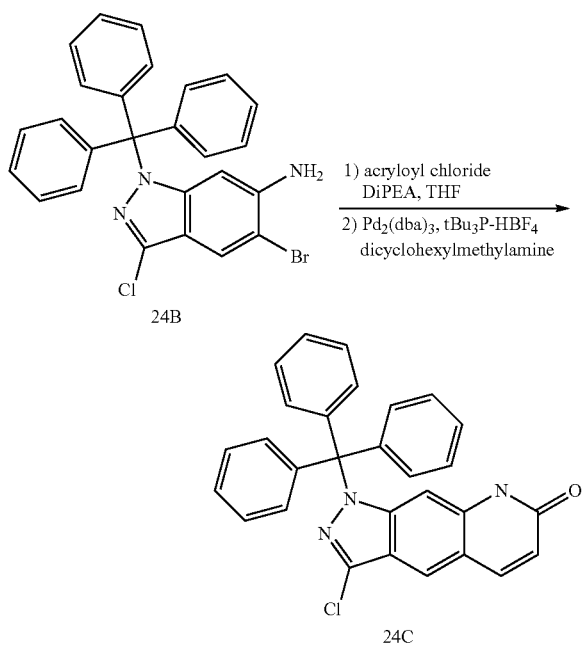

In a manner similar to that described in Example 4 (Steps 3-4), 5-bromo-3-chloro-1-trityl-1H-indazol-6-amine was treated sequentially with acryloyl chloride (Hunig's base, THF) and then Pd$_2$(dba)$_3$, (tBu$_3$P—HBF$_4$, dicyclohexylmethylamine) to give 3-chloro-1-trityl-1H-pyrazolo[4,3-g]quinolin-7(8H)-one.

Steps 6-7

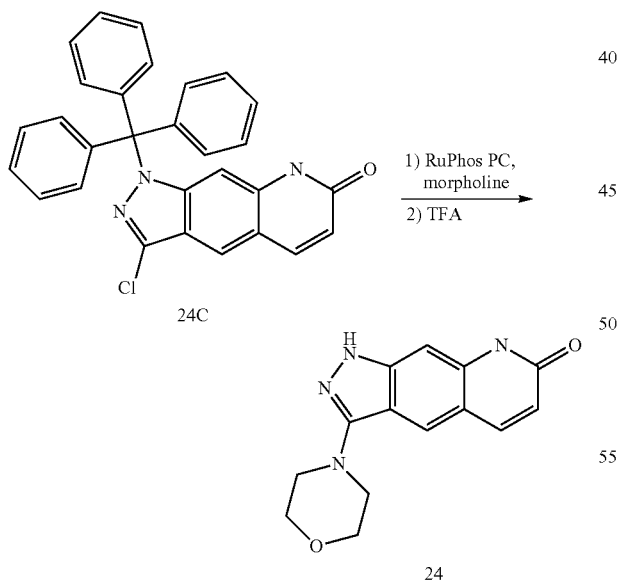

In a 1 dram vial was added morpholine (1.4 mg, 0.016 mmoles, 1.5 eq.), and sodium t-butoxide (3.12 mg, 0.032 mmol, 3 eq). In a second 1 dram vial was added 3-chloro-1-trityl-1,8-dihydro-7H-pyrazolo[4,3-g]quinolin-7-one (5 mg, 10.82 μmol) with Ruphos pre-catalyst (chloro-(2-dicyclohexylphosphino-2',6'-diisopropoxy-1,1'-biphenyl)[2-(2-aminoethyl)phenyl]-palladium(II)), 0.158 mg, 0.216 μmol) dissolved in 0.5 mL of degassed THF (from nitrogen gas over 45 minutes). This solution was dispensed (0.5 mL each) into the first 1 dram vial. The vial was purged with nitrogen gas, sealed with a stir bar, and were heated at 65° C. for 16 hours. The solvent was removed and the product were purified by semi-preparative RP-HPLC to generate the pure title compound 3-morpholino-1-trityl-1H-pyrazolo[4,3-g]quinolin-7(8H)-one (LCMS: [M+H]$^+$ m/z 513)

In a 1 dram vial containing the aforementioned product 3-morpholino-1-trityl-1H-pyrazolo[4,3-g]quinolin-7(8H)-one, 0.5 mL of DCM, 0.5 mL TFA and 10 uL of triethylsilane were added and the vial was stirred at room temperature for 2 hours. 0.5 mL of water was added after this time and the solvents were removed in vacuo. Analytical LC/MS analysis indicated that the deprotection of the trityl group was complete. The solvents were removed in vacuo and lyophilized from water/ACN to obtain 3-morpholino-1H-pyrazolo[4,3-g]quinolin-7(8H)-one. LCMS: [M+H]$^+$ m/z 271.

Example 26

(R)-3-(1-methyl-1H-benzo[d][1,2,3]triazol-6-yl)-6-(1-phenylethyl)-5,6-dihydro-1H-pyrazolo[4,3-g]quinazolin-7(8H)-one

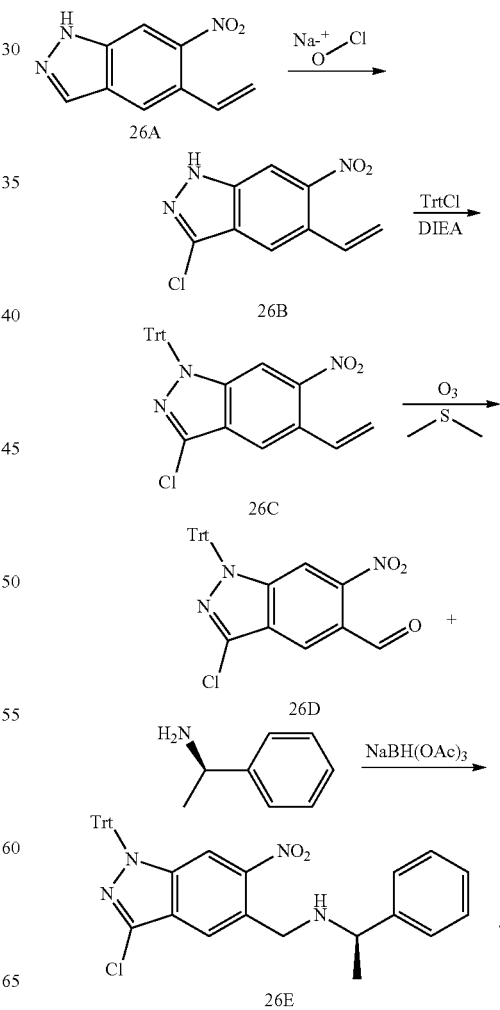

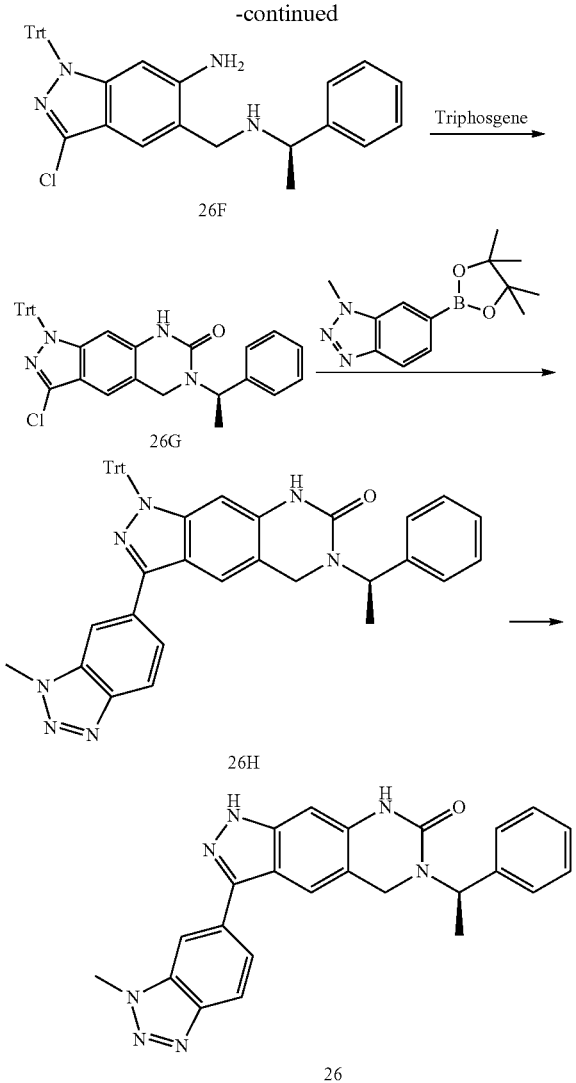

Step 1

Sodium hypochlorite (21.54 mL, 13.96 mmol) was added to a stirred, room temperature mixture of 6-nitro-5-vinyl-1H-indazole 26A (2.2 g, 11.63 mmol, prepared from 5-bromo-6-nitro-1H-indazole and tributyl(vinyl)stannane as described in Example 10, Step 1) in dichloromethane (100 mL) and the mixture was stirred at room temperature overnight. The mixture was diluted with dichloromethane (6 mL), washed with water (2 mL), dried (MgSO$_4$), filtered and the solvent was evaporated under reduced pressure. The residue was purified by column chromatography on silica gel (24 g), eluting with EtOAc/isohexane=10% to give 3-chloro-6-nitro-5-vinyl-1H-indazole (26B). MS ESI calc'd. for $C_9H_6ClN_3O_2$ [M+H]$^+$ 224, found 224.

Step 2

Triphenylmethyl chloride (2.54 g, 9.12 mmol) was added to a stirred, room temperature mixture of 3-chloro-6-nitro-5-vinyl-1H-indazole (1.7 g, 7.60 mmol) and Hunig's Base (2.66 mL, 15.20 mmol) in dichloromethane (40 mL), and the mixture was stirred at room temperature for overnight. The mixture was concentrated, the residue was purified by column chromatography on silica gel (24 g), eluting with EtOAc/isohexane=10% to give 3-chloro-6-nitro-1-trityl-5-vinyl-1H-indazole (26C).

Step 3

Ozone (0.340 g, 7.08 mmol) was bubbled into a stirred, −78° C. mixture of 3-chloro-6-nitro-1-trityl-5-vinyl-1H-indazole (3.3 g, 7.08 mmol) in dichloromethane (50 mL) and MeOH (25 mL) till the mixture turned greenish blue, indicating the excess of ozone. Nitrogen was then blown into the mixture to remove the excess of ozone. When the color changed from greenish blue to yellow, dimethyl sulfide (5.18 mL, 70.8 mmol) was added, and the mixture was stirred at room temperature for 1 h. The mixture was concentrated, the residue was diluted with ethyl acetate (60 mL), washed with aqueous ammonium chloride (saturated, 1×30 mL), and water (3×30 mL), dried (MgSO$_4$), filtered and the solvent was evaporated under reduced pressure to give 3-chloro-6-nitro-1-trityl-1H-indazole-5-carbaldehyde (26D).

Step 4

Sodium triacetoxyborohydride (1.699 g, 8.01 mmol) was added to a stirred, room temperature mixture of (R)-(+)-1-phenyl ethylamine (0.818 mL, 6.41 mmol) and 3-chloro-6-nitro-1-trityl-1H-indazole-5-carbaldehyde (1.5 g, 3.21 mmol) in dichloroethane (30 mL), and the mixture was stirred at room temperature. Reaction was monitored via LCMS, 1 h, 6 h, and overnight. The mixture was directly loaded onto the column (120 g, silica gel), the column was purged with air for 5 min and eluted with EtOAc/isohexane=10% to give (R)—N-((3-chloro-6-nitro-1-trityl-1H-indazol-5-yl)methyl)-1-phenylethanamine (26E). MS ESI calc'd. for $C_{35}H_{29}ClN_4O_2$ [M+H]$^+$ 573, found 573.

Step 5

Zinc (0.570 g, 8.72 mmol) was added to a stirred, room temperature mixture of (R)—N-((3-chloro-6-nitro-1-trityl-1H-indazol-5-yl)methyl)-1-phenylethanamine (0.5 g, 0.872 mmol) in acetic acid (88 mL,) and the mixture was stirred at 60° C. for 1 h. LCMS check, completed, starting material disappeared. The mixture was filtered through Celite, washed with MeOH, the filtrate was concentrated. The residue was diluted with dichloromethane (5 mL), water (1 mL) was added, the aqeuous layer was basified with aqueous sodium hydrogen carbonate saturated to pH 9, extracted with dichloromethane (2×3 mL), the combined organic was dried MgSO$_4$, filtered and concentrated, the residue was purified by column chromatography on silica gel (40 g), eluted with EtOAc/isohexane=1:2 to give (R)-3-chloro-5-(((1-phenylethyl)amino)methyl)-1-trityl-1H-indazol-6-amine (26F). MS ESI calc'd. for $C_{35}H_{31}ClN_4$ [M+H]$^+$ 543, found 543.

Step 6

Triphosgene (43.7 mg, 0.147 mmol) was added to a stirred, room temperature mixture of (R)-3-chloro-5-(((1-phenylethyl)amino)methyl)-1-trityl-1H-indazol-6-amine (200 mg, 0.368 mmol) in dichloromethane (3 mL) and the mixture was stirred at room temperature for overnight. The mixture was diluted with dichloromethane (5 mL), washed with aqueous sodium hydrogen carbonate (saturated, 1×6 mL), dried (MgSO$_4$), filtered and the solvent was evaporated under reduced pressure. The residue was purified by column chromatography on silica gel (40 g), eluting with EtOAc/isohexane=1:3 to give (R)-3-chloro-6-(1-phenylethyl)-1-trityl-5,6-dihydro-1H-pyrazolo[4,3-g]quinazolin-7(8H)-one (26G). MS ESI calc'd. for $C_{36}H_{29}ClN_4O$ [M+H]$^+$ 569, found 569.

Step 7

1-methyl-6-(4,4,5,5-tetramethyl-1,3,2-dioxaborolan-2-yl)-1H-benzo[d][1,2,3]triazole (27.3 mg, 0.105 mmol), (R)-3-chloro-6-(1-phenylethyl)-1-trityl-5,6-dihydro-1H-pyrazolo[4,3-g]quinazolin-7(8H)-one (50 mg, 0.088 mmol), Xphos-Pd-Precatalyt-G2 (17 mg, 0.022 mmol) and potassium phosphate tribasic (55.9 mg, 0.264 mmol) were mixed in a pressure release vial, degassed and backfilled with nitrogen (3×), dioxane (3 mL) and water (1 mL) were added, the resultant mixture was degassed and backfilled with nitrogen (3×) again, and heated up to 80° C. for 3 h. LCMS check, completed, starting material disappeared. The mixture was cooled, the mixture was diluted with dichloromethane (10 mL) and water (3 mL), filtered through celite, organic layer was separated and washed with brine (5 mL), dried (MgSO$_4$), filtered and the solvent was evaporated under reduced pressure. The residue was purified by column chromatography on silica gel (24 g), eluting with EtOAc/isohexane=30%→100% to give (R)-3-(1-methyl-1H-benzo[d][1,2,3]triazol-6-yl)-6-(1-phenylethyl)-1-trityl-5,6-dihydro-1H-pyrazolo[4,3-g]quinazolin-7(8H)-one (26H). MS ESI calc'd. for C$_{43}$H$_{35}$N$_7$O [M+H]$^+$ 666, found 666.

Step 8

Triethylsilane (50 μL, 0.313 mmol) was added to a stirred, room temperature mixture of (R)-3-(1-methyl-1H-benzo[d][1,2,3]triazol-6-yl)-6-(1-phenylethyl)-1-trityl-5,6-dihydro-1H-pyrazolo[4,3-g]quinazolin-7(8H)-one (50 mg, 0.075 mmol) in TFA (2 mL, 26.0 mmol) and the mixture was stirred at room temperature for 2 h. The mixture was concentrated, and the residue was purified by preparative HPLC Reverse phase (C-18), eluting with Acetonitrile/water+0.1% TFA, to give (R)-3-(1-methyl-1H-benzo[d][1,2,3]triazol-6-yl)-6-(1-phenylethyl)-5,6-dihydro-1H-pyrazolo[4,3-g]quinazolin-7(8H)-one 2,2,2-trifluoroacetate (26). MS ESI calc'd. for C$_{24}$H$_{21}$N$_7$O [M+H]$^+$ 424, found 424.

Example 29

(R)-3-(ethylamino)-6-(1-phenylethyl)-5,6-dihydro-1H-pyrazolo[4,3-g]quinazolin-7(8H)-one

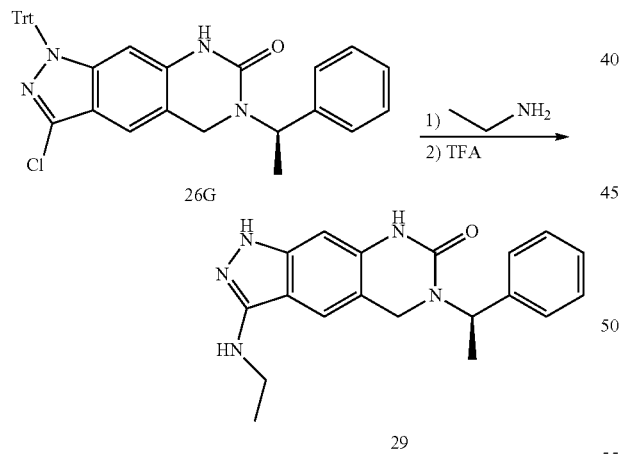

Steps 1-2

In the reaction vessel ethyl amine (2M in THF) (0.079 mL, 0.158 mmol) and (R)-3-chloro-6-(1-phenylethyl)-1-trityl-5,6-dihydro-1H-pyrazolo[4,3-g]quinazolin-7(8H)-one 7 (60 mg, 0.105 mmol) were combined, followed by Brettphos palladacycle (16.84 mg, 0.021 mmol). This mixture was then evacuated and backfilled with N$_2$ (3 times). Then dry, degassed dioxane (1 mL) and potassium tert-butoxide (1M in THF) (0.316 mL, 0.316 mmol) was added to the mixture. This mixture was then evacuated and backfilled with N$_2$ (3 times), then heated at 80° C. for 4 h. LCMS check, completed, starting material disappeared. The reaction mixture was loaded directly onto a 40 g silica column, airpurged for 10 min, then eluted with EtOAc/isohexane=30%→80% to give (R)-3-(ethylamino)-6-(1-phenylethyl)-1-trityl-5,6-dihydro-1H-pyrazolo[4,3-g]quinazolin-7(8H)-one. MS ESI calc'd. for C$_{38}$H$_{35}$N$_5$O [M+H]$^+$ 578, found 578.

In a manner similar to that previously described (e.g. Example 26, Step 8), (R)-3-(ethylamino)-6-(1-phenylethyl)-1-trityl-5,6-dihydro-1H-pyrazolo[4,3-g]quinazolin-7(8H)-one was deprotected with TFA and triethylsilane to provide (R)-3-(ethylamino)-6-(1-phenylethyl)-5,6-dihydro-1H-pyrazolo[4,3-g]quinazolin-7(8H)-one. MS ESI calc'd. for C$_{19}$H$_{21}$N$_5$O [M+H]$^+$ 336, found 336.

Examples 30 and 31

6-((R)-1-phenylethyl)-3-(((S)-1,1,1-trifluoropropan-2-yl)amino)-5,6-dihydro-1H-pyrazolo[4,3-g]quinazolin-7(8H)-one and (R)-6-(1-phenylethyl)-5,6-dihydro-1H-pyrazolo[4,3-g]-quinazolin-7(8H)-one

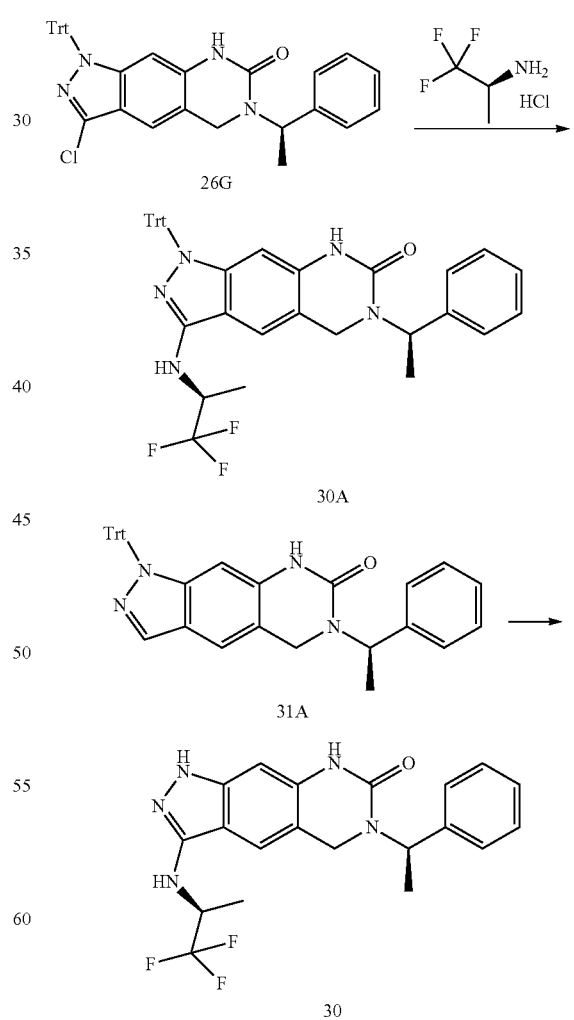

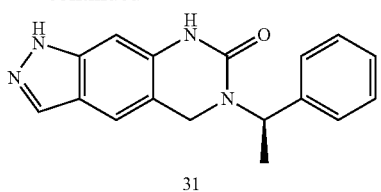

31

Steps 1-2

In the reaction vessel (S)-1,1,1-trifluoroisopropylamine hydrochloride (23.65 mg, 0.158 mmol) and (R)-3-chloro-6-(1-phenylethyl)-1-trityl-5,6-dihydro-1H-pyrazolo[4,3-g]quinazolin-7(8H)-one (26G, 60 mg, 0.105 mmol) were combined, followed by Brettphos palladacycle (16.84 mg, 0.021 mmol). This mixture was then evacuated and backfilled with $N_2$ (3 times). Then dry, degassed dioxane (1 mL) and potassium tert-butoxide (1M in THF) (0.316 mL, 0.316 mmol) was added to the mixture. This mixture was then evacuated and backfilled with $N_2$ (3 times), then heated at 80° C. for 12 h. LCMS check, completed, starting material disappeared. The reaction mixture was loaded directly onto a 40 g silica gel column, airpurged for 10 min, then eluted with EtOAc/isohexane=30%→60% to give mixture of 6-((R)-1-phenylethyl)-3-(((S)-1,1,1-trifluoropropan-2-yl)amino)-1-trityl-5,6-dihydro-1H-pyrazolo[4,3-g]quinazolin-7(8H)-one 30A and (R)-6-(1-phenylethyl)-1-trityl-5,6-dihydro-1H-pyrazolo[4,3-g]quinazolin-7(8H)-one 31A.

Triethylsilane (50 µL, 0.313 mmol) was added to a stirred, room temperature mixture of 30A and 31A (65 mg, 0.101 mmol) in TFA (2 mL, 26.0 mmol) and the mixture was stirred at room temperature for 2 h. LCMS check, completed, starting material disappeared. The mixture was concentrated to dryness, and the residue was purified by preparative HPLC Reverse phase (C-18), eluting with Acetonitrile/water+0.1% TFA, to give 6-((R)-1-phenylethyl)-3-(((S)-1,1,1-trifluoropropan-2-yl)amino)-5,6-dihydro-1H-pyrazolo[4,3-g]quinazolin-7(8H)-one 2,2,2-trifluoroacetate (30), MS ESI calc'd. $C_{20}H_{20}F_3N_5O$ [M+H]$^+$ 404, found 404; and (R)-6-(1-phenylethyl)-5,6-dihydro-1H-pyrazolo[4,3-g]quinazolin-7(8H)-one 2,2,2-trifluoroacetate (31), MS ESI calc'd. for $C_{17}H_{16}N_4O$ [M+Na]$^+$ 315, found 315 [M+Na].

Example 32

(R)-3-amino-6-(1-phenylethyl)-5,6-dihydro-1H-pyrazolo[4,3-g]quinazolin-7(8H)-one

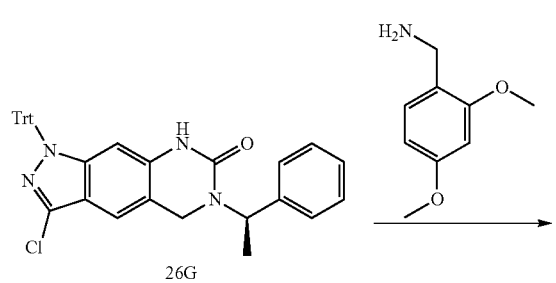

26G

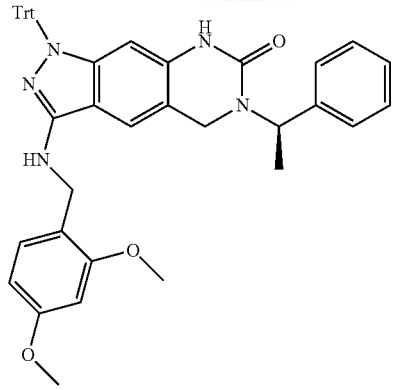

32A

32

Step 1

In the reaction vessel 2,4-dimethoxybenzylamine (66.1 mg, 0.395 mmol) and (R)-3-chloro-6-(1-phenylethyl)-1-trityl-5,6-dihydro-1H-pyrazolo[4,3-g]quinazolin-7(8H)-one (26G, 150 mg, 0.264 mmol) were combined, followed by Brettphos palladacycle (42.1 mg, 0.053 mmol). This mixture was then evacuated and backfilled with $N_2$ (3 times). Then dry, degassed dioxane (2 mL) and potassium tert-butoxide (1M in THF) (0.791 mL, 0.791 mmol) was added to the mixture. This mixture was then evacuated and backfilled with $N_2$ (3 times), then heated at 80° C. for overnight. LCMS check, completed, starting material disappeared. The reaction mixture was loaded directly onto a 40 g silica column, airpurged for 10 min, and then eluted with EtOAc/isohexane=30-80% to give (R)-3-((2,4-dimethoxybenzyl)amino)-6-(1-phenylethyl)-1-trityl-5,6-dihydro-1H-pyrazolo[4,3-g]quinazolin-7(8H)-one (32A). MS ESI calc'd. $C_{45}H_{41}N_5O_3$ [M+H]$^+$ 700, found 700.

Step 2

Triethylsilane (25 µL, 0.157 mmol) was added to a stirred, room temperature mixture of (R)-3-((2,4-dimethoxybenzyl)amino)-6-(1-phenylethyl)-1-trityl-5,6-dihydro-1H-pyrazolo[4,3-g]quinazolin-7(8H)-one (32A, 45 mg, 0.064 mmol) in TFA (1 mL, 12.98 mmol) and the mixture was stirred at room temperature for 2 h. The mixture was concentrated, and the residue was purified by preparative HPLC Reverse phase (C-18), eluting with Acetonitrile/water+0.1% TFA, to give (R)-3-amino-6-(1-phenylethyl)-5,6-dihydro-1H-pyrazolo[4,3-g]quinazolin-7(8H)-one 2,2,2-trifluoroacetate. MS ESI calc'd. $C_{17}H_{17}N_5O$ [M+H]$^+$ 308, found 308.00

Example 33

(R)-methyl (7-oxo-6-(1-phenylethyl)-5,6,7,8-tetrahydro-1H-pyrazolo[4,3-g]quinazolin-3-yl)carbamate

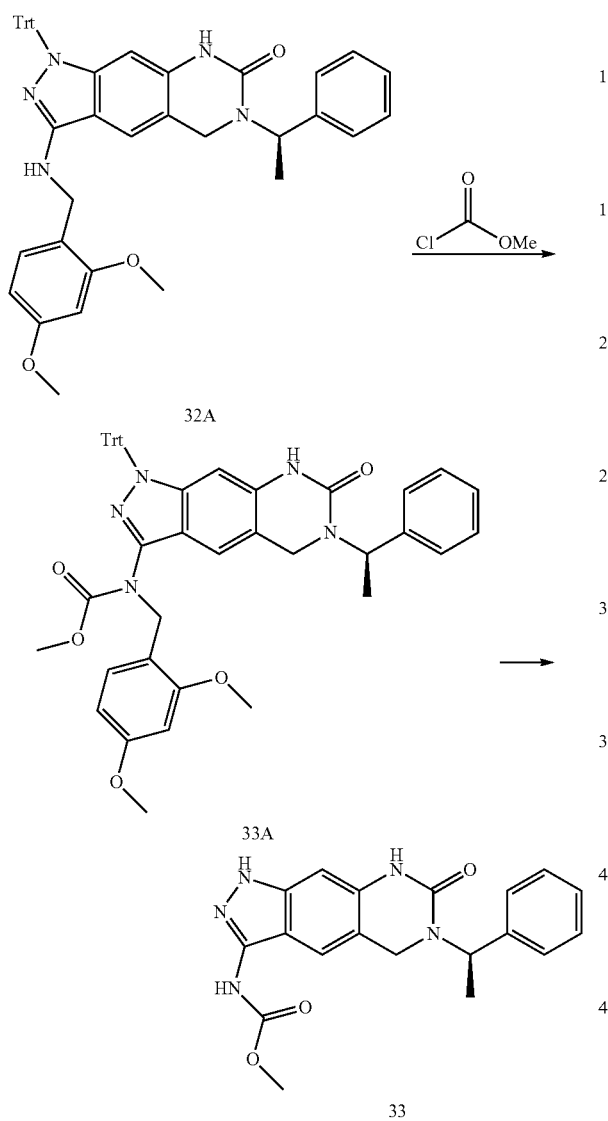

Steps 1-2

Methyl chloroformate (6.64 μL, 0.086 mmol) was added to a stirred, room temperature mixture of (R)-3-((2,4-dimethoxybenzyl)amino)-6-(1-phenylethyl)-1-trityl-5,6-dihydro-1H-pyrazolo[4,3-g]quinazolin-7(8H)-one (32A, 40 mg, 0.057 mmol) and pyridine (100 μL, 1.236 mmol) in dichloromethane (1 mL) and the mixture was stirred at room temperature for overnight. The residue was loaded directly onto a 24 g silica gel column, airpurged for 10 min., and then eluted with EtOAc/isohexane=2:1, to give (R)-methyl 2,4-dimethoxybenzyl(7-oxo-6-(1-phenylethyl)-1-trityl-5,6,7,8-tetrahydro-1H-pyrazolo[4,3-g]quinazolin-3-yl)carbamate. MS ESI calc'd. $C_{47}H_{43}N_5O_5$ [M+H]$^+$ 758, found 758.

In a manner similar to that previously described (e.g. Example 32, Step 2), (R)-methyl 2,4-dimethoxybenzyl(7-oxo-6-(1-phenylethyl)-1-trityl-5,6,7,8-tetrahydro-1H-pyrazolo[4,3-g]quinazolin-3-yl)carbamate was deprotected with TFA and triethylsilane to provide (R)-methyl (7-oxo-6-(1-phenylethyl)-5,6,7,8-tetrahydro-1H-pyrazolo[4,3-g]quinazolin-3-yl)carbamate. MS ESI calc'd. for $C_{19}H_{21}N_5O$ [M+H]$^+$ 366, found 366.

Example 35

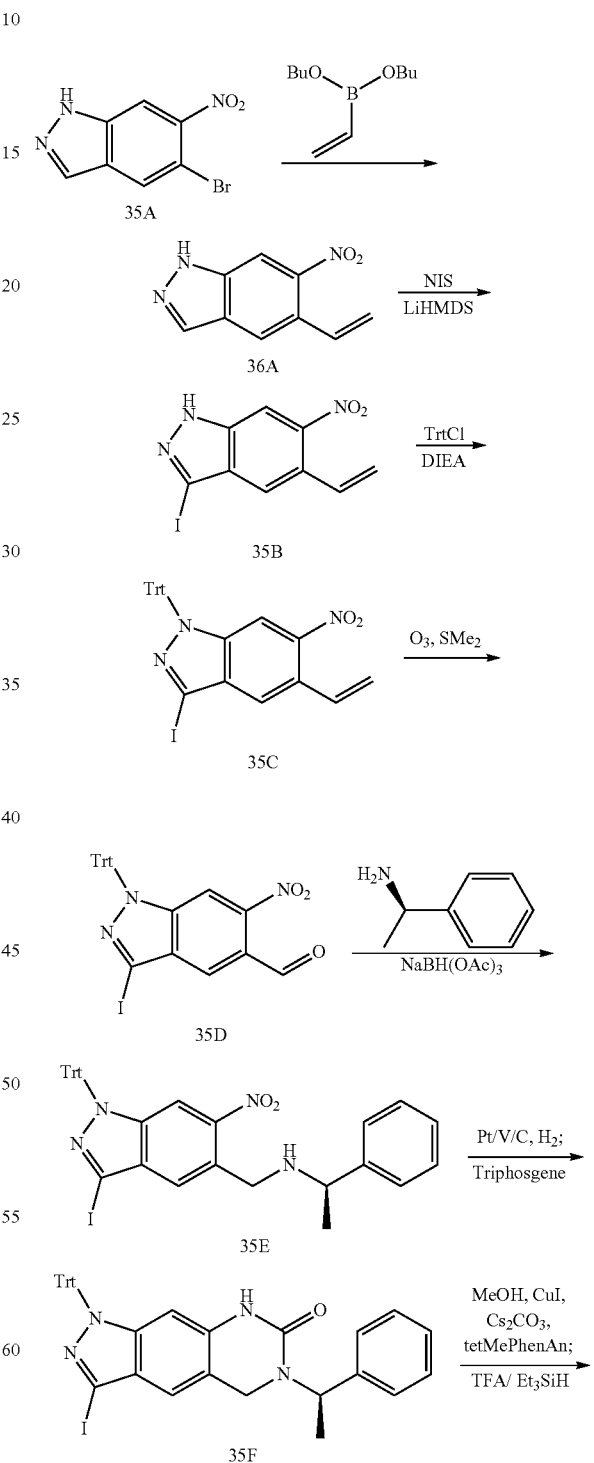

-continued

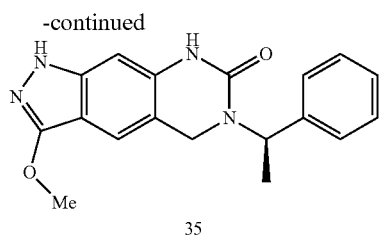

35

Step 1

In a flask fitted with a reflux condenser under an atmosphere of nitrogen gas, 5-bromo-6-nitro-1H-indazole (6.01 g, 24.83 mmol) was dissolved in a solution of dioxane (100 ml)/water (50 ml) and vinylboronic acid dibutyl ester (8.21 ml, 37.2 mmol), 1,1'-bis(diphenylphosphino)ferrocene-palladium(ii)dichloride dichloromethane complex (2.332 g, 2.86 mmol) followed by potassium phosphate (16.87 g, 79 mmol) were added. The resulting mixture was heated to 80° C. and stirred overnight. The mixture was diluted with dichloromethane (400 mL) and basified with aqueous sodium hydrogen carbonate (500 mL) to pH 8. The biphasic solution was separated and the aqueous layer was extracted with dichloromethane (2×500 mL). The combined organic phase was dried over sodium sulfate, filtered and concentrated to dryness under reduced pressure. Column chromatographic purification (220 g silica column, 5-75% ethyl acetate/hexanes) provided 6-nitro-5-vinyl-1H-indazole (26A).

Step 2

In a flask, under an atmosphere of nitrogen gas, 6-nitro-5-vinyl-1H-indazole (1.65 g, 8.72 mmol) was dissolved in THF (50 ml). The reaction mixture was treated with 1.0 M solution of sodium bis(trimethylsilyl)amide in tetrahydrofuran (21.81 ml) and stirred at room temperature for 30 minutes before the addition of N-iodosuccinimide (3.53 g, 15.70 mmol). The resulting reaction was stirred at room temperature overnight. The mixture was diluted with dichloromethane (150 mL) and basified with aqueous sodium hydrogen carbonate (150 mL) to pH 8. The biphasic solution was separated and the aqueous layer was extracted with dichloromethane (2×150 mL). The combined organic phase was dried over sodium sulfate, filtered and concentrated to provide 3-iodo-6-nitro-5-vinyl-1H-indazole (35B).

Steps 3-7

In a manner similar to that described in Example 26 (Step 2-4), 3-iodo-6-nitro-5-vinyl-1H-indazole was sequentially treated with trityl chloride (Hunig's base, DCM), ozone (MeOH-DCM) and (R)-(+)-1-phenyl ethylamine (sodium triacetoxyborohydride, dichloroethane) to provide 3-iodo-6-nitro-1-trityl-5-vinyl-1H-indazole 35E.

In a manner similar to that described in Example 24 (Step 3) and Example 26 (Step 6), respectively, 3-iodo-6-nitro-1-trityl-5-vinyl-1H-indazole was sequentially hydrogenated (1 atm H$_2$, 3% Pt/0.6% V on carbon, MeOH-DCM) and then treated with triphosgene to provide (R)-3-iodo-6-(1-phenylethyl)-1-trityl-5,6-dihydro-1H-pyrazolo[4,3-g]quinazolin-7(8H)-one 35F Steps 8-9

(R)-3 odo-6-(1-phenylethyl)-1-trityl-5,6-dihydro-1H-pyrazolo[4,3-g]quinazolin-7(8H)-one (14 mg, 0.021 mmol), 3,4,7,8-tetramethyl-1,10-phenanthroline (35F, 5.01 mg, 0.021 mmol), cesium carbonate (20.72 mg, 0.064 mmol), copper(I) iodide (2.018 mg, 10.60 µmol) and methanol (500 µl, 12.48 mmol) were combined in a microwave vial. This mixture was then microwaved for 20 minutes at 140° C. The mixture was diluted with water and then extracted with DCM. The combined organic layers were filtered through celite, concentrated, and purified by column chromatography (12 g, 0-50% EtOAc/hexanes) to give (R)-3-methoxy-6-(1-phenylethyl)-1-trityl-5,6-dihydro-1H-pyrazolo[4,3-g]quinazolin-7(8H)-one.

In a manner similar to that described earlier (e.g. Example 26, Step 8) (R)-3-methoxy-6-(1-phenylethyl)-1-trityl-5,6-dihydro-1H-pyrazolo[4,3-g]quinazolin-7(8H)-one was treated with TFA and Et$_3$SiH to provide (R)-3-methoxy-6-(1-phenylethyl)-5,6-dihydro-1H-pyrazolo[4,3-g]quinazolin-7(8H)-one (35). LCMS: [M+H]$^+$ m/z 323.

Example 38

6-((R)-1-phenylethyl)-3-((tetrahydrofuran-3-yl)oxy)-5,6-dihydro-1H-pyrazolo[4,3-g]quinazolin-7(8H)-one

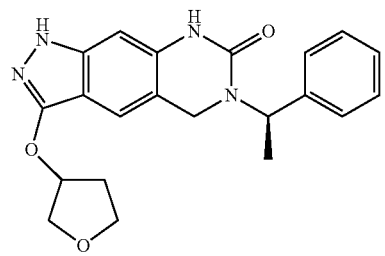 [SMILES: C[C@H](c1ccccc1)N1Cc2cc3c(OC4CCOC4)n[nH]c3cc2NC1=O]

In a manner similar to that described Example 35, (R)-3-iodo-6-(1-phenylethyl)-1-trityl-5,6-dihydro-1H-pyrazolo[4,3-g]quinazolin-7(8H)-one (35F) was reacted with tetrahydrofuran-3-ol (Cs$_2$CO$_3$, CuI, 3,4,7,8-tetramethyl-1,10-phenanthroline) with toluene (0.076M) added as a solvent (microwaved 20 min at 150° C.). The resulting product was chromatographed and then treated with TFA and Et$_3$SiH to provide 6-((R)-1-phenylethyl)-3-((tetrahydrofuran-3-yl)oxy)-5,6-dihydro-1H-pyrazolo[4,3-g]quinazolin-7(8H)-one (38). LCMS: [M+H]$^+$ m/z 379.

Example 40

(R)-3-cyclopropyl-6-(1-phenylethyl)-5,6-dihydro-1H-pyrazolo[4,3-g]quinazolin-7(8H)-one

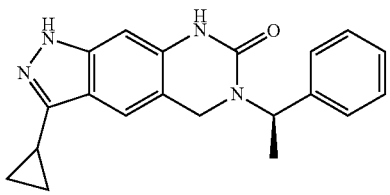 [SMILES: C[C@H](c1ccccc1)N1Cc2cc3c(C4CC4)n[nH]c3cc2NC1=O]

To a vial were added (R)-3-iodo-6-(1-phenylethyl)-1-trityl-5,6-dihydro-1H-pyrazolo[4,3-g]quinazolin-7(8H)-one (35F, 0.02 g, 0.030 mmol), 1,1'-bis(diphenylphosphino)ferrocene-palladium(ii)dichloride dichloromethane complex (4.95 mg, 6.06 µmol), 2-cyclopropyl-4,4,5,5-tetramethyl-1,3,2-dioxaborolane (10.18 mg, 0.061 mmol), potassium carbonate (10.46 mg, 0.076 mmol), dioxane (1 ml) and water (0.5 ml). The mixture was Vac/N2 purged 6 times and heated at 70° C. for 4 h. The mixture was diluted with DCM (5 mL). The organic phase was separated and filtered to afford (R)-3-cyclopropyl-6-(1-phenylethyl)-1-trityl-5,6-dihydro-1H-pyrazolo[4,3-g]quinazolin-7(8H)-one.

The solid was treated with trifluoroacetic acid (500 μl, 6.49 mmol) and triethylsilane (10 μl, 0.063 mmol) and stirred overnight at room temperature. The reaction was then concentrated and purified by preparative HPLC (Reverse phase C-18, Waters SunFire PrepODB, 150×19 mm, 5 u, eluting with 10-95% Acetonitrile/Water+0.1% TFA, 20 mL/min. over 15 min.) to give (R)-3-cyclopropyl-6-(1-phenylethyl)-5,6-dihydro-1H-pyrazolo[4,3-g]quinazolin-7(8H)-one-TFA salt (40). (TFA salt). LCMS: [M+H]$^+$ m/z 333.

Example 42

(R)-3-morpholino-6-(1-phenylethyl)-5,6-dihydro-1H-pyrazolo[4,3-g]quinazolin-7(8H)-one

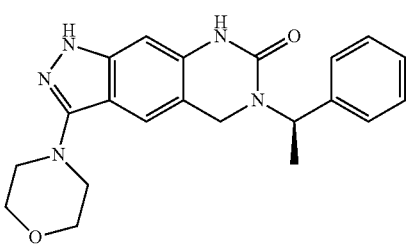 [SMILES: C[C@H](c1ccccc1)N1Cc2cc3c(N4CCOCC4)n[nH]c3cc2NC1=O]

A flask was charged with (R)-3-iodo-6-(1-phenylethyl)-1-trityl-5,6-dihydro-1H-pyrazolo[4,3-g]quinazolin-7(8H)-one (35F, 0.02 g, 0.030 mmol), copper(I) iodide (1 mg, 5.25 μmol), L-proline (2 mg, 0.017 mmol) and potassium carbonate (4.18 mg, 0.030 mmol). DMSO (1514 μl) and morpholine (5.28 μl, 0.061 mmol) were added and the reaction was degassed (vacuum/nitrogen). The mixture was heated at 70° C. for 4 h, at which time additional CuI (2 mg), L-proline (2 mg, 0.017 mmol), and morpholine (12 uL) were added. The mixture was then heated at 90° C. overnight, cooled and then diluted with DCM and water. The layers were separated and the aqueous layer was extracted with DCM. The combined organic layers were filtered through celite and concentrated. Purification by column chromatography on silica gel (12 g, eluting with 0-40% EtOAc/hexanes) gave (R)-3-morpholino-6-(1-phenylethyl)-1-trityl-5,6-dihydro-1H-pyrazolo[4,3-g]quinazolin-7(8H)-one. LCMS: [M+H]$^+$ m/z 620.

The residue was treated with trifluoroacetic acid (500 μl, 6.49 mmol) and triethylsilane (10 μl, 0.063 mmol) and then stirred overnight at room temperature. The mixture was concentrated. The residue was purified by column chromatography on silica gel (4 g, eluting with 100% EtOAc) to give (R)-3-morpholino-6-(1-phenylethyl)-5,6-dihydro-1H-pyrazolo[4,3-g]quinazolin-7(8H)-one (42). LCMS: [M+H]$^+$ m/z 378.

Example 44

(R)-3-amino-6-(1-phenylethyl)-1H-pyrazolo[4,3-g]quinazoline-5,7(6H,8H)-dione

Step 1

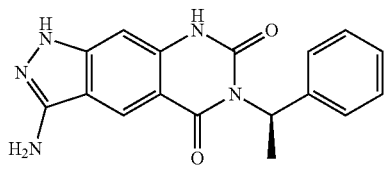 [SMILES: C[C@H](c1ccccc1)n1c(=O)[nH]c2cc3[nH]nc(N)c3cc2c1=O]

Brettphos palladacycle (41.4 mg, 0.052 mmol), K$_3$PO$_4$ (220 mg, 1.037 mmol), benzyl carbamate (104 mg, 0.691 mmol) and methyl 6-chloro-3-iodo-1-trityl-1H-indazole-5-carboxylate (200 mg, 0.346 mmol) were mixed toluene (3.5 ml) in a pressure release vial, degassed and backfilled with nitrogen (3×), and heated up to 78° C. for 16 h. The mixture was cooled and loaded onto a 40 g silica column, airpurged for 5 min, then eluted with EtOAc/isohexane=80→100% to give methyl 3-(((benzyloxy)carbonyl)amino)-6-chloro-1-trityl-1H-indazole-5-carboxylate (44A).

Steps 2-3

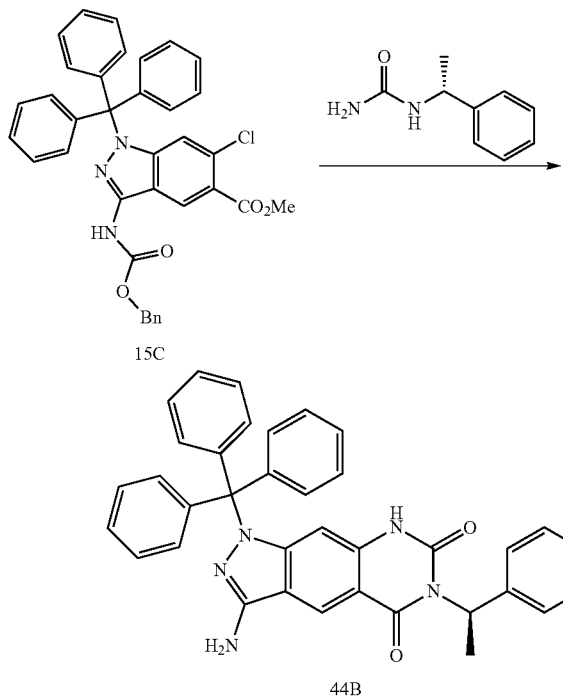

In a manner similar to that described in Example 15 (Step 3), (R)-1-(1-phenylethyl)urea (21.82 mg, 0.133 mmol), methyl 3-(((benzyloxy)carbonyl)amino)-6-chloro-1-trityl-1H-indazole-5-carboxylate (40 mg, 0.066 mmol), XantPhos Biaryl Precatalyst (11.81 mg, 0.013 mmol), cesium carbonate (64.9 mg, 0.199 mmol) in dioxane (1 mL) were mixed in a pressure release vial, degassed and backfilled with nitrogen (3×), and the mixture was heated up to 100° C. for 24 h. The mixture was cooled and loaded onto a 40 g silica gel column, airpurged for 5 min, then eluted with EtOAc/isohexane=80→100% to give (R)-3-amino-6-(1-phenylethyl)-1-trityl-1H-pyrazolo[4,3-g]quinazoline-5,7(6H,8H)-dione (44B).

In a manner similar to that described in Example 15 (Step 4), (R)-3-amino-6-(1-phenylethyl)-1-trityl-1H-pyrazolo[4,3-g]quinazoline-5,7(6H,8H)-dione was treated with TFA and Et₃SiH to provide (R)-3-amino-6-(1-phenylethyl)-1H-pyrazolo[4,3-g]quinazoline-5,7(6H,8H)-dione 2,2,2-trifluoroacetate (44). LCMS: [M+H]⁺ m/z 322.

Example 45

(R)-3-(2-methylpyridin-4-yl)-6-(1-phenylethyl)-5,6-dihydro-1H-pyrazolo[3',4':5,6]-pyrido-[3,2-d]pyrimidin-7(8H)-one Step 1

Into a 500-mL round-bottom flask was placed a solution of 5-bromo-2-methylpyridin-3-amine (45A, 20 g, 107 mmol, 1.00 equiv) and N-bromosuccinimide (20 g, 112 mmol, 1.05 equiv) in acetonitrile (200 mL). After stirring for 2 h at 25° C., the reaction mixture was quenched by the addition of water (200 mL) and then extracted with dichloromethane (300 mL×3). The combined organic layers were washed with brine (200 mL×2), and dried over anhydrous sodium sulfate. Upon filtration and concentration under vacuum, the crude product was purified by a flash chromatography on a silica gel column eluting with ethyl acetate/petroleum ether (1:3) to afford 5,6-dibromo-2-methylpyridin-3-amine (45B). ¹H-NMR (300 MHz, DMSO-d₆): δ ppm 7.25 (s, 1H), 5.53 (s, NH), 2.20 (s, 3H). MS m/z [M+H]⁺ (ESI): 266.

Step 2

Into a 1000-mL round-bottom flask was placed a mixture of 5,6-dibromo-2-methylpyridin-3-amine (28 g, 105.29 mmol, 1.00 equiv), acetic anhydride (42.9 g, 420.22 mmol, 4.00 equiv) and KOAc (12.4 g, 126.53 mmol, 1.20 equiv) in chloroform (500 mL). After stirring the reaction for 3 h at 25° C. and 2 h at reflux, isoamylnitrite (29.8 mL, 305.64 mmol, 1.00 equiv) and 18-crown-6 (2.5 g, 9.47 mmol, 0.10 equiv) were added at ambient temperature. The reaction mixture was heated for 8 h at reflux. After cooling the reaction to room temperature, methanol (100 ml) and a solution of potassium carbonate (29.0 g) in water (200 ml) were added. The resulting mixture was stirred for 3 h at 25° C. and extracted with ethyl acetate (500 mL×3). The combined organic layers were dried over anhydrous sodium sulfate. After filtration and concentration under vacuum, the residue was purified by a flash chromatography on silica gel column eluting with ethyl acetate/petroleum ether (1:3) to afford 5,6-dibromo-1H-pyrazolo[4,3-b]pyridine (45C). ¹H-NMR (300 MHz, DMSO-d₆): δ ppm 8.52 (s, 1H), 8.30 (s, 1H). MS m/z [M+H]⁺ (ESI): 277.

Step 3

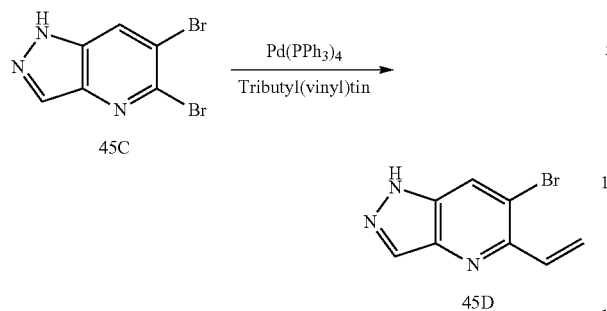

Into a 250-mL round-bottom flask purged and maintained with an inert atmosphere of nitrogen, was placed a solution of 5,6-dibromo-1H-pyrazolo[4,3-b]pyridine (10.0 g, 36.11 mmol, 1.00 equiv), tetrakis(triphenylphosphine)palladium (4.17 g, 3.61 mmol, 0.10 equiv), tributyl(ethenyl)stannane (12.68 g, 39.99 mmol, 1.10 equiv) in N,N-dimethylformamide (50 mL). After stirring overnight at 100° C. and cooling to room temperature, the reaction mixture was diluted with water (500 mL) and extracted with ethyl acetate (500 mL×3). The combined organic layers were washed with brine (500 mL×3) and dried over anhydrous sodium sulfate. After filtration and concentration under vacuum, the residue was purified by a flash chromatography on silica gel column eluting with ethyl acetate/petroleum ether (1:30-1:10) to afford 6-bromo-5-ethenyl-1H-pyrazolo[4,3-b]pyridine (45D). MS m/z [M+H]+ (ESI): 226.

Step 4

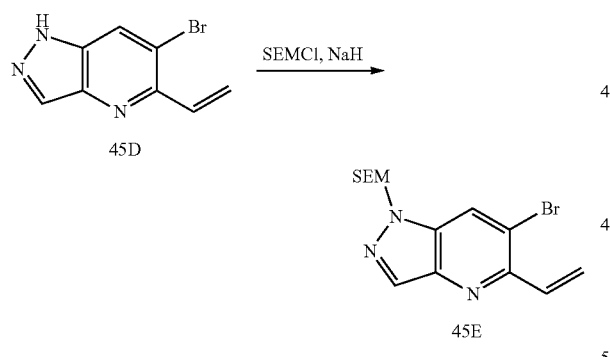

Into a solution of 6-bromo-5-ethenyl-1H-pyrazolo[4,3-b]pyridine (1.9 g, 8.48 mmol, 1.00 equiv) in N,N-dimethylformamide (20 mL) was added sodium hydride (370 mg, 60%, 15.42 mmol, 1.10 equiv) at 0° C. After stirring the reaction for 30 min at 0-10° C., SEM-Cl (2.1 g, 12.65 mmol, 1.50 equiv) was added. The resulting mixture was stirred overnight at room temperature, quenched with water (300 mL) and extracted with ethyl acetate (200 mL×3). The combined organic layers were washed with brine (200 mL×3) and dried over anhydrous sodium sulfate. After filtration and concentration under vacuum, the residue was purified by a flash chromatography on silica gel column eluting with ethyl acetate/petroleum ether (1:100-1:50) to afford 6-bromo-5-ethenyl-1-[[2-(trimethylsilyl)ethoxy]methyl]-1H-pyrazolo-[4,3-b]-pyridine (45E). MS m/z [M+H]+ (ESI): 356.

Step 5

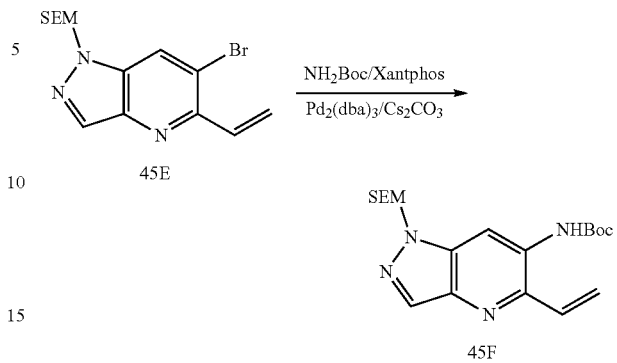

Into a 20-mL sealed tube purged and maintained with an inert atmosphere of nitrogen, was placed a mixture of 6-bromo-5-ethenyl-1-[[2-(trimethylsilyl)ethoxy]-methyl]-1H-pyrazolo[4,3-b]pyridine (1.90 g, 5.36 mmol, 1.00 equiv), tert-butyl carbamate (940 mg, 8.02 mmol, 1.50 equiv), Xantphos (310 mg, 0.54 mmol, 0.10 equiv), cesium carbonate (4.37 g, 13.41 mmol, 2.50 equiv), Pd2(dba)3 (280 mg, 0.27 mmol, 0.05 equiv) in dioxane (20 mL). After stirring for 4 h at 100° C. and cooling to room temperature, the reaction mixture was diluted with water (200 mL) and extracted with ethyl acetate (200 mL×3). The combined organic layers were washed with brine. (200 mL×3) and dried over anhydrous sodium sulfate. After filtration and concentrated under vacuum, the residue was purified by a flash chromatography on silica gel column eluting with ethyl acetate/petroleum ether (1:30-1:10) to afford tert-butyl N-(5-ethenyl-1-[[2-(trimethylsilyl)ethoxy]methyl]-1H-pyrazolo [4,3-b]pyridin-6-yl)carbamate (45F). MS m/z [M+H]+ (ESI): 391.

Step 6

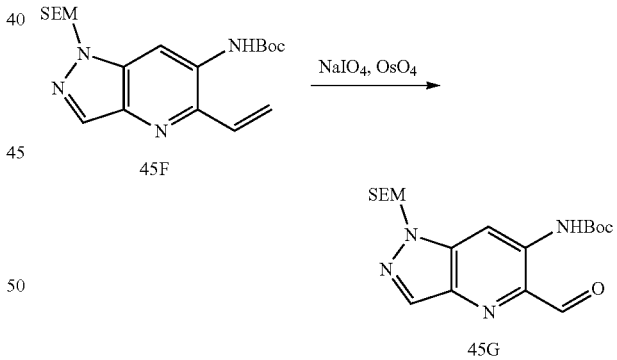

Into a 50-mL round-bottom flask, was placed tert-butyl N-(5-ethenyl-1-[[2-(trimethylsilyl)ethoxy]methyl]-1H-pyrazolo[4,3-b]pyridin-6-yl)carbamate (280 mg, 0.72 mmol, 1.00 equiv), sodium periodate (768 mg, 3.59 mmol, 5.00 equiv), osmium tetroxide (0.2 ml, 20 mg/mL in THF) in THF/H2O (20:1) (21 mL). After stirring for 2 h at ambient temperature, the reaction mixture was diluted with water (50 mL) and extracted with ethyl acetate (100 mL×3). The combined organic layers were washed with brine (100 mL×3) and dried over anhydrous sodium sulfate. Filtration and concentration under vacuum afforded tert-butyl N-(5-formyl-1-[[2-(trimethylsilyl)ethoxy]methyl]-1H-pyrazolo [4,3-b]pyridin-6-yl)carbamate (45G). 1H-NMR (400 MHz, CDCl₃): δ ppm 10.46 (s, 1H), 10.16 (s, 1H), 9.01 (s, 1H), 8.35 (s, 1H), 5.75 (s, 2H), 3.64-3.60 (m, 2H), 1.60 (s, 9H), 096-0.92 (m, 2H), 0.02 (s, 9H). MS m/z [M+H]⁺ (ESI): 393.
Step 7

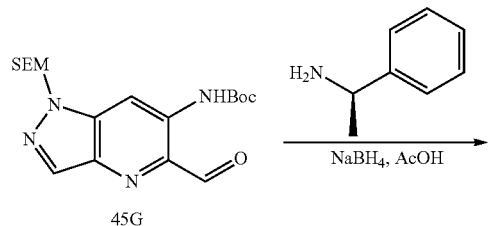

45G

Into a solution of tert-butyl N-(5-formyl-1-[[2-(trimethylsilyl)ethoxy]methyl]-1H-pyrazolo[4,3-b]pyridin-6-yl)carbamate (200 mg, 0.51 mmol, 1.00 equiv) and acetic acid (0.5 mL, 1.00 equiv) in 1,2-dichloroethane (5 mL) was added (1R)-1-phenylethan-1-amine (309 mg, 2.55 mmol, 5.00 equiv) at ambient temperature. After stirring for 1 h, methanol (10 mL) and sodium borohydride (58 mg, 1.53 mmol, 3.00 equiv) were added. The resulting mixture was stirred for 1 h at ambient temperature, quenched with sat. NaHCO₃ (100 mL) and extracted with ethyl acetate (100 mL×3). The combined organic layers were washed with brine (100 mL×3) and dried over anhydrous sodium sulfate. Upon filtration and concentration under vacuum, the residue was purified by a flash chromatography on silica gel column eluting with ethyl acetate/petroleum ether (1:30-1:10) to afford tert-butyl N-[5-([[(1R)-1-phenylethyl]amino]methyl)-1-[[2-(trimethylsilyl)ethoxy]methyl]-1H-pyrazolo[4,3-b]pyridin-6-yl]carbamate (45H) as a white solid. ¹H-NMR (400 MHz, CDCl₃): δ ppm 10.50 (s, NH), 8.59 (s, 1H), 8.09 (s, 1H), 7.46-7.29 (m, 5H), 5.72 (s, 2H), 4.18-4.12 (s, 2H), 4.08 (m, 1H),3.64-3.60 (m, 2H), 1.60 (s, 9H), 096-0.92 (m, 2H), 0.02 (s, 9H). MS m/z [M+H]⁺ (ESI): 498.
Step 8

Into a 50-mL round-bottom flask, was placed a solution of tert-butyl N-[5-([[(1R)-1-phenylethyl]amino]methyl)-1-[[2-(trimethylsilyl)ethoxy]methyl]-1H-pyrazolo[4,3-b]pyridin-6-yl]carbamate (500 mg, 1.00 mmol, 1.00 equiv) in hydrochloric acid (15 mL, 3 N, 10.00 equiv) and ethanol (15 mL). The solution was stirred for 25 min at 6° C. and diluted with water (100 mL). After the pH value of the solution was adjusted to 10-11 with potassium carbonate, the resulting solution was extracted with ethyl acetate (100 mL×3). The combined organic layers were dried over anhydrous sodium sulfate. Filtration and concentration under vacuum afforded 5-([[(1R)-1-phenylethyl]amino]methyl)-1-[[2-(trimethylsilyl)-ethoxy]methyl]-1H-pyrazolo[4,3-b]pyridin-6-amine (45I) as a yellow solid. MS m/z [M+H]⁺ (ESI): 398.
Step 9

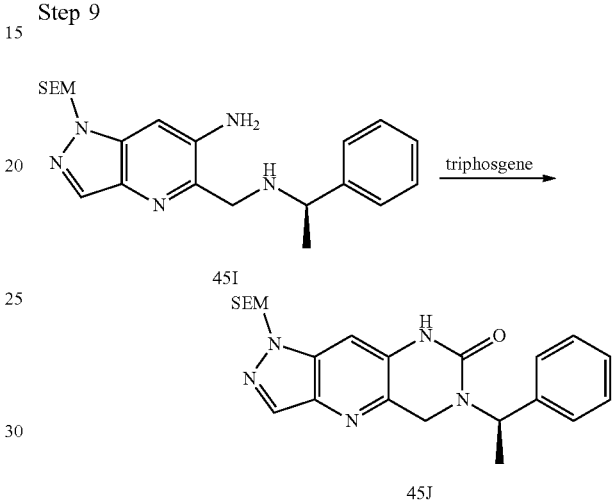

Into a solution of 5-([[(1R)-1-phenylethyl]amino]methyl)-1-[[2-(trimethylsilyl)-ethoxy]methyl]-1H-pyrazolo[4,3-b]pyridin-6-amine (370 mg, 0.93 mmol, 1.00 equiv) in dichloromethane (20 mL) was added triphosgene (110.7 mg, 0.37 mmol, 1.00 equiv) at ambient temperature. Stirred for 2 h, the reaction mixture was diluted with 100 mL of sat. NaHCO₃ and extracted with dichloromethane (100 mL×3). The combined organic layers were washed with brine (100 mL×3) and dried over anhydrous sodium sulfate. Filtration and concentration under vacuum gave 6-(1-phenylethyl)-1-((2-(trimethylsilyl)ethoxy)methyl)-5,6-dihydro-1H-pyrazolo[3',4':5,6]pyrido[3,2-d]pyrimidin-7(8H)-one (45J) as a yellow solid. MS m/z [M+H]⁺ (ESI): 424.
Step 10

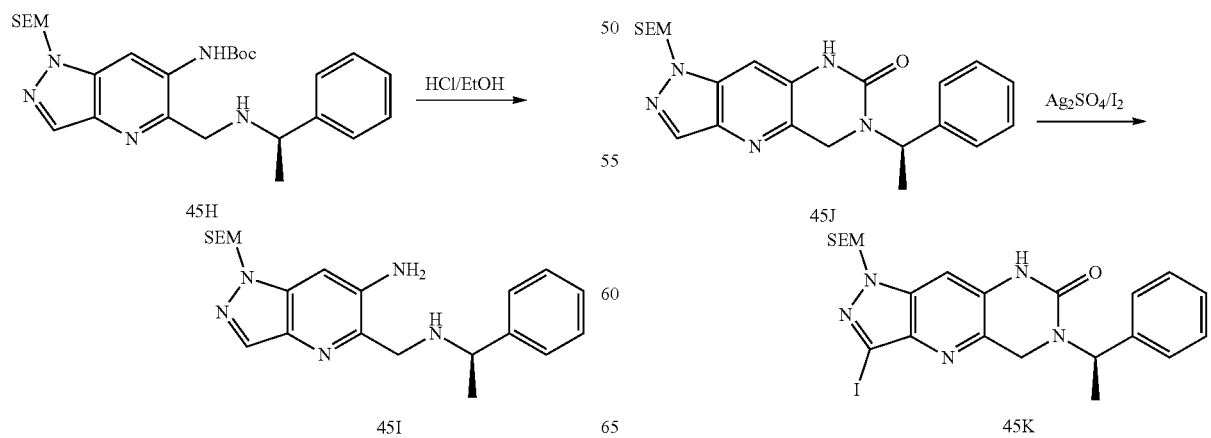

119

Into a 50-mL round-bottom flask was placed a solution of 6-(1-phenylethyl)-1-((2-(trimethylsilyl)ethoxy)methyl)-5,6-dihydro-1H-pyrazolo[3',4':5,6]pyrido[3,2-d]pyrimidin-7(8H)-one (400 mg, 0.94 mmol, 1.00 equiv), silver sulfate (383.5 mg, 1.23 mmol, 1.30 equiv) and iodine (312.2 mg, 1.23 mmol, 1.30 equiv) in ethanol/methanol (1:1) (20 mL). After stirring for 1 h at 50° C., the reaction mixture was diluted with 100 mL of sat. Na$_2$SO$_3$ and extracted with ethyl acetate (100 mL×3). The combined organic layers were washed with brine (100 mL×3) and dried over anhydrous sodium sulfate. Upon filtration and concentration under vacuum, the residue was purified by a flash chromatography on silica gel column eluting with dichloromethane/methanol (300:1-100:1) to afford 3-iodo-6-(1-phenylethyl)-1-((2-(trimethylsilyl)ethoxy)methyl)-5,6-dihydro-1H-pyrazolo[3',4':5,6]pyrido[3,2-d]pyrimidin-7(8H)-one (45K) as a yellow solid. MS m/z [M+H]$^+$ (ESI): 550.

Step 11

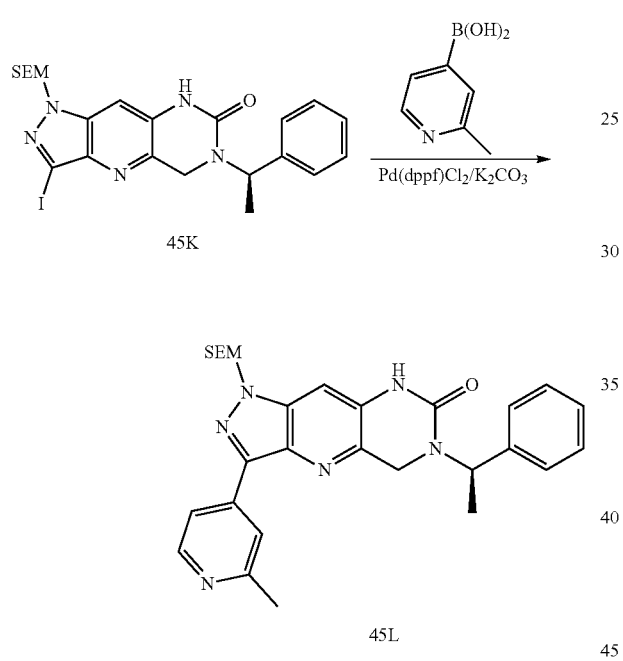

Into a 20-mL round-bottom flask purged and maintained with an inert atmosphere of nitrogen, was placed a mixture of 3-iodo-6-(1-phenylethyl)-1-((2-(trimethylsilyl)-ethoxy)methyl)-5,6-dihydro-1H-pyrazolo[3',4':5,6]pyrido[3,2-d]pyrimidin-7(8H)-one (130 mg, 0.24 mmol, 1.00 equiv), Pd(dppf)Cl$_2$ (14.6 mg, 0.02 mmol, 0.10 equiv), potassium carbonate (98 mg, 0.71 mmol, 3.00 equiv) and (2-methylpyridin-4-yl)boronic acid (48.7 mg, 0.36 mmol, 1.50 equiv) in dioxane:water (4:1) (5 mL). Stirred for 15 h at 80° C., the reaction mixture was diluted with water (100 mL) and extracted with ethyl acetate (100 mL×3). The combined organic layers were washed with brine (100 mL×3) and dried over anhydrous sodium sulfate. After filtered and concentrated under vacuum, the residue was purified by a flash chromatography on silica gel column eluting with dichloromethane/methanol (300:1-100:1) to afford 3-(2-methylpyridin-4-yl)-6-(1-phenylethyl)-1-((2-(trimethylsilyl)ethoxy)methyl)-5,6-dihydro-1H-pyrazolo[3',4':5,6]pyrido[3,2-d]pyrimidin-7(8H)-one (45L) as a yellow solid. MS m/z [M+H]$^+$ (ESI): 515.

Step 12

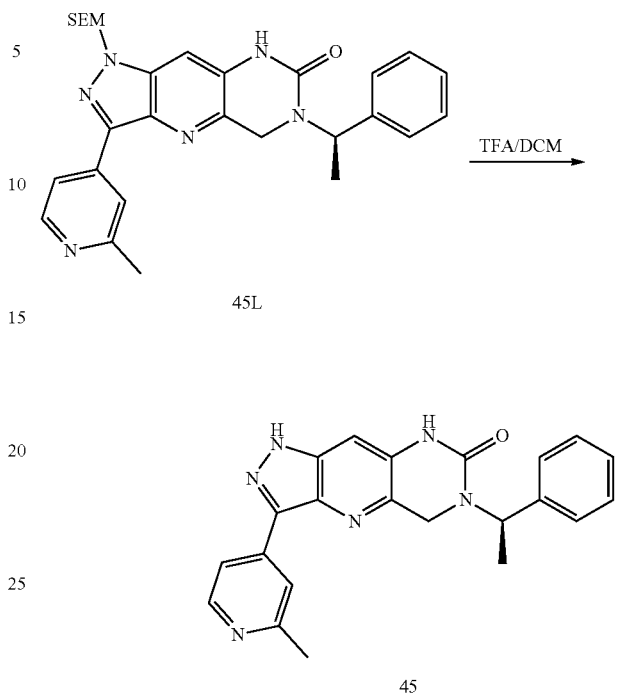

Into a 25-mL round-bottom flask, was placed a solution of 3-(2-methylpyridin-4-yl)-6-(1-phenylethyl)-1-((2-(trimethylsilyl)ethoxy)methyl)-5,6-dihydro-1H-pyrazolo[3',4':5,6]pyrido[3,2-d]pyrimidin-7(8H)-one (60 mg, 0.12 mmol, 1.00 equiv) and TFA (1 mL) in dichloromethane (10 mL). The resulting solution was stirred for 2 h at ambient temperature. Upon concentration under reduce pressure, the residue was purified by Prep-HPLC with the following conditions: [X Bridge Prep shield RP 18, 5 µm, 19×150 mm; Mobile phase, water (0.05% ammonium bicarbonate)/acetonitrile (30%~75% in 10 min); Detector, 254 nm, 220 nm; RT=6.7 min.] to afford (R)-3-(2-methylpyridin-4-yl)-6-(1-phenylethyl)-5,6-dihydro-1H-pyrazolo[3',4':5,6]-pyrido-[3,2-d]pyrimidin-7(8H)-one (45) as light yellow solid. $^1$H-NMR (400 MHz, DMSO-d$_6$): δ ppm 13.38 (s, NH), 9.77 (s, 1H), 8.53-8.52 (d, J=4 Hz, 1H), 8.14-8.13 (d, J=4 Hz, 1H), 8.11(s, 1H), 7.45-7.38 (m, 4H), 7.33-7.31 (m, 2H), 5.80-5.75 (m, 1H), 4.65-4.61 (d, J=16 Hz, 1H), 4.10-4.06 (d, J=16 Hz, 1H), 2.53 (s, 3H), 1.63-1.61 (d, J=8 Hz, 3H). MS m/z [M+H]$^+$ (ESI): 385.

Example 46

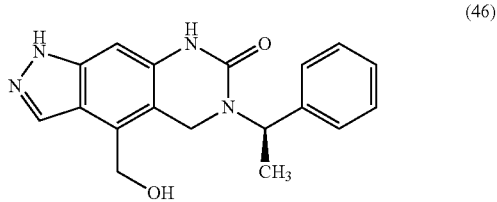 [SMILES: C[C@H](c1ccccc1)N1Cc2c(cc3[nH]ncc3c2CO)NC1=O]

(46)

121

(R)-4-(hydroxymethyl)-6-(1-phenylethyl)-5,6-di-hydro-1H-pyrazolo[4,3-g]quinazolin-7(8H)-one

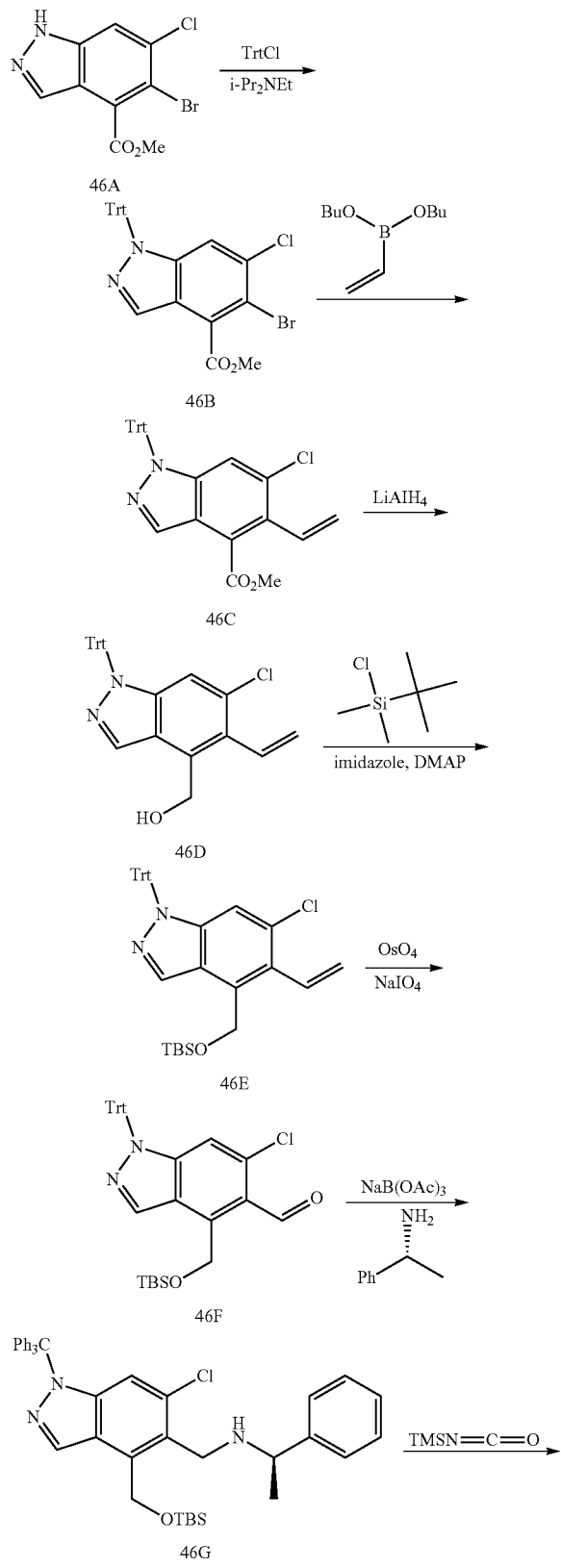

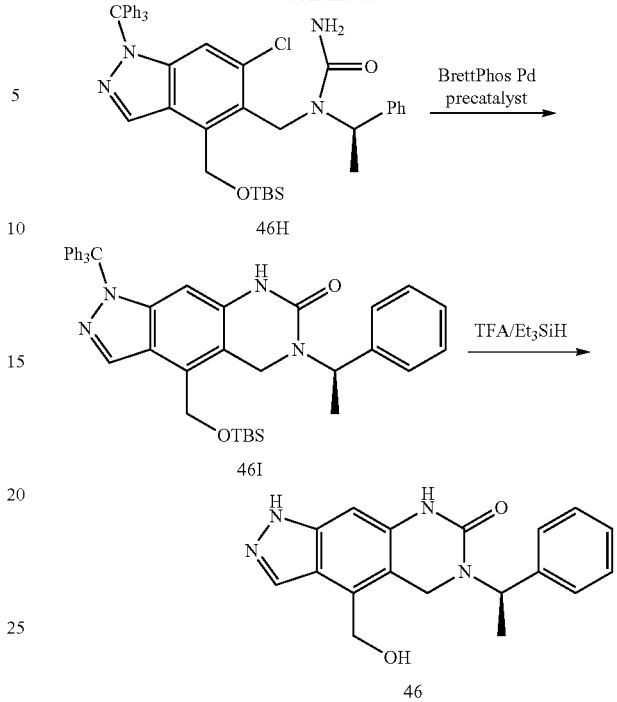

In a manner similar to that described in Example 26 (Step 2), methyl 5-bromo-6-chloro-1H-indazole-4-carboxylate (commercially available, CAS [1037841-34-1], also described in PCT Int Appl. 2008084717) was treated with trityl chloride and Hunig's base (DCM, room temperature, overnight) to provide methyl 5-bromo-6-chloro-1-trityl-1H-indazole-4-carboxylate (46B).

In a manner similar to that described in Example 35 (Step 1), 46B was reacted with vinylboronic acid dibutyl ester and 1,1'-bis(diphenylphosphino)ferrocene-palladium(ii)dichloride dichloromethane complex (dioxane-water, sodium bicarbonate, microwaved 60 min at 80° C.) to provide methyl 6-chloro-1-trityl-5-vinyl-1H-indazole-4-carboxylate (46C).

Compound 46C was reduced with $LiAlH_4$ (THF, 0° C., 60 min) and then protected with TBS-Cl (catalytic DMAP, imidazole, DMF, room temperature, overnight) to provide 4-(((tert-butyldimethylsilyl)oxy)methyl)-6-chloro-1-trityl-5-vinyl-1H-indazole (46E).

Compound 46E was reacted with osmium tetraoxide and sodium periodate (water-THF, room temperature, overnight) to provide 4-(((tert-butyldimethylsilyl)oxy)methyl)-6-chloro-1-trityl-1H-indazole-5-carbaldehyde (46F).

In a manner similar to that described in Example 26 (Step 4), 46F was reacted with sodium triacetoxyborohydride and (R)-(+)-1-phenyl ethylamine (DCE) to provide (R)—N-((4-(((tert-butyldimethylsilyl)oxy)methyl)-6-chloro-1-trityl-1H-indazol-5-yl)methyl)-1-phenylethanamine (46G). LCMS: [M+H]$^+$ m/z 672.

Compound 46G could be converted to compound 46 by the following sequence:

(1) treatment with trimethylsilyl isocyanate (to provide (R)-1-((4-(((tert-butyldimethylsilyl)oxy)methyl)-6-chloro-1-trityl-1H-indazol-5-yl)methyl)-1-(1-phenylethyl)urea (46H));

(2) reaction with Brettphos palladacycle (in a manner similar to that described in Example 44, Step 1; to provide (R)-4-(((tert-butyldimethylsilyl)oxy)methyl)-6-(1-phenylethyl)-1-trityl-5,6-dihydro-1H-pyrazolo[4,3-g]quinazolin-7(8H)-one (46I)); and (3) final deprotection with TFA-EtSi₃H to provide (R)-4-(hydroxymethyl)-6-(1-phenylethyl)-5,6-dihydro-1H-pyrazolo[4,3-g]quinazolin-7(8H)-one (in a manner similar to that described in Example 26, Step 8).

Example 47

(R)-3-(6,7-dihydrothiazolo[5,4-c]pyridin-5(4H)-yl)-6-(1-phenylethyl)-5,6-dihydro-1H-pyrazolo[4,3-g]quinazolin-7(8H)-one

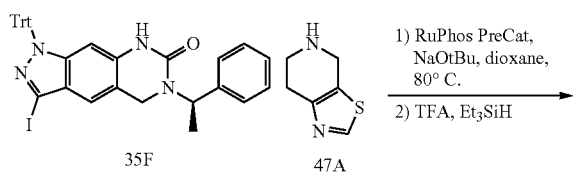

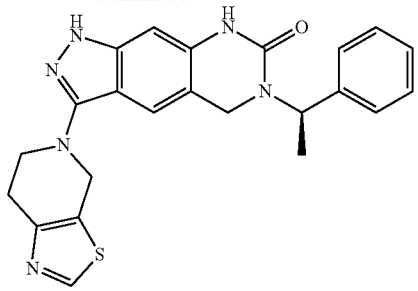

47

In a manner similar to that described in Example 24 (Steps 6-7), compound 35F was sequentially reacted with 4,5,6,7-tetrahydrothiazolo[5,4-c]pyridine hydrochloride (47A) (Ru-Phos-G3-precatalyst ((2-dicyclohexylphosphino-2',6'-diisopropoxy-1,1'-biphenyl)[2-(2'-amino-1,1'-biphenyl)] palladium(II) methanesulfonate), sodium tert-butoxide, overnight, 80° C.) and then TFA/Et₃SiH to provide compound 47. LCMS: [M+H]⁺ m/z 431.

Table 1 below provides data for the compounds of the above examples as well as additional examples. The compounds of the additional examples were prepared following procedures similar to those of the Example indicated in the "Route Used" column. No example number in the "Route Used" column means that the preparation is described in the written examples above. The compounds of Examples (4)-(9), (11)-(15), (17)-(26), (30)-(37), (39)-(41), (43), (44), and (47) are trifluoroacetate salts. The compounds of Examples (27), (28) and (29) are formate salts.

TABLE 1

| Example | Structure and Name | Exact Mass [M + M]+ | Route Used |
|---|---|---|---|
| 1 | 3-(2-methylpyridin-4-yl)-1,8-dihydro-7H-pyrazolo[4,3-g]quinolin-7-one | Calc'd 277, found 277 | — |
| 2 | 6-bromo-3-(2-methylpyridin-4-yl)-1,8-dihydro-7H-pyrazolo[4,3-g]quinolin-7-one | Calc'd 355, found 355 | — |

TABLE 1-continued

| Example | Structure and Name | Exact Mass [M + M]+ | Route Used |
|---|---|---|---|
| 3 | 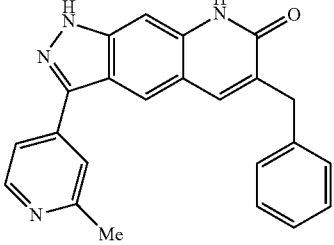<br>6-benzyl-3-(2-methylpyridin-4-yl)-1,8-dihydro-7H-pyrazolo[4,3-g]quinolin-7-one | Calc'd 367, found 367 | — |
| 4 | 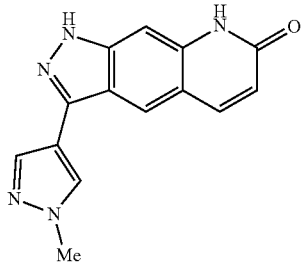 [SMILES: Cn1cc(-c2n[nH]c3cc4[nH]c(=O)ccc4cc23)cn1]<br>3-(1-methyl-1H-pyrazol-4-yl)-1,8-dihydro-7H-pyrazolo[4,3-g]quinolin-7-one | Calc'd 266, found 266 | — |
| 5 | 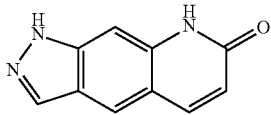<br>1,8-dihydro-7H-pyrazolo[4,3-g]quinolin-7-one | Calc'd 186, found 186 | 1 |
| 6 | 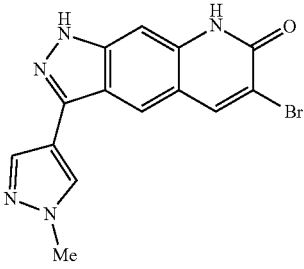 [SMILES: Cn1cc(-c2n[nH]c3cc4[nH]c(=O)c(Br)cc4cc23)cn1]<br>6-bromo-3-(1-methyl-1H-pyrazol-4-yl)-1,8-dihydro-7H-pyrazolo[4,3-g]quinolin-7-one trifluoroacetate | Calc'd 344, found 344 | 2 |
| 7 | 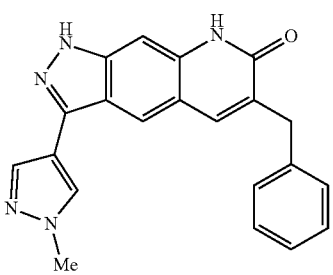 [SMILES: Cn1cc(-c2n[nH]c3cc4[nH]c(=O)c(Cc5ccccc5)cc4cc23)cn1]<br>6-benzyl-3-(1-methyl-1H-pyrazol-4-yl)-1,8-dihydro-7H-pyrazolo[4,3-g]quinolin-7-one | Calc'd 356, found 356 | 4 |

TABLE 1-continued

| Example | Structure and Name | Exact Mass [M + M]+ | Route Used |
|---|---|---|---|
| 8 | 8-hydroxy-3-(2-methylpyridin-4-yl)-5,6-dihydro-1H-pyrazolo[4,3-g]quinolin-7(8H)-one | Calc'd 295; found 295 | — |
| 9 | 3-(2-methylpyridin-4-yl)-5,6,7,9-tetrahydroazepino[3,2-f]indazol-8(1H)-one | Calc'd 293; found 293 | — |
| 10 | (R)-6-(1-(4-fluorophenyl)ethyl)-3-(2-methylpyridin-4-yl)-5,6-dihydro-1H-pyrazolo[4,3-g]quinazolin-7(8H)-one | Calc'd 402; found 402 | — |
| 11 | 7-(4-fluorobenzyl)-9-hydroxy-3-(2-methylpyridin-4-yl)-5,6,7,9-tetrahydro-[1,3]diazepino[5,4-f]indazol-8(1H)-one | Calc'd 418; found 418 | — |

TABLE 1-continued

| Example | Structure and Name | Exact Mass [M + M]+ | Route Used |
|---|---|---|---|
| 12 | (R)-7-(1-(4-fluorophenyl)ethyl)-3-(2-methylpyridin-4-yl)-5,6,7,9-tetrahydro-[1,3]diazepino[5,4-f]indazol-8(1H)-one | Calc'd 416; found 416 | — |
| 13 | 3-(2-methylpyridin-4-yl)-5,6-dihydro-1H-pyrazolo[4,3-g]quinazolin-7(8H)-one | Calc'd 280; found 280 | — |
| 14 | 6-benzyl-3-(2-methylpyridin-4-yl)-5,6-dihydro-1H-pyrazolo[4,3-g]quinazolin-7(8H)-one | Calc'd 370; found 370 | 14 |
| 15 | (R)-3-(1-methyl-1H-benzo[d][1,2,3]triazol-6-yl)-6-(1-phenylethyl)-1H-pyrazolo[4,3-g]quinazoline-5,7(6H,8H)-dione | Calc'd 438; found 438 | — |

TABLE 1-continued

| Example | Structure and Name | Exact Mass [M + M]+ | Route Used |
|---|---|---|---|
| 16 | 3-(2-methylpyridin-4-yl)-6-(2,3,4,5-tetrahydrobenzo[b]oxepin-5-yl)-5,6-dihydro-1H-pyrazolo[4,3-g]quinazolin-7(8H)-one | Calc'd 426; found 426 | 10 |
| 17 | (S)-1-(4-fluorophenyl)-2-methoxy-N-(3-(2-methylpyridin-4-yl)-1H-azeto[3,2-f]indazol-5(6H)-ylidene)ethanamine | Calc'd 432; found 432 | 10 |
| 18 | 6-(2-methoxybenzyl)-3-(2-methylpyridin-4-yl) 5,6-dihydro-1H-pyrazolo[4,3-g]quinazolin-7(8H)-one | Calc'd 400; found 400 | 10 |
| 19 | 6-(2-methoxyphenethyl)-3-(2-methylpyridin-4-yl)-5,6-dihydro-1H-pyrazolo[4,3-g]quinazolin-7(8H)-one | Calc'd 414; found 414 | 10 |

TABLE 1-continued

| Example | Structure and Name | Exact Mass [M + M]+ | Route Used |
|---|---|---|---|
| 20 | (R)-3-(2-methylpyridin-4-yl)-6-(1-phenylethyl)-5,6-dihydro-1H-pyrazolo[4,3-g]quinazolin-7(8H)-one 2,2,2-trifluoroacetate | Calc'd 384; found 384 | 10 |
| 21 | 6-((6-methylpyridin-2-yl)methyl)-3-(2-methylpyridin-4-yl)-5,6-dihydro-1H-pyrazolo[4,3-g]quinazolin-7(8H)-one | Calc'd 385; found 385 | 10 |
| 22 | (R)-3-(2-methylpyridin-4-yl)-6-(6,7,8,9-tetrahydro-5H-benzo[7]annulen-5-yl)-5,6-dihydro-1H-pyrazolo[4,3-g]quinazolin-7(8H)-one | Calc'd 424; found 424 | 10 |
| 23 | (R)-3-(2-methylpyridin-4-yl)-6-(1-phenylethyl)-1H-pyrazolo[4,3-g]quinazoline-5,7(6H,8H)-dione | Calc'd 398; found 398 | 15 |

TABLE 1-continued

| Example | Structure and Name | Exact Mass [M + M]+ | Route Used |
|---|---|---|---|
| 24 | 3-morpholino-1H-pyrazolo[4,3-g]quinolin-7(8H)-one | Calc'd 271; found 271 | — |
| 25 | 3-(piperidin-1-yl)-1H-pyrazolo[4,3-g]quinolin-7(8H)-one | Calc'd 269; found 269 | 24 |
| 26 | (R)-3-(1-methyl-1H-benzo[d][1,2,3]triazol-6-yl)-6-(1-phenylethyl)-5,6-dihydro-1H-pyrazolo[4,3-g]quinazolin-7(8H)-one | Calc'd 424; found 424 | — |
| 27 | (R)-5-(7-oxo-6-(1-phenylethyl)-5,6,7,8-tetrahydro-1H-pyrazolo[4,3-g]quinazolin-3-yl)picolinonitrile | Calc'd 395; found 395 | 26 |

TABLE 1-continued

| Example | Structure and Name | Exact Mass [M + M]+ | Route Used |
|---|---|---|---|
| 28 | (R)-3-(2-methoxypyrimidin-5-yl)-6-(1-phenylethyl)-5,6-dihydro-1H-pyrazolo[4,3-g]quinazolin-7(8H)-one formate | Calc'd 401; found 401 | 26 |
| 29 | (R)-3-(ethylamino)-6-(1-phenylethyl)-5,6-dihydro-1H-pyrazolo[4,3-g]quinazolin-7(8H)-one | Calc'd 336; found 336 | — |
| 30 | 6-((R)-1-phenylethyl)-3-(((S)-1,1,1-trifluoropropan-2-yl)amino)-5,6-dihydro-1H-pyrazolo[4,3-g]quinazolin-7(8H)-one | Calc'd 404; found 404 | — |
| 31 | (R)-6-(1-phenylethyl)-5,6-dihydro-1H-pyrazolo[4,3-g]quinazolin-7(8H)-one 2,2,2-trifluoroacetate | Calc'd [M + Na]+ 315; found 315 | — |
| 32 | (R)-3-amino-6-(1-phenylethyl)-5,6-dihydro-1H-pyrazolo[4,3-g]quinazolin-7(8H)-one | Calc'd 308; found 308 | — |

TABLE 1-continued

| Example | Structure and Name | Exact Mass [M + M]+ | Route Used |
|---------|--------------------|---------------------|------------|
| 33 | (R)-methyl (7-oxo-6-(1-phenylethyl)-5,6,7,8-tetrahydro-1H-pyrazolo[4,3-g]quinazolin-3-yl)carbamate 2,2,2-trifluoroacetate | Calc'd 366; found 366 | — |
| 34 | (R)-N-(7-oxo-6-(1-phenylethyl)-5,6,7,8-tetrahydro-1H-pyrazolo[4,3-g]quinazolin-3-yl)acetamide | Calc'd 350; found 350 | 33 |
| 35 | (R)-3-methoxy-6-(1-phenylethyl)-5,6-dihydro-1H-pyrazolo[4,3-g]quinazolin-7(8H)-one | Calc'd 323, found 323 | — |
| 36 | (R)-3-(2-methoxyethoxy)-6-(1-phenylethyl)-5,6-dihydro-1H-pyrazolo[4,3-g]quinazolin-7(8H)-one | Calc'd 367, found 367 | 35 |
| 37 | (R)-3-(2-hydroxyethoxy)-6-(1-phenylethyl)-5,6-dihydro-1H-pyrazolo[4,3-g]quinazolin-7(8H)-one | Calc'd 353, found 353 | 35 |

TABLE 1-continued

| Example | Structure and Name | Exact Mass [M + M]+ | Route Used |
|---|---|---|---|
| 38 | 6-((R)-1-phenylethyl)-3-((tetrahydrofuran-3-yl)oxy)-5,6-dihydro-1H-pyrazolo[4,3-g]quinazolin-7(8H)-one | Calc'd 379, found 379 | — |
| 39 | (R)-6-(1-phenylethyl)-3-((tetrahydro-2H-pyran-4-yl)oxy)-5,6-dihydro-1H-pyrazolo[4,3-g]quinazolin-7(8H)-one | Calc'd 393, found 393 | 38 |
| 40 | (R)-3-cyclopropyl-6-(1-phenylethyl)-5,6-dihydro-2H-pyrazolo[4,3-g]quinazolin-7(8H)-one | Calc'd 333, found 333 | — |
| 41 | (R)-3-(2-fluoropyridin-4-yl)-6-(1-phenylethyl)-5,6-dihydro-1H-pyrazolo[4,3-g]quinazolin-7(8H)-one | Calc'd 388, found 388 | 40 |

TABLE 1-continued

| Example | Structure and Name | Exact Mass [M + M]+ | Route Used |
|---|---|---|---|
| 42 | (R)-3-morpholino-6-(1-phenylethyl)-5,6-dihydro-1H-pyrazolo[4,3-g]quinazolin-7(8H)-one | Calc'd 378, found 378 | — |
| 43 | (R)-3-iodo-6-(1-phenylethyl)-5,6-dihydro-1H-pyrazolo[4,3-g]quinazollin-7(8H)-one | Calc'd 419, found 419 | 35 |
| 44 | (R)-3-amino-6-(1-phenylethyl)-1H-pyrazolo[4,3-g]quinazoline-5,7(6H,8H)-dione | Calc'd 322, found 322 | — |
| 45 | (R)-3-(2-methylpyridin-4-yl)-6-(1-phenylethyl)-5,6-dihydro-1H-pyrazolo[3',4':5,6]-pyrido-[3,2-d]pyrimidin-7(8H)-one | Calc'd 385, found 385 | — |
| 46 | (R)-4-(hydroxymethyl)-6-(1-phenylethyl)-5,6-dihydro-1H-pyrazolo[4,3-g]quinazolin-7(8H)-one | | |

TABLE 1-continued

| Example | Structure and Name | Exact Mass [M + M]+ | Route Used |
|---------|-------------------|---------------------|------------|
| 47 | (R)-3-(6,7-dihydrothiazolo[5,4-c]pyridin-5(4H)-yl)-6-(1-phenylethyl)-5,6-dihydro-1H-pyrazolo[4,3-g]quinazolin-7(8H)-one | Calc'd 431, found 431 | — |

Assays
Active Human ERK2 (hERK2) Activity Assay:

Activated ERK2 activity was determined in an IMAP-FP assay (Molecular Devices). Using this assay format, the potency ($IC_{50}$) of each compound was determined from a 10 point (1:3 serial dilution, 3 µM starting compound concentration) titration curve using the following outlined procedure. To each well of a black Corning 384-well plate (Corning Catalog #3575), 7.5 nL of compound (3333 fold dilution in final assay volume of 25 µL) was dispensed, followed by the addition of 15 µL of kinase buffer (tween containing kinase buffer, Molecular Devices) containing 0.0364 ng/mL (0.833 nM) of phosphorylated active hERK2 enzyme. Following a 15 minute compound & enzyme incubation, each reaction was initiated by the addition of 10 µL kinase buffer containing 2.45 µM ERK2 IMAP substrate peptides (2.25 µM-unlabeled peptide and 200 nM-labeled peptide, and 75 µM ATP. The final reaction in each well of 25 µL consists of 0.5 nM hERK2, 900 nM unlabeled peptide, 80 nM labeled-peptide, and 30 µM ATP. Phosphorylation reactions were allowed to proceed for 60 minutes and were immediately quenched by the addition of 60 µL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer).

Table 2 below provides the ERK 2 Human average $IC_{50}$ (in nM) data for the compounds of Examples 4-43.

TABLE 2

| Ex | $IC_{50}$ |
|----|-----------|
| 4  | 0.3 |
| 5  | 228 |
| 6  | 0.3 |
| 7  | 0.3 |
| 8  | 3.6 |
| 9  | 252 |
| 10 | 0.3 |
| 11 | 459 |
| 12 | 72.0 |
| 13 | 0.6 |
| 14 | 0.5 |
| 15 | 1.7 |
| 16 | 4.8 |
| 17 | 0.7 |
| 18 | 0.8 |
| 19 | 2.3 |
| 20 | 0.3 |
| 21 | 0.6 |
| 22 | 24 |
| 23 | 3.7 |
| 24 | 12 |
| 25 | 42 |
| 26 | 0.3 |
| 27 | 10 |
| 28 | 0.6 |
| 29 | 22 |
| 30 | 25 |
| 31 | 55 |
| 32 | 21 |
| 33 | 5.2 |
| 34 | 2.3 |
| 35 | 114 |
| 36 | 6.4 |
| 37 | 20 |
| 38 | 21 |
| 39 | 10 |
| 40 | 24 |
| 41 | 0.3 |
| 42 | 9.0 |
| 43 | 48 |

The compounds of Examples 44, 45, and 47 had an ERK 2 Human average $IC_{50}$ (in nM) of 45, 0.5, and 24 respectively.

Active Mouse ERK2 (mERK2) Activity Assay:

Activated ERK2 activity was determined in an IMAP-FP assay (Molecular Devices). Using this assay format, the potency ($IC_{50}$) of each compound was determined from a 10 point (1:3 serial dilution, 3 µM starting compound concentration) titration curve using the following outlined procedure. To each well of a black Corning 384-well plate (Corning Catalog #3575), 7.5 nL of compound (3333 fold dilution in final assay volume of 25 µL) was dispensed, followed by the addition of 15 µL of kinase buffer (tween containing kinase buffer, Molecular Devices) containing 0.0133 ng/mL (0.316 nM) of phosphorylated active mERK2 enzyme. Following a 15 minute compound & enzyme incubation, each reaction was initiated by the addition of 10 µL kinase buffer containing 2.45 µM ERK2 IMAP substrate peptides (2.25 µM-unlabeled peptide and 200 nM-labeled peptide, and 75 µM ATP. The final reaction in each well of 25 μL consists of 0.19 nM mERK2, 900 nM unlabeled peptide, 80 nM labeled-peptide, and 30 uM ATP. Phosphorylation reactions were allowed to proceed for 45 minutes and were immediately quenched by the addition of 60 μL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer).

Table 3 below provides the ERK 2 MAPK1 Mouse $IC_{50}$ (in nM) data for the compounds of Examples 1-3.

TABLE 3

| Ex | $IC_{50}$ |
|---|---|
| 1 | 0.4 |
| 2 | 0.2 |
| 3 | 0.2 |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

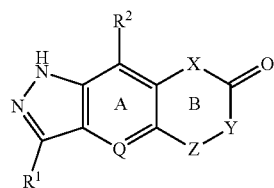

(I)

or a pharmaceutically acceptable salt thereof, wherein:
Q is selected from the group consisting of: —($CR^3$)— and N;
X is selected from the group consisting of: NH and N—O;
Y is —N($R^9$)—;
Z is selected from the group consisting of: —C(=O)—, —C($R^7R^8$)— and —C($R^7R^8$)—C($R^7R^8$)— wherein each $R^7$ and each $R^8$ is independently selected;
$R^1$ is selected from the group consisting of: —$NR^{12}R^{13}$, —$OR^{10}$, —O—($R^{10}$)—O—$R^{10}$, —O—$R^{10}$—OH, —O—$R^{11}$, ($C_3$-$C_7$)cycloalkyl, substituted ($C_3$-$C_7$)cycloalkyl, heteroaryl, substituted heteroaryl, heterocycloalkyl, substituted heterocycloalkyl, ($C_6$-$C_{14}$)aryl, substituted ($C_6$-$C_{14}$)aryl, fused arylheteroaryl, substituted fused arylheteroaryl, fused heterocycloalkylheteroaryl, and substituted fused heterocycloalkylheteroaryl;
and wherein said substituted $R^1$ groups are substituted with 1 to 3 substituents independently selected from the group consisting of: —($C_1$-$C_6$)alkyl, halo, CN, —OH, —$OR^{10}$, —$CF_3$, =O, —$NH_2$, —NH($C_1$-$C_6$)alkyl, —$S(O)_2$($C_1$-$C_6$)alkyl, —($C_3$-$C_6$)cycloalkyl, —(($C_1$-$C_6$)alkyl)OH, —($C_3$-$C_6$)cycloalkyl-S—($C_3$-$C_6$)cycloalkyl, —N(($C_1$-$C_6$)alkyl)$_2$ wherein each alkyl is independently selected, —C(O)O—($C_1$-$C_6$)alkyl, —C(O)OH, —$OCF_3$, —C(O)NH($C_1$-$C_6$)alkyl, heteroaryl, —($C_1$-$C_6$)alkyl)-O—($C_1$-$C_6$)alkyl, fused heteroarylaryl-, heterocycloalkyl, and heterocycloalkenyl;
and wherein the alkyl moieties of the $R^1$ groups, are optionally substituted with 1 to 3 substituents independently selected from the group consisting of: ($C_1$-$C_6$) alkoxy, halo, CN, —OH, =O, —$CF_3$, —$NH_2$, —NH ($C_1$-$C_6$)alkyl, —$S(O)_2$($C_1$-$C_6$)alkyl, fused heteroarylaryl-, heterocycloalkyl, and heterocycloalkenyl;
and wherein said heteroaryl moiety of said $R^1$ groups is a 5-10 membered ring comprising 1-3 heteroatoms independently selected from the group consisting of: N, O and S, and wherein the remaining ring atoms are carbon (and wherein said heteroaryl definition applies to the heteroaryl moieties in the $R^1$ fused heteroarylheteroaryl, substituted fused heteroarylheteroaryl, fused arylheteroaryl, fused heterocycloalkyl-heteroaryl, substituted fused heterocycloalkylheteroaryl, and fused heteroarylaryl- groups); and wherein said heterocycloalkyl moiety of said $R^1$ groups is a 3-10 membered ring comprising 1-3 heteroatoms independently selected from the group consisting of: N, O and S, and wherein the remaining ring atoms are carbon (and wherein said heterocycloalkyl definition applies to the heterocycloalkyl moieties in the $R^1$ fused heterocycloalkylheteroaryl and substituted fused heterocycloalkylheteroaryl groups;
and wherein said fused arylheteroaryl moiety of said $R^1$ groups comprises a $C_6$-$C_{10}$ aryl fused to a heteroaryl, as defined above, wherein the aryl and the heteroaryl have 2 ring atoms in common;
$R^2$ is selected from the group consisting of: H, halo, —$NH_2$, —OH and —($C_1$-$C_3$)alkyl;
$R^3$ is selected from the group consisting of: H, halo, ($C_1$-$C_6$alkyl), and ($C_1$-$C_6$alkyl) substituted with 1-2 —OH groups, —($C_3$-$C_6$ cycloalkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, and -($C_1$-$C_6$alkyl)-heterocycloalkyl, wherein said heterocycloalkyl is as defined above for $R^1$;
each $R^6$, $R^7$ and $R^8$ is independently selected from the group consisting of: H, halo, ($C_6$-$C_{14}$)aryl($C_1$-$C_6$)-alkyl-, and substituted ($C_6$-$C_{14}$)aryl($C_1$-$C_6$)alkyl-, heteroaryl, substituted heteroaryl, heteroaryl($C_1$-$C_6$) alkyl-, substituted heteroaryl($C_1$-$C_6$)alkyl-, fused ($C_3$-$C_7$)cycloalkyl($C_6$-$C_{14}$)aryl, substituted fused ($C_3$-$C_7$) cycloalkyl($C_6$-$C_{14}$)aryl, fused heterocycloalkyl($C_6$-$C_{14}$)aryl, substituted fused heterocycloalkyl($C_6$-$C_{14}$) aryl; wherein said substituted $R^6$, $R^7$, $R^8$ moieties are substituted with 1-3 substitutents independently selected from the group consisting of: halo, ($C_1$-$C_6$) alkyl, ($C_1$-$C_6$)alkyl-O—($C_1$-$C_6$)alkyl; and wherein said heteroaryl moiety and said heterocycloalkyl moiety is as defined above in $R^1$;
$R^9$ is selected from the group consisting of: ($C_6$-$C_{10}$)aryl ($C_1$-$C_6$)alkyl-, and substituted ($C_6$-$C_{14}$)aryl($C_1$-$C_6$) alkyl-, heteroaryl($C_1$-$C_6$)alkyl-, substituted heteroaryl ($C_1$-$C_6$)alkyl-, fused heterocycloalkyl($C_6$-$C_{14}$)aryl, substituted fused heterocycloalkyl($C_6$-$C_{14}$)aryl; wherein said substituted $R^9$ moieties are substituted with 1-3 substitutents independently selected from the group consisting of: halo, OH, CN, $CF_3$, ($C_1$-$C_6$)alkyl, ($C_1$-$C_6$)alkyl- O—($C_1$-$C_6$)alkyl; and wherein said heteroaryl moiety and said heterocycloalkyl moiety is as defined above for $R^1$;
each $R^{10}$ is independently selected from the group consisting of: $C_1$-$C_6$alkyl;

$R^{11}$ is selected from the group consisting of: a 4-7 membered heterocycloalkyl ring comprising 1-3 heteroatoms independently selected from the group consisting of: O, S and N; and $R^{12}$ and $R^{13}$ are independently selected from the group consisting of: H, $(C_1-C_6)$alkyl, —C(O)OR$^{10}$, —C(O)R$^{10}$; said alkyl group optionally substituted with 1-4 substitutents independently selected from the group consisting of halo.

2. The compound of claim 1, wherein Q is —(CR$^3$)—.

3. The compound of claim 1, wherein Z is —C(R$^7$R$^8$)—.

4. The compound of claim 1, wherein Z is —C(R$^7$R$^8$)—C(R$^7$R$^8$)—.

5. The compound of claim 1, wherein $R^7$ and $R^8$ are H.

6. The compound of claim 1, wherein Ring B is selected from the group consisting of: (d2), (d3), (e2), and (e3).

7. The compound of claim 1, wherein Ring B is selected from the group consisting of: (d2), (e2), and (e3).

8. The compound of claim 7 wherein $R^7$ and $R^8$ are H.

9. The compound of claim 1, wherein $R^9$ is selected from the group consisting of: heteroaryl$(C_1-C_6)$alkyl-, substituted heteroaryl$(C_1-C_6)$alkyl-, $(C_6-C_{10})$aryl$(C_1-C_6)$alkyl-, substituted $(C_6-C_{10})$aryl$(C_1-C_6)$alkyl-, fused heterocycloalkyl$(C_6-C_{10})$aryl, and fused substituted heterocycloalkyl$(C_6-C_{10})$aryl.

10. The compound of claim 1, wherein $R^9$ is selected from the group consisting of: (g1), (g2), (g3), (g4), (g6), (g7), (g8), (g9), (g10), (g11), (g12), (g13), (g14), and (g15).

11. The compound of claim 1, wherein $R^1$ is selected from the group consisting of: —NR$^{12}$R$^{13}$, —OR$^{10}$, —O—(R$^{10}$)—O—R$^{10}$, —O—R$^{10}$—OH, $(C_3-C_7)$cycloalkyl, substituted $(C_3-C_7)$cycloalkyl, heterocycloalkyl, substituted heterocycloalkyl, —OR$^{11}$, heteroaryl, substituted heteroaryl, fused arylheteroaryl, and fused substituted arylheteroaryl.

12. The compound of claim 1, wherein $R^1$ is selected from the group consisting of: —NH$_2$, —NHCH$_2$CH$_3$, —NHCH(CH$_3$)C(F)$_3$, —NHC(O)OCH$_3$, —NHC(O)CH$_3$, —OCH$_3$, —OCH$_2$CH$_2$OCH$_3$, —OCH$_2$CH$_2$OH, —(CH$_2$)$_3$—O—CH$_3$, cyclopropyl, (f1), (f2), (f3), (f4), (f8), (f9), (f11), and (f12).

13. A compound selected from the group consisting of compounds (10)-(12), (14)-(23), (26)-(30), (32)-(42), (44), (45), and (47), or a pharmaceutically acceptable salt thereof.

14. A pharmaceutical composition comprising a compound of claim 1, and a pharmaceutically acceptable carrier.

* * * * *